US009572873B2

(12) United States Patent
Nixon et al.

(10) Patent No.: US 9,572,873 B2
(45) Date of Patent: Feb. 21, 2017

(54) METHOD OF INDUCING A T LYMPHOCYTE RESPONSE USING T-CELL IMMUNOGENS DERIVED FROM ANTI-VIRAL PROTEINS

(71) Applicant: The Regents of the University of California, Oakland, CA (US)

(72) Inventors: Douglas F. Nixon, San Francisco, CA (US); Stephane Champiat, Nantes (FR); Keith Garrison, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/793,534

(22) Filed: Jul. 7, 2015

(65) Prior Publication Data

US 2016/0151470 A1    Jun. 2, 2016

Related U.S. Application Data

(63) Continuation of application No. 13/121,106, filed as application No. PCT/US2009/005381 on Sep. 28, 2009, now Pat. No. 9,084,762.

(60) Provisional application No. 61/101,590, filed on Sep. 30, 2008.

(51) Int. Cl.
| *A61K 39/21* | (2006.01) |
| *A61K 39/12* | (2006.01) |
| *C07K 7/06* | (2006.01) |
| *C07K 7/08* | (2006.01) |
| *C07K 14/16* | (2006.01) |
| *C07H 21/00* | (2006.01) |
| *A61K 39/00* | (2006.01) |
| *C07K 14/005* | (2006.01) |
| *A61K 38/10* | (2006.01) |
| *A61K 38/08* | (2006.01) |
| *A61K 38/16* | (2006.01) |

(52) U.S. Cl.
CPC .......... *A61K 39/0005* (2013.01); *A61K 39/12* (2013.01); *A61K 39/21* (2013.01); *C07H 21/00* (2013.01); *C07K 14/005* (2013.01); *A61K 38/08* (2013.01); *A61K 38/10* (2013.01); *A61K 38/162* (2013.01); *A61K 39/00* (2013.01); *A61K 2039/555* (2013.01); *A61K 2039/572* (2013.01); *A61K 2039/58* (2013.01); *C07K 7/06* (2013.01); *C07K 7/08* (2013.01); *C07K 14/16* (2013.01); *C12N 2740/16022* (2013.01); *C12N 2740/16034* (2013.01)

(58) Field of Classification Search
None
See application file for complete search history.

(56) References Cited

U.S. PATENT DOCUMENTS

| 2002/0164743 A1 | 11/2002 | Honjo et al. |
| 2004/0009951 A1 | 1/2004 | Malim et al. |
| 2004/0115184 A1 | 6/2004 | Smith et al. |
| 2005/0032039 A1 | 2/2005 | Sastry et al. |
| 2005/0054073 A1 | 3/2005 | Honjo et al. |
| 2006/0246568 A1 | 11/2006 | Honjo et al. |

FOREIGN PATENT DOCUMENTS

| WO | WO 02/103028 | 12/2002 |
| WO | WO 03/076586 | 9/2003 |
| WO | WO 2005/004798 | 1/2005 |
| WO | WO 2007/150077 | 12/2007 |

OTHER PUBLICATIONS

An et al., "APOBEC3G Genetic Variants and Their Influence on the Progression to AIDS", Journal of Virology 78 (20): 11070-11076 (2004).
Goila-Gaur and Strebel, "HIV-1 Vif, Apobec, and Intrinsic Immunity", Retrovirology 5:51 (2008).
Hundemer et al., "Identification of a new HLA-A2-restricted T-cell epitope within HM1.24 as immunotherapy target for multiple myeloma", Exp. Hematol. 34(4):486-496 (2006).
Motomura, et al.; "Genetic Recombination between Human Immunodeficiency Virus Type 1 (HIV-1) and HIV-2, Two Distinct Human Lentiviruses"; Journal of Virology; vol. 82, No. 4, pp. 1923-1933 (Feb. 2008).
Neil et al., "Tetherin inhibits retrovirus release and is antagonized by HIV-1 Vpu", Nature 451: 425-431 (2008).
Santiago et al., "Apobec3 encodes Rfv3, a gene influencing neutralizing antibody control of retrovirus infection", Science 321, 1343-1346 (2008).
Sasaki, et al.; "Monophosphoryl lipid A enhances both humoral and cell-mediated immune responses to DNA vaccination against human immunodeficiency virus type 1"; Infection and Immunity; vol. 65, No. 9, pp. 3520-3528 (Sep. 1997).
Simon, et al.; "Natural Variation in Vif: Differential Impact on APOBEC3G/3F and a Potential Role in HIV-1 Diversification"; PLoS Pathog; vol. 1, No. 1, e6, 9 pages (Sep. 2005).
Wiegand, et al.; "A second human antiretroviral factor, APOBEC3F, is suppressed by the HIV-1 and HIV-2 Vif proteins"; The EMBO Journal; vol. 23, pp. 2451-2458 (2004).

*Primary Examiner* — Nicole Kinsey White
(74) *Attorney, Agent, or Firm* — Bozicevic Field & Francis, LLP; Paula A. Borden

(57) ABSTRACT

Isolated polypeptides related to endogenous anti-viral polypeptides; and compositions, including immunogenic compositions, comprising a subject isolated polypeptide are disclosed herein. A subject isolated polypeptide comprises an amino acid sequence having substantial amino acid sequence identity to a contiguous stretch of amino acids of one or more endogenous anti-viral polypeptides, wherein the endogenous anti-viral polypeptides are polypeptides subject to proteolytic degradation as a result of the activity of one or more viral proteins. Also provided are diagnostic and treatment methods using the subject isolated polypeptides and compositions.

13 Claims, 19 Drawing Sheets

| HIV STATUS | group | | number of subjects | CD4 mean (/mm³) | Viral load mean (copies/ml) | number of responders against APOBEC pool | APOBEC pool responses mean (SFU / 10⁶ PBMC*) | % of responders |
|---|---|---|---|---|---|---|---|---|
| INFECTED | LTNP | | 7 | 828 | 117 | 5 | 486 | 71 |
| INFECTED | Chronic infection : | > Natural controllers | 19 | 643 | 393 | 6 | 45 | 32 |
| INFECTED | | > Haart suppressed | 20 | 626 | 51 | 8 | 54 | 40 |
| INFECTED | | > Viremics | 21 | 282 | 52656 | 3 | 34 | 14 |
| INFECTED | Children : | chronic infection | 73 | 836 | 18488 | 13 | 88 | 18 |
| EXPOSED | Children Exposed Uninfected | | 7 | | | 0 | 5 | 0 |
| NON EXPOSED | Healthy HIV- adults | | 33 | | | 2 | 18 | 6 |

*background SFU have been subtracted

FIG. 3

| ASB ID | APOBEC | |
|---|---|---|
| 4 | 25 | LTNP |
| 9 | 50 | LTNP |
| 15 | 2480 | LTNP |
| 63 | 85 | LTNP |
| 115 | 690 | LTNP |
| 134 | 70 | LTNP |
| 194 | 0 | LTNP |
| 72 | 15 | Chronic Prog. |

*Bold highlighting = values above background.

FIG. 7 (Table 2)

FIG. 8A (Table 3)

| Study ID | A3F-A2-194 | A3F-A2-363 | A3F-A2-11 | A3F-B58-159 | A3F-B58-225 | A3F-B7-43 | A3G-A2-177 | A3G-A2-31 | A3G-A2-164 | A3G-B58-196 | A3G-B58-B7-2 | A3G-2-27 | A3G-B7- |
|---|---|---|---|---|---|---|---|---|---|---|---|---|---|
| 585 |  |  |  | 0 | 0 |  |  |  |  | 0 | 0 |  |  |
| 720 |  |  | 0 | 35 | 15 |  |  |  |  | 35 | 5 |  |  |
| 791 |  |  | 0 | 0 | 0 |  |  |  |  | 0 | 0 |  |  |
| 804 |  |  | 5 | 10 | 5 |  |  |  |  | 5 | 0 |  |  |
| 839 |  |  | 30 | 300 | 0 |  |  |  |  | 135 | 90 |  |  |
| 850 |  |  | 15 | 5 | 0 |  |  |  |  | 0 | 0 |  |  |
| 1016 | 20 | 15 |  |  |  |  |  | 20 |  |  |  |  |  |
| 1068 |  |  | 0 | 0 | 0 |  |  |  |  | 10 | 0 |  |  |
| 1095 | 60 | 40 |  |  |  |  | 60 |  | 0 |  |  |  |  |
| 1119 | 0 | 5 |  |  |  |  | 30 |  | 0 |  |  |  |  |
| 1133 |  |  | 0 | 0 | 0 |  |  |  |  | 0 | 0 |  |  |
| 1143 |  |  | 0 | 0 | 20 |  |  |  |  | 0 | 0 |  |  |
| 1155 | 0 | 10 |  |  |  |  |  | 0 | 10 |  |  |  |  |
| 1157 |  |  |  |  |  |  |  |  |  |  |  | 30 | 25 |
| 1179 |  |  | 5 | 5 | 10 | 0 |  |  |  | 10 | 0 |  |  |
| 1185 |  |  | 0 | 0 | 0 |  |  |  |  | 15 | 0 |  |  |
| 1504 |  |  | 0 | 0 | 0 |  |  |  |  | 15 | 0 |  |  |
| 1508 |  |  | 0 | 0 | 10 |  |  |  |  | 10 | 0 |  |  |
| 1516 |  |  | 0 | 60 | 0 |  |  |  |  | 30 | 10 |  |  |
| 1531 |  |  | 0 | 0 | 5 |  |  |  |  | 0 | 0 |  |  |
| 1536 |  |  | 0 | 0 | 0 |  |  |  |  | 0 | 10 |  |  |
| 1545 |  |  | 15 | 5 | 0 |  |  |  |  | 0 | 0 |  |  |
| 1564 |  |  | 0 | 0 | 0 |  |  |  |  | 0 | 0 |  |  |
| 2003 |  |  |  |  |  | 0 |  |  |  |  |  |  | 0 |
| 2006 | 25 | 20 |  |  |  | 0 | 25 |  | 0 |  |  | 0 | 0 |
| 2013 |  |  |  |  |  |  |  |  |  |  |  |  |  |
| 2017 | 20 | 25 |  |  |  | 0 | 100 |  | 20 |  |  | 0 | 0 |
| 2039 | 45 | 10 |  |  |  |  | 0 |  | 0 |  |  |  |  |
| 2048 |  |  |  |  | 0 |  |  |  | 5 | 10 | 0 |  | 5 |
| 2055 |  | 15 |  |  |  |  |  |  |  |  | 0 | 15 |  |
| 2056 | 5 |  |  | 0 |  | 110 | 25 |  |  |  |  | 35 | 85 |
| 2058 |  |  |  |  |  |  |  |  |  |  |  |  |  |
| 2085 |  |  |  |  |  | 0 |  |  |  |  | 0 | 0 | 25 |
| 2087 |  |  |  |  |  | 5 |  |  |  |  |  | 10 | 5 |

FIG. 8B (Table 3 Cont.)

| Study ID | A3F-A2-194 | A3F-A2-393 | A3F-A2-11 | A3F-B58-159 | A3F-B58-225 | A3F-B7-43 | A3G-177 | A3G-A2-31 | A3G-A2-164 | A3G-B58-196 | A3G-B58-2 | A3G-B7- | A3G-B7-27 |
|---|---|---|---|---|---|---|---|---|---|---|---|---|---|
| 2096 | 25 | 35 | | | | | | 30 | 45 | | | | |
| 2100 | 30 | 10 | | | | | | 35 | 30 | | | | |
| 3001 | 35 | 15 | | | | | | 15 | 20 | | | 30 | |
| 3016 | 15 | 25 | | | 10 | | | 15 | 20 | | | 0 | |
| 3026 | 0 | 0 | 10 | | 20 | | | | 0 | 0 | 0 | | |
| 3051 | 10 | 20 | | | | | | 0 | 0 | | | | |
| 3058 | 5 | 0 | | | | | | 15 | 5 | | | 0 | 20 |
| 3073 | 0 | 20 | | | | | | 0 | 0 | | | | |
| 3076 | 5 | 10 | | | | | | 5 | 0 | | | 15 | 15 |
| 3086 | 0 | 0 | | | | | | 0 | 0 | | | | |
| 3092 | | | | | | | 0 | | | | | | |
| 3119 | | | | | | | 25 | | | | | 5 | 10 |
| 3130 | 5 | 5 | | | | | 0 | 5 | 0 | | | 30 | 20 |
| 6014 | | | | | | | | | | | | | |
| 6028 | 15 | 0 | | | | | | 0 | 0 | | | 5 | 0 |
| 6043 | | | | | | | | | | | | | |
| 6049 | 20 | 65 | | | | | | 35 | 0 | | | | |

FIG. 9A (Table 4)

| patient | pool APOBEC POOL | 53 A3F-B58-11 | 54 A3G-B58-196 | 57 A3G-B7-27 | 58 A3F-B7-43 | JACOBI HIV+ 113 A3G-A2-177 | 115 A3F-A2-194 | 116 A3F-A2-363 | 117 A3F-B58-159 | 118 A3F-B58-225 |
|---|---|---|---|---|---|---|---|---|---|---|
| BS 11/29/84 | 0 | 0 | 10 | 0 | 20 | 0 | 0 | 20 | 30 | 0 |
| AB 7/27/88 | 5 | 0 | 15 | 0 | 25 | 0 | 0 | 5 | 0 | 0 |
| AC 2/24/88 | 10 | 15 | 20 | 10 | 20 | 20 | 0 | 0 | 0 | 25 |
| CC 3/20/94 | 5 | 0 | 5 | 10 | 0 | 5 | 0 | 5 | 10 | 10 |
| AG 2/16/97 | 0 | 0 | 0 | 0 | 5 | 5 | 0 | 0 | 0 | 0 |
| BE 1/22/92 | 20 | 0 | 10 | 0 | 5 | 0 | 5 | 15 | 15 | 5 |
| AC 8/31/90 | 10 | 5 | 10 | 15 | 5 | 20 | 20 | 10 | 5 | 5 |
| AC 7/8/93 | 0 | 0 | 0 | 0 | 15 | 5 | 0 | 15 | 5 | 5 |
| KH 8/21/92 | 30 | 35 | 20 | 30 | 45 | 35 | 50 | 15 | 40 | 15 |
| AC 6/8/92 | 40 | 40 | 100 | 130 | 45 | 110 | 175 | 80 | 85 | 90 |
| AC 1/12/95 | 215 | 60 | 65 | 70 | 25 | 75 | 45 | 50 | 40 | 60 |
| AD 11/29/91 | 0 | 0 | 0 | 15 | 10 | 0 | 20 | 10 | 15 | 35 |
| BC 10/26/90 | 10 | 0 | 15 | 10 | 10 | 20 | 10 | 10 | 5 | 20 |
| AC 09/07/95 | 10 | 0 | 10 | 0 | 0 | 5 | 15 | 10 | 0 | 0 |
| SV 6/10/82 | 20 | 0 | 0 | 5 | 0 | 0 | 35 | 0 | 0 | 5 |
| TB 8/13/95 | 0 | 0 | 25 | 20 | 35 | 35 | 0 | 25 | 10 | 0 |
| TA 1/29/95 | 10 | 30 | 0 | 15 | 25 | 20 | 10 | 0 | 0 | 15 |
| CG 11/15/95 | 25 | 0 | 0 | 10 | 10 | 15 | 10 | 15 | 25 | 0 |
| CM 7/16/86 | 10 | 0 | 10 | 0 | 10 | 0 | 5 | 0 | 0 | 0 |
| CR 12/18/86 | 0 | 0 | 20 | 5 | 10 | 5 | 0 | 5 | 5 | 5 |
| DJ 6/29/95 | 0 | 0 | 0 | 5 | 10 | 0 | 0 | 0 | 0 | 0 |
| ST 3/5/87 | 45 | 0 | 15 | 50 | 10 | 5 | 0 | 0 | 0 | 0 |
| CM 12/3/88 | 1780 | 150 | 40 | 5 | 60 | 75 | 285 | 95 | 75 | 30 |
| CR1/1/87 | 10 | 0 | 15 | 5 | 15 | 5 | 5 | 0 | 5 | 20 |
| CR 9/10/91 | 0 | 0 | 5 | 0 | 0 | 0 | 0 | 35 | 0 | 0 |
| DF 4/28/94 | 0 | 0 | 0 | 0 | 0 | 0 | 0 | 0 | 0 | 0 |
| DC 6/27/86 | 240 | 210 | 355 | 300 | 255 | 415 | 545 | 205 | 310 | 0 |
| CT 6/21/89 | 20 | 25 | 15 | 60 | 35 | 50 | 70 | 40 | 35 | 380 |

| patient | pool APOBEC POOL | 53 A3F-B58-11 | 54 A3G-B58-196 | 57 A3G-B7-27 | 58 A3F-B7-43 | 113 A3G-A2-177 | 115 A3F-A2-194 | 116 A3F-A2-363 | 117 A3F-B58-159 | 118 A3F-B58-225 |
|---|---|---|---|---|---|---|---|---|---|---|
| YC 9/22/86 | 80 | 115 | 580 | 575 | 315 | 215 | 470 | 185 | 115 | 40 |
| CM 7/3/99 | 40 | 10 | 10 | 5 | 0 | 5 | 0 | 0 | 15 | 5 |
| TD 9/21/93 | 0 | 0 | 0 | 0 | 0 | 0 | 5 | 0 | 0 | 0 |
| DS 12/19/88 | 0 | 0 | 0 | 0 | 0 | 0 | 0 | 0 | 0 | 0 |
| DP 10/2/00 | 40 | 0 | 0 | 20 | 0 | 0 | 10 | 25 | 10 | 0 |
| ED 12/8/87 | 0 | 0 | 0 | 0 | 5 | 0 | 0 | 15 | 0 | 0 |
| EV 3/25/91 | 1135 | 45 | 0 | 5 | 5 | 10 | 30 | 15 | 10 | 10 |
| DM 5/20/90 | 5 | 0 | 30 | 35 | 35 | 30 | 30 | 5 | 0 | 15 |
| DL 10/10/89 | 0 | 0 | 0 | 0 | 0 | 0 | 0 | 0 | 0 | 0 |
| EJ 12/3/88 | 0 | 10 | 0 | 10 | 5 | 5 | 5 | 0 | 10 | 5 |
| DM 12 22 94 | 5 | 5 | 10 | 10 | 5 | 10 | 10 | 5 | 5 | 5 |
| ZK 6/14/96 | 0 | 10 | 0 | 10 | 5 | 10 | 30 | 0 | 20 | 20 |
| SR 11/16/90 | 5 | 5 | 40 | 20 | 10 | 20 | 0 | 30 | 20 | 20 |
| SR 11/24/83 | 0 | 0 | 0 | 0 | 0 | 0 | 0 | 0 | 0 | 0 |
| EJ 3/31/90 | 25 | 45 | 40 | 130 | 35 | 30 | 55 | 35 | 50 | 30 |
| FA 6/23/93 | 810 | 30 | 10 | 35 | 5 | 20 | 30 | 10 | 25 | 10 |
| DW 7/3/89 | 20 | 5 | 0 | 5 | 5 | 15 | 15 | 5 | 0 | 10 |
| ED 8/28/87 | 520 | 65 | 0 | 0 | 10 | 0 | 0 | 0 | 0 | 0 |
| FE 6/24/99 | 0 | 0 | 0 | 0 | 0 | 5 | 0 | 0 | 0 | 0 |
| FD 6/24/99 | 0 | 0 | 30 | 0 | 0 | 0 | 20 | 10 | 5 | 5 |
| FJ 3/31/90 | 0 | 10 | 0 | 0 | 0 | 5 | 0 | 0 | 0 | 20 |
| GF 1/24/98 | 0 | 0 | 0 | 0 | 5 | 0 | 0 | 5 | 5 | 20 |
| IS 9/4/96 | 0 | 0 | 0 | 0 | 0 | 15 | 45 | 30 | 40 | 0 |
| IN 2/01/97 | 5 | 15 | 65 | 25 | 40 | 10 | 5 | 5 | 0 | 30 |
| JL 7/8/97 | 120 | 0 | 10 | 0 | 0 | 20 | 5 | 5 | 5 | 0 |
| SR 11/16/90 | 0 | 10 | 0 | 10 | 0 | 5 | 5 | 5 | 15 | 10 |
| GR 03/30/91 | 5 | 0 | 10 | 0 | 5 | 5 | 5 | 0 | 5 | 15 |
| JB 4/29/01 | 25 | 5 | 0 | 5 | 5 | 5 | 35 | 10 | 5 | 5 |
| JA 8/6/93 | 15 | 5 | 5 | 5 | 20 | 0 | 0 | 5 | 0 | 0 |
| GC 7/31/91 | 0 | 0 | 0 | 0 | 0 | 0 | 0 | 0 | 0 | 0 |
| JM 2/11/92 | 315 | 0 | 10 | 0 | 0 | 0 | 10 | 0 | 0 | 0 |

FIG. 9B (Table 4 Cont.)

| patient | pool | 53 | 54 | 57 | 58 | 113 | 115 | 116 | 117 | 118 |
|---|---|---|---|---|---|---|---|---|---|---|
| | APOBEC POOL | A3F-B58-11 | A3G-B58-196 | A3G-B7-27 | A3F-B7-43 | A3G-A2-177 | A3F-A2-194 | A3F-A2-363 | A3F-B58-159 | A3F-B58-225 |
| IW 9/4/96 | 25 | 15 | 5 | 5 | 10 | 5 | 20 | 35 | 5 | 10 |
| JM 11/24/91 | 0 | 0 | 0 | 0 | 0 | 20 | 15 | 0 | 40 | 20 |
| KG 7/2/99 | 125 | 0 | 40 | 55 | 240 | 200 | 575 | 470 | 115 | 0 |
| JM 9/6/98 | 0 | 0 | 0 | 0 | 0 | 0 | 15 | 0 | 0 | 0 |
| JP 4/19/95 | 0 | 0 | 0 | 0 | 0 | 0 | 0 | 5 | 5 | 15 |
| JV 11/8/92 | 0 | 0 | 0 | 0 | 10 | 0 | 0 | 0 | 70 | 0 |
| SW 4/23/92 | 165 | 0 | 0 | 50 | 140 | 60 | 180 | 115 | 0 | 15 |
| JN 6/20/90 | 0 | 0 | 0 | 0 | 25 | 0 | 0 | 0 | 0 | 35 |
| JR 5/12/92 | 0 | 0 | 0 | 0 | 0 | 0 | 0 | 10 | 0 | 25 |
| SC 12/18/95 | 0 | 0 | 0 | 0 | 35 | 0 | 0 | 0 | 110 | 0 |
| WT 5/27/91 | 215 | 195 | 335 | 375 | 210 | 355 | 325 | 400 | 110 | 0 |
| JS 4/26/00 | 0 | 0 | 0 | 30 | 5 | 0 | 0 | 15 | 0 | 0 |
| JQ 11/10/98 | 130 | 0 | 145 | 0 | 20 | 160 | 135 | 245 | 135 | 70 |
| JW 9/10/91 | 10 | 0 | 0 | 0 | 0 | 0 | 0 | 0 | 0 | 5 |
| JM 12/21/86 | 5 | 0 | 0 | 20 | 0 | 0 | 5 | 0 | 5 | 5 |

FIG. 9C (Table 4 Cont.)

| patient | pool | 53 | 54 | 57 | 58 | 113 | 115 | 116 | 117 | 118 |
|---|---|---|---|---|---|---|---|---|---|---|
| | APOBEC POOL | A3F-B58-11 | A3G-B58-196 | A3G-B7-27 | A3F-B7-43 | A3G-A2-177 | A3F-A2-194 | A3F-A2-363 | A3F-B58-159 | A3F-B58-225 |
| EU JW 1/24/02 | 0 | 0 | 0 | 0 | 0 | 0 | 0 | 10 | 0 | 0 |
| EU AN 1/20/05 | 0 | 0 | 20 | 20 | 35 | 5 | 65 | 30 | 20 | 15 |
| EU KD 8/8/01 | 0 | 0 | 0 | 0 | 0 | 5 | 75 | 0 | 0 | 0 |
| EU TG 2/11/05 | 0 | 10 | 5 | 5 | 0 | 10 | 0 | 0 | 10 | 0 |
| EU MO 2/12/15 | 5 | 0 | 0 | 0 | 5 | 0 | 25 | 0 | 10 | 0 |
| EU MW 12/23/03 | 0 | 0 | 0 | 0 | 0 | 0 | 135 | 0 | 0 | 0 |
| EU KB 11/14/87 | 0 | 0 | 65 | 65 | 100 | 45 | 60 | 10 | 0 | 0 |
| EU JN 7/7/98 | 35 | 0 | 35 | 0 | 0 | 0 | 0 | 0 | 55 | 35 |

FIG. 10 (Table 5)

| ASBID | PID | APOBEC POOL RESPONSES |
|---|---|---|
| | | |
| OPTIONS | | |
| | | |
| AS00-00261 | 443 | 95 |
| AS01-21085 | 562 | 140 |
| AS02-03599 | 585 | 210 |
| AS03-05214 | 626 | 95 |
| AS04-22823 | 683 | 35 |
| AS04-05198 | 720 | 45 |
| AS03-02505 | 721 | 70 |
| AS03-13008 | 747 | 10 |
| AS03-13023 | 789 | 25 |
| AS02-16453 | 791 | 25 |
| AS02-17653 | 804 | 0 |
| AS03-04300 | 839 | 305 |
| AS01-05523 | 850 | 35 |
| | mean | 83.84615385 |
| | median | 45 |

FIG. 11 (Table 6)

| SCOPE | | |
|---|---|---|
| CONTROLLERS | | |
| AS04-14086 | 1016 | 25 |
| AS05-02245 | 1068 | 60 |
| AS04-10694 | 1071 | 0 |
| AS04-20779 | 1095 | 10 |
| AS07-06903 | 1119 | 20 |
| AS06-03532 | 1133 | 285 |
| AS05-12637 | 1143 | 55 |
| AS07-05814 | 1155 | 15 |
| AS06-11807 | 1157 | 35 |
| AS07-05918 | 1179 | 10 |
| AS07-06915 | 1185 | 5 |
| AS02-19388 | 1504 | 65 |
| AS07-00270 | 1508 | 15 |
| AS07-01673 | 1516 | 60 |
| AS05-13311 | 1525 | 180 |
| AS07-01037 | 1531 | 0 |
| AS05-13281 | 1536 | 0 |
| AS07-04897 | 1545 | 10 |
| AS06-13641 | 1564 | 10 |
| | mean | 45.26315789 |
| | median | 15 |

FIG. 12 (Table 7)

| HAART | SCOPE | |
|---|---|---|
| AS02-18892 | 2003 | 0 |
| AS03-03134 | 2006 | 45 |
| AS02-19411 | 2013 | 0 |
| AS02-21830 | 2017 | 50 |
| AS01-19362 | 2039 | 10 |
| AS02-17210 | 2048 | 25 |
| AS03-07023 | 2049 | 145 |
| AS04-04084 | 2050 | 60 |
| AS04-05653 | 2055 | 0 |
| AS03-07431 | 2056 | 250 |
| AS03-05020 | 2058 | 30 |
| AS03-08863 | 2063 | 95 |
| AS02-26155 | 2072 | 45 |
| AS02-20536 | 2085 | 50 |
| AS03-00592 | 2087 | 5 |
| AS02-26521 | 2089 | 120 |
| AS01-17870 | 2096 | 50 |
| AS01-04348 | 2100 | 25 |
| AS04-14261 | 2102 | 30 |
| AS02-19660 | 6049 | 45 |
| | mean | 54 |
| | median | 45 |

FIG. 13 (Table 8)

| SCOPE | | |
|---|---|---|
| VIRMEIC | | |
| AS02-01930 | 3001 | 5 |
| AS03-01851 | 3016 | 20 |
| AS07-00685 | 3025 | 0 |
| AS06-10997 | 3026 | 10 |
| AS05-10066 | 3049 | 90 |
| AS03-21788 | 3051 | 10 |
| AS05-04834 | 3058 | 5 |
| AS05-02614 | 3059 | 15 |
| AS07-08409 | 3073 | 10 |
| AS02-15331 | 3076 | 20 |
| AS02-21575 | 3079 | 45 |
| AS04-12109 | 3086 | 25 |
| AS07-04852 | 3092 | 15 |
| AS05-07073 | 3101 | 0 |
| AS03-00309 | 3119 | 0 |
| AS03-11145 | 3130 | 95 |
| AS03-22280 | 3158 | 10 |
| AS04-12717 | 3183 | 10 |
| AS03-14192 | 6014 | 5 |
| AS05-16553 | 6028 | 25 |
| AS04-05819 | 6043 | 290 |
| | | |
| | mean | 33.57142857 |
| | median | 10 |

FIG. 14 (Table 9)

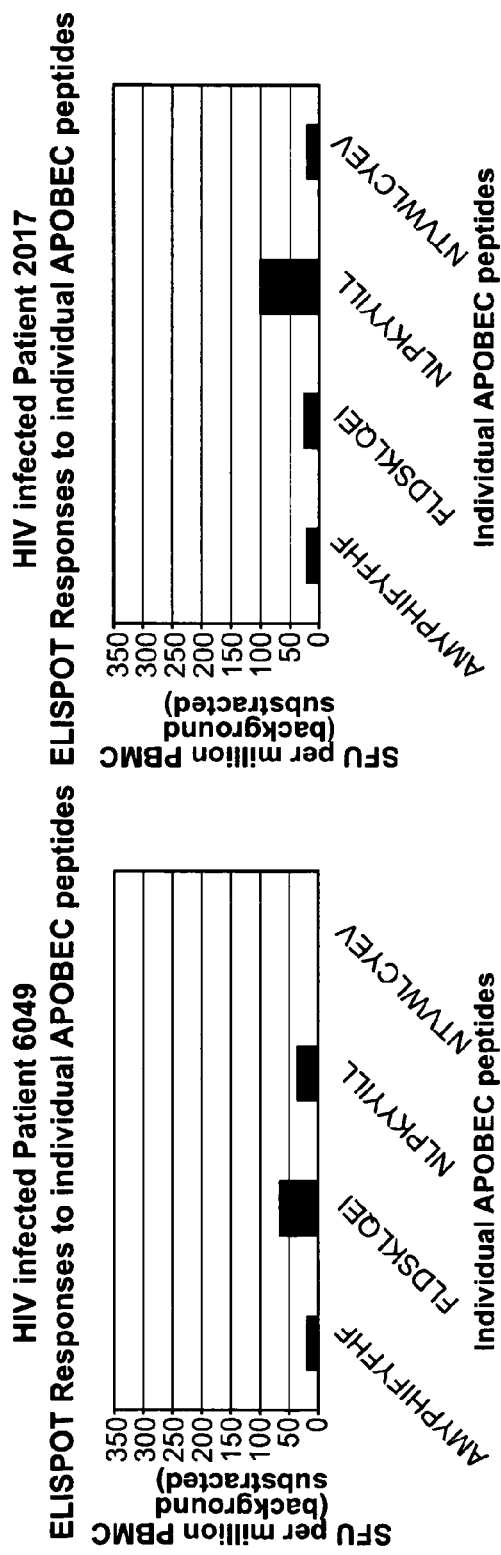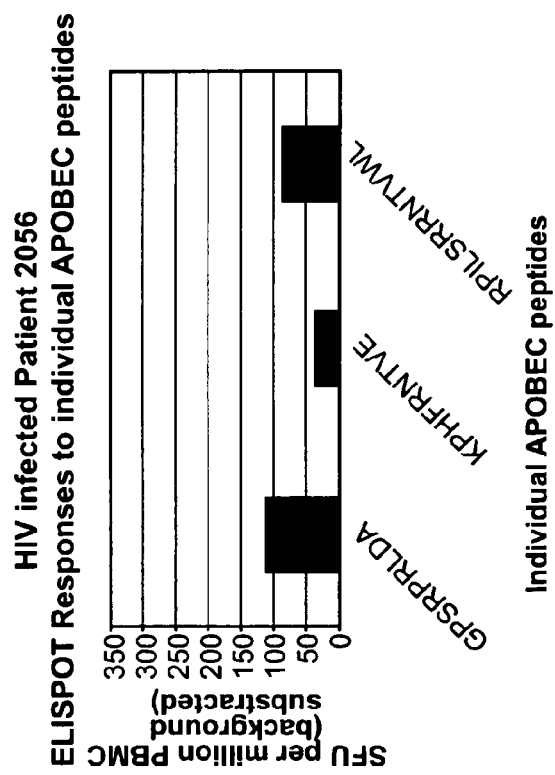
FIG. 15 (Cont.)

METHOD OF INDUCING A T LYMPHOCYTE RESPONSE USING T-CELL IMMUNOGENS DERIVED FROM ANTI-VIRAL PROTEINS

CROSS-REFERENCE

This application is a continuation of U.S. patent application Ser. No. 13/121,106, filed Jul. 1, 2011, now U.S. Pat. No. 9,084,762, which is a national stage filing under 35 U.S.C. §371 of PCT/US2009/005381, filed Sep. 28, 2009, which claims the benefit of U.S. Provisional Patent Application No. 61/101,590, filed Sep. 30, 2008, each of which applications is incorporated herein by reference in its entirety.

BACKGROUND

A number of host cell proteins have evolved that inhibit retroviral infection, retroelement mobilization, and/or replication. Examples of such proteins include apolipoprotein BmRNA-editing catalytic (APOBEC) polypeptides, tetherin polypeptides and tripartite motif-containing 5 (TRIM5) polypeptides. Certain retroviruses, e.g., HIV, have evolved proteins which antagonize the anti-viral effects of one or more of these proteins. For example, HIV Vpu has been shown to antagonize the anti-viral activity of the tetherin polypeptide, CD317, and HIV Vif has been shown to antagonize the antiviral activity of APOBEC 3G and 3F polypeptides. It has been shown that Vif triggers proteosomal degradation of APOBEC via a physical interaction with APOBEC 3G.

Despite recent advances in HIV research, the World Health Organization (WHO) estimates that currently between 30 and 36 million people worldwide are living with HIV/AIDS and that approximately 2.7 million people were newly infected in the last year (UNAIDS 2008 Report on the global AIDS epidemic). There is a need in the art for methods useful in the treatment and/or prophylaxis of HIV infection.

LITERATURE

Goila-Gaur and Strebel (2008) *Retrovirology* 5:51; Neil et al. (2008) *Nature* 451:425-431; Santiago et al. (2008) *Science* 321:1343-1346; Hundemer et al. (2006) *Exp. Hematol.* 34(4):486-96; U.S. Patent Publication No. 2002/0164743, U.S. Patent Publication No. 2004/0009951, U.S. Patent Publication No. 2004/0115184, U.S. Patent Publication No. 2005/0054073, U.S. Patent Publication No. 2006/0246568.

SUMMARY OF THE INVENTION

Isolated polypeptides related to endogenous anti-viral polypeptides; and compositions, including immunogenic compositions, comprising a subject isolated polypeptide are disclosed herein. A subject isolated polypeptide comprises an amino acid sequence having substantial amino acid sequence identity to a contiguous stretch of amino acids of one or more endogenous anti-viral polypeptides, wherein the endogenous anti-viral polypeptides are polypeptides subject to proteolytic degradation as a result of the activity of one or more viral proteins. Also provided are diagnostic and treatment methods using the subject isolated polypeptides and compositions.

In one embodiment, an immunogenic composition is disclosed, wherein the immunogenic composition includes a) an isolated polypeptide including an amino acid sequence having at least about 85% amino acid sequence identity to a contiguous stretch of from about 6 amino acids to about 60 amino acids of an endogenous polypeptide that interacts with a retroviral polypeptide, wherein interaction of the endogenous polypeptide with the retroviral polypeptide results in proteolytic degradation of the endogenous polypeptide; and b) a pharmaceutically acceptable carrier.

In one embodiment of the immunogenic composition, the isolated polypeptide does not comprise a full-length amino acid sequence as set forth in any one of SEQ ID NOs: 1-10 and 23-24. In one embodiment of the immunogenic composition, the isolated polypeptide has a length of about 6 to about 150 amino acids. In one embodiment of the immunogenic composition, the endogenous polypeptide is an apolipoprotein B mRNA-editing catalytic (APOBEC) polypeptide, a tetherin polypeptide, or a TRIM5 polypeptide. In one embodiment where the endogenous polypeptide is an apolipoprotein B mRNA-editing catalytic (APOBEC) polypeptide, a tetherin polypeptide, or a TRIM5 polypeptide, the endogenous polypeptide is an APOBEC polypeptide. In one embodiment of the immunogenic composition, the isolated polypeptide includes an amino acid sequence having at least about 85% amino acid sequence identity to any one of SEQ ID NOs:1-24. In one embodiment of the immunogenic composition, the isolated polypeptide includes an amino acid sequence set forth in any one of SEQ ID NOs:1-24. The immunogenic composition can be formulated for parenteral administration. The immunogenic composition can also be formulated for administration to a mucosal tissue. In one embodiment of the immunogenic composition, the immunogenic composition also includes an adjuvant. Where the immunogenic composition also includes an adjuvant, the adjuvant can include aluminum hydroxide, MF59, or monophosphoryl lipidA.

In another embodiment, an immunogenic composition is described, wherein the immunogenic composition includes a nucleic acid including a nucleotide sequence encoding a polypeptide, wherein said polypeptide includes an amino acid sequence having at least about 85% amino acid sequence identity to a contiguous stretch of from about 6 amino acids to about 60 amino acids of an endogenous polypeptide that interacts with a retroviral polypeptide, wherein interaction of the endogenous polypeptide with the retroviral polypeptide results in proteolytic degradation of the endogenous polypeptide.

In one embodiment of the immunogenic composition including a nucleic acid, the polypeptide does not comprise a full-length amino acid sequence as set forth in any one of SEQ ID NOs: 1-10 and 23-24. In one embodiment of the immunogenic composition including a nucleic acid, the polypeptide has a length of about 6 to about 150 amino acids. In one embodiment of the immunogenic composition including a nucleic acid, the endogenous polypeptide is an apolipoprotein B mRNA-editing catalytic (APOBEC) polypeptide, a tetherin polypeptide, or a TRIM5 polypeptide. In one embodiment of the immunogenic composition including a nucleic acid, the endogenous polypeptide is an APOBEC polypeptide. In one embodiment of the immunogenic composition including a nucleic acid, the encoded polypeptide includes an amino acid sequence having at least about 85% amino acid sequence identity to any one of SEQ ID NOs: 1-24. In one embodiment of the immunogenic composition including a nucleic acid, the encoded polypeptide includes an amino acid sequence set forth in any one of SEQ ID NOs:1-24. The immunogenic composition including a nucleic acid can be formulated for parenteral administration.

The immunogenic composition including a nucleic acid can also be formulated for administration to a mucosal tissue.

In one embodiment of the immunogenic composition including a nucleic acid, the nucleic acid is a recombinant vector. In one embodiment, the recombinant vector is a recombinant viral vector.

In another embodiment, a method of inducing a T lymphocyte response in an individual to a host cell infected with or at risk of infection with a pathogenic virus is described, wherein the method includes administering to the individual one of the immunogenic compositions described above. In one embodiment of the method of inducing a T lymphocyte response in an individual to a host cell infected with or at risk of infection with a pathogenic virus, the T lymphocyte response includes a CD8+ T cell response or a CD4+ T cell response. In one embodiment of the method of inducing a T lymphocyte response in an individual to a host cell infected with or at risk of infection with a pathogenic virus, the T lymphocyte response includes a mucosal T lymphocyte response. In one embodiment of the method of inducing a T lymphocyte response in an individual to a host cell infected with or at risk of infection with a pathogenic virus, the pathogenic virus is a human immunodeficiency virus. In one embodiment of the method of inducing a T lymphocyte response in an individual to a host cell infected with or at risk of infection with a pathogenic virus, the individual has not been infected with the pathogenic virus. In another embodiment of the method of inducing a T lymphocyte response in an individual to a host cell infected with or at risk of infection with a pathogenic virus, the individual has been infected with the pathogenic virus.

In another embodiment, an isolated polypeptide is described, wherein the isolated polypeptide includes an amino acid sequence having at least about 85% amino acid sequence identity to a contiguous stretch of from about 6 amino acids to about 60 amino acids of an endogenous polypeptide that interacts with a retroviral polypeptide, wherein interaction of the endogenous polypeptide with the retroviral polypeptide results in proteolytic degradation of the endogenous polypeptide. In one embodiment, the isolated polypeptide does not include a full-length amino acid sequence as set forth in any one of SEQ ID NOs: 1-10 and 23-24. In one embodiment, the isolated polypeptide has a length of about 6 to about 150 amino acids. In one embodiment of the isolated polypeptide, the endogenous polypeptide is an apolipoprotein B mRNA-editing catalytic (APOBEC) polypeptide, a tetherin polypeptide, a TRIM5 polypeptide. In one embodiment of the isolated polypeptide, the endogenous polypeptide is an APOBEC polypeptide. In one embodiment, the isolated polypeptide includes an amino acid sequence having at least about 85% amino acid sequence identity to any one of SEQ ID NOs:1-24. In one embodiment, the isolated polypeptide includes an amino acid sequence set forth in any one of SEQ ID NOs:1-24. In another embodiment, a composition is described, wherein the composition includes an isolated polypeptide as described above.

In another embodiment, a method of generating a population of CD8+ T cells specific for a polypeptide is described, wherein the method includes contacting a population of unstimulated CD8+ T cells in vitro with an isolated polypeptide in association with an antigen-presenting platform, wherein said isolated polypeptide includes an amino acid sequence having at least about 85% amino acid sequence identity to a contiguous stretch of from about 6 amino acids to about 60 amino acids of an endogenous polypeptide that interacts with a retroviral polypeptide, wherein interaction of the endogenous polypeptide with the retroviral polypeptide results in proteolytic degradation of the endogenous polypeptide, and wherein said contacting provides for production of a population of CD8+ T cells specific for said synthetic polypeptide. In one embodiment of the method of generating a population of CD8+ T cells specific for a polypeptide, the isolated polypeptide does not comprise a full-length amino acid sequence as set forth in any one of SEQ ID NOs: 1-10 and 23-24. In one embodiment of the method of generating a population of CD8+ T cells specific for a polypeptide, the isolated polypeptide has a length of about 6 to about 150 amino acids.

In another embodiment, a method of generating a population of CD4+ T cells specific for a polypeptide is described, wherein the method includes contacting a population of unstimulated CD4+ T cells in vitro with an isolated polypeptide in association with an antigen-presenting platform, wherein said isolated polypeptide includes an amino acid sequence having at least about 85% amino acid sequence identity to a contiguous stretch of from about 6 amino acids to about 60 amino acids of an endogenous polypeptide that interacts with a retroviral polypeptide, wherein interaction of the endogenous polypeptide with the retroviral polypeptide results in proteolytic degradation of the endogenous polypeptide, and wherein said contacting provides for production of a population of CD4+ T cells specific for said synthetic polypeptide. In one embodiment of the method of generating a population of CD4+ T cells specific for a polypeptide, the isolated polypeptide does not comprise a full-length amino acid sequence as set forth in any one of SEQ ID NOs: 1-10 and 23-24. In one embodiment of the method of generating a population of CD4+ T cells specific for a polypeptide, the isolated polypeptide has a length of about 6 to about 150 amino acids.

BRIEF DESCRIPTION OF THE DRAWINGS

FIG. 3 provides a table showing patient characteristics and APOBEC polypeptide pool responses based on an enzyme-linked immunospot (ELISPOT) data.

FIG. 7 provides a table showing T cell responses to an APOBEC polypeptide pool responses based on ELISPOT data for 7 Long Term Non-Progressor (LTNP) patients and 1 chronic progressor. Units are SFU/10$^6$ PBMC. Bold highlighting=values above background.

FIGS. 8A and 8B provide a table showing T cell responses for patients including Controllers (individuals who are able to maintain low to undetectable levels of HIV in the absence of any therapy), HAART treated individuals with undetectable plasma HIV RNA levels, and Viremics (individuals with higher levels of viremia). Responses to 12 different APOBEC polypeptides are shown. Results are ELISPOT assay results. Units are SFU/10$^6$ PBMC. Bold highlighting=values above background.

FIGS. 9A-C provide a table showing T cell responses for chronically infected children. Responses to both pooled and individual APOBEC polypeptides are shown. Results are ELISPOT assay results. Units are SFU/10$^6$ PBMC. Bold highlighting=values above background.

FIG. 10 provides a table showing T cell responses for exposed but uninfected children. Responses to both pooled and individual APOBEC polypeptides are shown. Results are ELISPOT assay results. Units are SFU/10$^6$ PBMC. Bold highlighting=values above background.

FIG. 11 provides a table showing T cell responses for the Options cohort of patients (a cohort of primary HIV-1 infected subjects). These subjects are HIV-1 infected and enrolled within 6 months of infection, and then followed longitudinally over time. Some members receive antiretroviral treatment, while others remain with drug therapy. Responses to pooled APOBEC polypeptides are shown. Results are ELISPOT assay results. Units are SFU/10$^6$ PBMC. Bold highlighting=values above background.

FIG. 12 provides a table showing T cell responses for Controllers (individuals who are able to maintain low to undetectable levels of HIV in the absence of any therapy). Responses to pooled APOBEC polypeptides are shown. Results are ELISPOT assay results. Units are SFU/10$^6$ PBMC. Bold highlighting=values above background.

FIG. 13 provides a table showing T cell responses for HAART treated individuals with undetectable plasma HIV RNA levels. Responses to pooled APOBEC polypeptides are shown. Results are ELISPOT assay results. Units are SFU/10$^6$ PBMC. Bold highlighting=values above background.

FIG. 14 provides a table showing T cell responses for Viremics (individuals with higher levels of viremia). Responses to pooled APOBEC polypeptides are shown. Results are ELISPOT assay results. Units are SFU/10$^6$ PBMC. Bold highlighting=values above background.

DEFINITIONS

Figure 1:
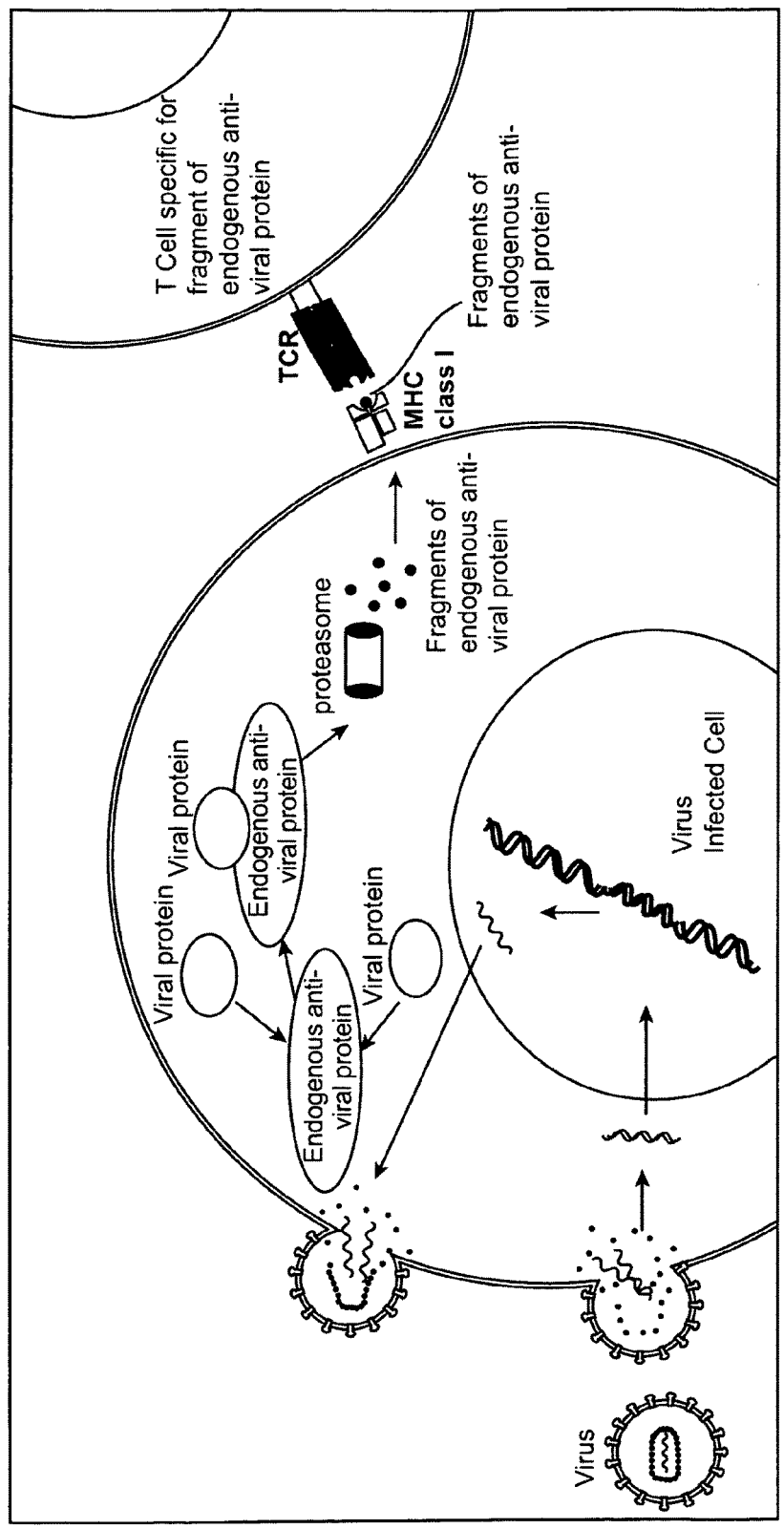
FIG. 1 provides a proposed model showing viral protein-mediated proteolytic processing of an endogenous anti-viral polypeptide, subsequent presentation of a fragment of the endogenous anti-viral polypeptide on the surface of a virus-infected cell, and recognition of the displayed fragment by a T cell.
Figure 2:
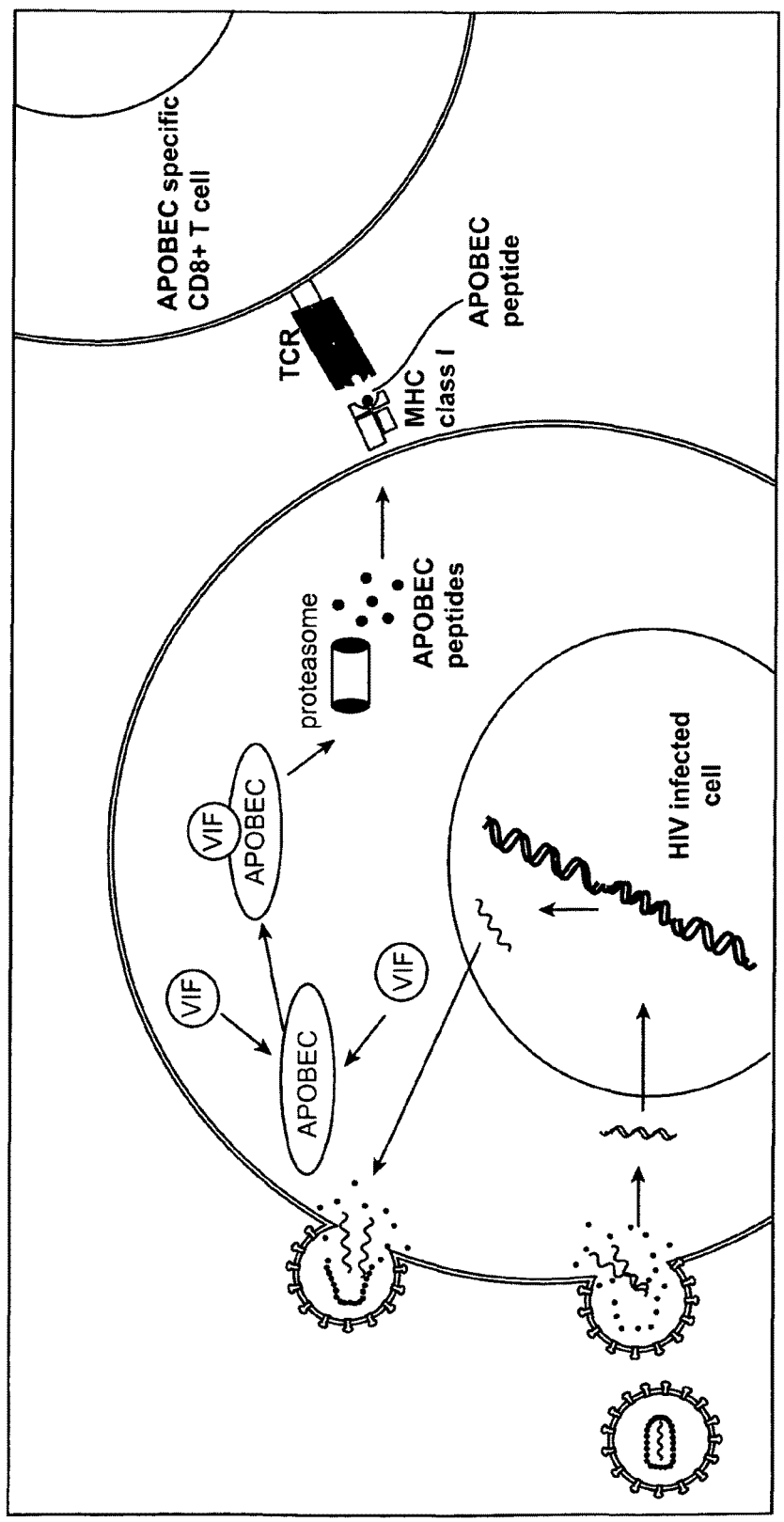
FIG. 2 provides a proposed model of one specific embodiment of the model set forth in FIG. 1.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as CD4$^+$ T lymphocytes, CD8$^+$ T lymphocytes, glial cells, macrophages, tumor cells, peripheral blood mononuclear cells (PBMC), and the like. The term "biological sample" encompasses a clinical sample, and also includes cells in culture, cell supernatants, tissue samples, organs, bone marrow, blood, plasma, serum, cerebrospinal fluid, and the like.

The term "retrovirus" is well known in the art, and includes single-stranded, positive sense, enveloped RNA viruses that include, e.g., the genus *Gammaretrovirus* (e.g., murine mammary tumor virus); the genus *Epsilonretrovirus*; the genus *Alpharetrovirus* (e.g., avian leukosis virus); the genus *Betaretrovirus*; the genus *Deltaretrovirus* (e.g., bovine leukemia virus; human T-lymphotrophic virus (HTLV)); the genus *Lentivirus*; and the genus *Spumavirus*. The term "*lentivirus*," as used herein, refers to a genus of viruses of the Retroviridae family, and includes human immunodeficiency virus-1 (HIV-1); human immunodeficiency virus-2 (HIV-2); simian immunodeficiency virus. (SIV); and feline immunodeficiency virus (FIV).

"Gene delivery vehicle" refers to a construct which is capable of delivering, and, within some embodiments expressing, one or more gene(s) or nucleotide sequence(s) of interest in a host cell. Representative examples of such vehicles include viral vectors, nucleic acid expression vectors, naked DNA, and certain eukaryotic cells (e.g., producer cells).

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct-the expression thereof. Thus, for example, intervening untranslated yet transcribed sequences can be present between a promoter sequence and the coding sequence and the promoter sequence can still be considered "operably linked" to the coding sequence.

The terms "polypeptide," "peptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. NH$_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243 (1969), 3552-59 is used.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells. An isolated polypeptide will in some embodiments be synthetic. "Synthetic polypeptides" are assembled from amino acids, and are chemically synthesized in vitro, e.g., cell-free chemical synthesis, using procedures known to those skilled in the art.

By "purified" is meant a compound of interest (e.g., a polypeptide) has been separated from components that accompany it in nature. "Purified" can also be used to refer to a compound of interest separated from components that can accompany it during manufacture (e.g., in chemical synthesis). In some embodiments, a compound is substantially pure when it is at least 50% to 60%, by weight, free from organic molecules with which it is naturally associated or with which it is associated during manufacture. In some embodiments, the preparation is at least 75%, at least 90%, at least 95%, or at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample having a compound that binds an antibody of interest. Purity can be measured by any appropriate method, e.g., chromatography, mass spectroscopy, high performance liquid chromatography analysis, etc.

The term "endogenous," when used in reference to a polypeptide, means that which is naturally produced (e.g., by an unmodified mammalian or human cell). As used herein, the terms "endogenous" and "native" are interchangeable.

The term "substantially similar" as used in the context of nucleic acid or amino acid sequence identity refers to two or more sequences which have at least about 50%, at least about 60%, at least about 70%, at least about 75%, at least about 80%, at least about 85%, at least about 90%, at least about 95%, at least about 98%, at least about 99%, or 100% sequence identity.

As used herein "% sequence identity" is determined using the EMBOSS Pairwise Alignment Algorithms tool available from The European Bioinformatics Institute (EMBL-EBI), which is part of the European Molecular Biology Laboratory (EMBL). This tool is accessible at the website located by placing "www." in front of "ebi.ac.uk/Tools/emboss/align/". This tool utilizes the Needleman-Wunsch global alignment algorithm (Needleman, S. B. and Wunsch, C. D. (1970) J. Mol. Biol. 48, 443-453; Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley. Default settings are utilized which include Gap Open: 10.0 and Gap Extend 0.5. The default matrix "Blosum62" is utilized for amino acid sequences and the default matrix "DNAfull" is utilized for nucleic acid sequences.

An "antigen" is defined herein to include any substance that may be specifically bound by an antibody molecule or a T cell antigen receptor. An "immunogen" is an antigen that is capable of initiating lymphocyte activation resulting in an antigen-specific immune response.

By "epitope" is meant a site on an antigen to which specific B cells and/or T cells respond. The term is also used interchangeably with "antigenic determinant" or "antigenic determinant site." B cell epitope sites on proteins, polysaccharides, or other biopolymers may be composed of moieties from different parts of the macromolecule that have been brought together by folding. Epitopes of this kind are referred to as conformational or discontinuous epitopes, since the site is composed of segments of the polymer that are discontinuous in the linear sequence but are continuous in the folded conformation(s). Epitopes that are composed of single segments of biopolymers or other molecules are termed continuous or linear epitopes. T cell epitopes are generally linear peptides. Antibodies that recognize the same epitope can be identified in a simple immunoassay showing the ability of one antibody to block the binding of another antibody to a target antigen.

The terms "subject," "individual," "host," and "patient" are used interchangeably herein to refer to a mammal, including, but not limited to, murines (rats, mice), felines, non-human primates (e.g., simians), humans, canines, ungulates, etc.

The terms "treatment," "treating," "treat," and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a synthetic polypeptide" includes a plurality of such synthetic polypeptides and reference to "the immunogenic composition" includes reference to one or more immunogenic compositions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Isolated polypeptides related to endogenous anti-viral polypeptides; and compositions, including immunogenic compositions, comprising a subject isolated polypeptide are disclosed herein. A subject isolated polypeptide comprises an amino acid sequence having substantial amino acid sequence identity to a contiguous stretch of amino acids of one or more endogenous anti-viral polypeptides, wherein the endogenous anti-viral polypeptides are polypeptides that are subject to proteolytic degradation as a result of the activity of one or more viral proteins. For convenience, the disclosed isolated polypeptides are referred to herein as "Polypeptides derived from Endogenous Anti-viral Polypeptides" or PEAPs.

The present disclosure provides a nucleic acid comprising a nucleotide sequence encoding a subject PEAP; and compositions, including immunogenic compositions, comprising a subject nucleic acid.

The present disclosure provides immunogenic compositions comprising a nucleic acid comprising a nucleotide sequence encoding a subject PEAP. A subject immunogenic composition is useful for stimulating a specific T cell immune response to a retrovirus infected cell, e.g., a human immunodeficiency virus (HIV)-infected cell. Epitope(s) displayed by a subject isolated polypeptide stimulate or enhance a T cell immune response to the epitope(s). Where the epitopes are also present on the surface of a retrovirus-infected cell, a T cell response to the retrovirus-infected cell also occurs. A "T cell immune response" includes one or more of: 1) an increase in the number and/or activity of CD4$^+$ T cells specific for the epitope; 2) an increase in the number and/or activity (e.g., cytotoxicity) of CD8$^+$ T cells specific for the epitope; and 3) secretion of cytokines or chemokines that induce or are indicative of a T cell immune response. Cytokines or chemokines that induce or are indicative of a T cell immune response include, but are not limited to, interferon-gamma (IFN-$\gamma$), IL-2, and tumor necrosis factor-alpha (TNF-$\alpha$). T cell immune responses that are stimulated with a disclosed immunogenic composition include a mucosal T cell immune response and a systemic T cell immune response.

A subject immunogenic composition can be formulated in any of a variety of ways, including a formulation suitable for intravenous administration, subcutaneous administration, or other parenteral route of administration; a formulation suitable for administration to a mucosal tissue; and the like. The present disclosure provides pharmaceutical formulations comprising a subject immunogenic composition.

The present disclosure further provides polypeptide compositions that are suitable for use in monitoring a patient's response to treatment for a *lentivirus* infection (e.g., an HIV infection). Thus, the present disclosure further provides methods for monitoring a patient's response to treatment for a *lentivirus* infection (e.g., an HIV infection).

Polypeptides

The present disclosure provides isolated polypeptides, wherein the isolated polypeptides comprise an amino acid sequence having substantial amino acid sequence identity to a contiguous stretch of amino acids of one or more endogenous anti-viral polypeptides, where the endogenous anti-viral polypeptides are polypeptides that are subject to proteolytic degradation as a result of the activity of one or more viral proteins. A subject isolated polypeptide is referred to herein as a "Polypeptide derived from an Endogenous Anti-viral Polypeptide" or PEAP. In some embodiments, a subject PEAP is synthetic (e.g., chemically synthesized). Thus, the present disclosure provides a synthetic PEAP. In the discussion that follows, the term "subject PEAP," or simply "PEAP" is used; however, it should be understood that the following discussion applies equally to a "subject synthetic PEAP."

A subject PEAP can be from 6 amino acids in length up to the length of a naturally-occurring endogenous anti-viral polypeptide described herein, e.g., a PEAP can be 6 amino acids (aa), 7 aa, 8 aa, 9 aa, 10 aa, 11 aa, 12-15 aa, 15-20 aa, 20-25 aa, 25-30 aa, 30-40 aa, 40-50 aa, 50-100 aa, or longer than 100 amino acids, e.g., 100 aa to 150 aa, 150 aa to 200 aa.

The present disclosure also provides compositions comprising a subject PEAP. A subject PEAP finds use in, e.g., generating immunogenic compositions (e.g., for enhancing an immune response in an individual to a PEAP and/or an endogenous polypeptide having an amino acid sequence substantially similar to that of a subject PEAP; or for enhancing an immune response in an individual to a retrovirus-infected cell); monitoring patient response to therapy, e.g., therapy for a retrovirus infection; staging a disease; detecting a disease; and for generating CD8$^+$ T cells for adoptive transfer methods.

As indicated above, a subject isolated polypeptide comprises an amino acid sequence having substantial amino acid sequence identity to a contiguous stretch of amino acids of one or more endogenous anti-viral polypeptides, where the endogenous anti-viral polypeptides are polypeptides that are subject to proteolytic degradation as a result of the activity of one or more viral proteins. Endogenous anti-viral polypeptides that are subject to proteolytic degradation as a result of the activity of one or more viral proteins (e.g., one or more human immunodeficiency virus-encoded proteins) include, e.g., APOBEC polypeptides, a tetherin polypeptides and a TRIM5 polypeptides.

APOBEC Polypeptides

In some embodiments, a subject PEAP comprises an amino acid sequence that has substantial amino acid sequence identity to a contiguous stretch of amino acids of one or more apoliprotein B mRNA-editing catalytic (APOBEC) polypeptides. APOBEC polypeptides are a group of cytidine deaminases, which in humans include AICDA, APOBEC1, APOBEC2, APOBEC4 and a series of seven polypeptides encoded by APOBEC3 genes. APOBEC3 polypeptides include APOBEC3A, APOBEC3B, APOBEC3C, APOBEC3DE, APOBEC3F, APOBEC3G and APOBEC3H (Goila-Gaur and Strebel (2008) *Retrovirology* 5:51).

In some embodiments, a subject PEAP comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence of an endogenous APOBEC polypeptide. As used herein, the term "endogenous APOBEC polypeptide" includes known variants of APOBEC polypeptides. For example, known APOBEC3G variants include APOBEC3G polypeptides having an H186R and/or C97A mutation.

In some embodiments, a subject PEAP comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence of an APOBEC polypeptide; and has a length of 6 amino acids (aa), 7 aa, 8 aa, 9 aa, 10 aa, 11 aa, from 12 aa to 15 aa, from 15 to 20 aa, from 20 to 25 aa, from 25 to 30 aa, from 30 to 40 aa, from 40 to 50 aa, from 50 to 100 aa, from 100 aa to 150 aa, or from 150 aa to 200 aa.

APOBEC polypeptides include polypeptides having the amino acid sequences set forth in GenBank Accession Nos.:

```
U72891 (APOBEC1): (SEQ ID NO: 1:
MTSEKGPSTGDPTLRRRIEPWEFDVFYDPRELRKEACLLYEIKWGMSRKI
WRSSGKNTTNHVEVNFIKKFTSERDFHPSMSCSITWFLSWSPCWECSQAI
REFLSRHPGVTLVIYVARLFWHMDQQNRQGLRDLVNSGVTIQIMRASEYY
HCWRNFVNYPPGDEAHWPQYPPLWMMLYALELHCIILSLPPCLKISRRWQ
NHLTFFRLHLQNCHYQTIPPHILLATGLIHPSVAWR)

AB040430 (activation-induced cytidine deaminase:
AICDA): (SEQ ID NO: 2:
MDSLLMNRRKFLYQFKNVRWAKGRRETYLCYVVKRRDSATSFSLDFGYLR
NKNGCHVELLFLRYISDWDLDPGRCYRVTWFTSWSPCYDCARHVADFLRG
NPNLSLRIFTARLYFCEDRKAEPEGLRRLHRAGVQIAIMTFKDYFYCWNT
FVENHERTFKAWEGLHENSVRLSRQLRRILLPLYEVDDLRDAFRTLGL);

U03891 (APOBEC3A): (SEQ ID NO: 3:
MEASPASGPRHLMDPHIFTSNFNNGIGRHKTYLCYEVERLDNGTSVKMDQ
HRGFLHNQAKNLLCGFYGRHAELRFLDLVPSLQLDPAQIYRVTWFISWSP
CFSWGCAGEVRAFLQENTHVRLRIFAARIYDYDPLYKEALQMLRDAGAQV
SIMTYDEFKHCWDTFVDHQGCPFQPWDGLDEHSQALSGRLRAILQNQGN);

NM_004900 (APOBEC3B): (SEQ ID NO: 4:
MNPQIRNPMERMYRDTFYDNFENEPILYGRSYTWLCYEVKIKRGRSNLLW
DTGVFRGQVYFKPQYHAEMCFLSWFCGNQLPAYKCFQITWFVSWTPCPDC
VAKLAEFLSEHPNVTLTISAARLYYYWERDYRRALCRLSQAGARVTIMDY
EEFAYCWENFVYNEGQQFMPWYKFDENYAFLHRTLKEILRYLMDPDTFTF
NFNNDPLVLRRRQTYLCYEVERLDNGTWVLMDQHMGFLCNEAKNLLCGFY
GRHAELRFLDLVPSLQLDPAQIYRVTWFISWSPCFSWGCAGEVRAFLQEN
THVRLRIFAARIYDYDPLYKEALQMLRDAGAQVSIMTYDEFEYCWDTFVY
RQGCPFQPWDGLEEHSQALSGRLRAILQNQGN);

AF165520 (APOBEC3C): (SEQ ID NO: 5:
MNPQIRNPMKAMYPGTFYFQFKNLWEANDRNETWLCFTVEGIKRRSVVSW
KTGVFRNQVDSETHCHAERCFLSWFCDDILSPNTKYQVTWYTSWSPCPDC
AGEVAEFLARHSNVNLTIFTARLYYFQYPCYQEGLRSLSQEGVAVEIMDY
EDFKYCWENFVYNDNEPFKPWEGIKNQLSTSEKKATGESPVRGLPGPHGL
SPLASCSCCTGLPSTLDPLCFCLVILSPSWPQGHSTVLPCLTASSSLFQT
LPAEAPFCLHGYPSTPTDPVPPACVPLTWLEPSPQHNQILLNSC);

NM_152426 (APOBEC3DE): (SEQ ID NO: 6:
MNPQIRNPMERMYRDTFYDNFENEPILYGRSYTWLCYEVKIKRGRSNLLW
DTGVFRGPVLPKRQSNHRQEVYFRFENHAEMCFLSWFCGNRLPANRREQI
TWFVSWNPCLPCVVKVTKFLAEHPNVTLTISAARLYYYRDRDWRWVLLRL
HKAGARVKIMDYEDFAYCWENFVCNEGQPFMPWYKFDDNYASLHRTLKEI
LRNPMEAMYPHIFYFHFKNLLKACGRNESWLCFTMEVTKHHSAVFRKRGV
FRNQVDPETHCHAERCFLSWFCDDILSPNTNYEVTWYTSWSPCPECAGEV
AEFLARHSNVNLTIFTARLCYFWDTDYQEGLCSLSQEGASVKIMGYKDFV
SCWKNFVYSDDEPFKPWKGLQTNFRLLKRRLREILQ);

BC038808 (APOBEC3F): (SEQ ID NO: 7:
MKPHFRNTVERMYRDTFSYNFYNRPILSRRNTVWLCYEVKTKGPSRPRLD
AKIFRGQVYSQPEHHAEMCFLSWFCGNQLPAYKCFQITWFVSWTPCPDCV
AKLAEFLSEHPNVTLTISAARLYYYWERDYRRALCRLSQAGARVKIMDDE
EFAYCWENFVYSEGQPFMPWYKFDDNYAFLHRTLKEILRNPMEAMYPHIF
YFHFKNLRKAYGRNESWLCFTMEVVKHHSPISWKRGVFRNQVDPETHCHA
ERCFLSWFCDDILSPNTNYEVTWYTSWSPCPECAGEVAEFLARHSNVNLT
IFTARLYYFWDTDYQEGLRSLSQEGASVEIMGYKDFKYCWENFVYNDDEP
FKPWKGLKYNFLFLDSKLQEILE);

AF182420 (APOBEC3G): (SEQ ID NO: 8:
MKPHFRNTVERMYRDTFSYNFYNRPILSRRNTVWLCYEVKTKGPSRPPLD
AKIFRGQVYSELKYHPEMRFFHWFSKWRKLHRDQEYEVTWYISWSPCTKC
TRDMATFLAEDPKVTLTIFVARLYYFWDPDYQEALRSLCQKRDGPRATMK
IMNYDEFQHCWSKFVYSQRELFEPWNNLPKYYILLHIMLGEILRHSMDPP
TFTFNFNNEPWVRGRHETYLCYEVERMHNDTWVLLNQRRGFLCNQAPHKH
GELEGRHAELCFLDVIPFWKLDLDQDYRVTCFTSWSPCFSCAQEMAKFIS
KNKHVSLCIFTARIYDDQGRCQEGLRTLAEAGAKISIMTYSEEKHCWDTF
VDHQGCPFQPWDGLDEHSQDLSGRLRAILQNQEN);

BC069023 (APOBEC3H): (SEQ ID NO: 9:
MALLTAETFRLQFNNKRRLRRPYYPRKALLCYQLTPQNGSTPTRGYFENK
KKCHAEICFINEIKSMGLDETQCYQVTCYLTWSPCSSCAWELVDFIKAHD
HLNLGIFASRLYYHWCKPQQKGLRLLCGSQVPVEVMGFPEFADCWENFVD
HEKPLSFNPYKMLEELDKNSRAIKRRLERIKS);

BC02171 1 (APOBEC4) (SEQ ID NO: 10:
MEPIYEEYLANHGTIVKPYYWLSFSLDCSNCPYHIRTGEEARVSLTEFCQ
IFGFPYGTTFPQTKHLTFYELKTSSGSLVQKGHASSCTGNYIHPESMLFE
MNGYLDSAIYNNDSIRHIILYSNNSPCNEANHCCISKMYNFLITYPGITL
SIYFSQLYHTEMDFPASAWNREALRSLASLWPRVVLSPISGGIWHSVLHS
FISGVSGSHVFQPILTGRALADRHNAYEINAITGVKPYFTDVLLQTKRNP
NTKAQEALESYPLNNAFPGQFFQMPSGQLQPNLPPDLRAPVVFVLVPLRD
LPPMHMGQNPNKPRNIVRHLNMPQMSFQETKDLGRLPTGRSVEIVEITEQ
FASSKEADEKKKKKGKK).
```

In some embodiments, a subject PEAP comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in one or more of SEQ ID NOs: 1-10.

In some embodiments, a subject PEAP comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in one or more of SEQ ID NOs: 1-10; and has a length of 6 amino acids (aa), 7 aa, 8 aa, 9 aa, 10 aa, 11 aa, from 12 aa to 15 aa, from 15 to 20 aa, from 20 to 25 aa, from 25 to 30 aa, from 30 to 40 aa, from 40 to 50 aa, from 50 to 100 aa, from 100 aa to 150 aa, or from 150 aa to 200 aa.

In some embodiments, a subject PEAP does not comprise the full length amino acid sequence disclosed in any one of SEQ ID NOs: 1-10. In one such embodiment, the subject immunogenic composition does not comprise a polypeptide having an amino acid sequence that is at least about 60% identical to the amino acid sequence set forth in SEQ ID NO: 2 or an immunogenic fragment thereof.

As indicated above, in some embodiments, a subject PEAP comprises an amino acid sequence having substantial amino acid sequence identity to a contiguous stretch of amino acids of an APOBEC3F polypeptide. For example, in some embodiments, a subject PEAP comprises about 6, 7, 8, 9, 10 or 11 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:11:

```
                                    (SEQ ID NO: 11)
AMYPHIFYFHF.
```

In some embodiments, a subject PEAP comprises about 6, 7, 8, 9, 10 or 11 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:11; and has a length of from about 6 amino acids to about 25 amino acids (e.g., from about 6 aa to about 11 aa, from about 11 aa to about 15 aa, from about 15 aa to about 20 aa, or from about 20 aa to about 25 aa).

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO: 12:

```
                                    (SEQ ID NO: 12)
FLDSKLQEI.
```

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO: 12; and has a length of from about 6 amino acids to about 25 amino acids (e.g., from about 6 aa to about 9 aa, from about 9 aa to about 12 aa, from about 12 aa to about 15 aa, from about 15 aa to about 20 aa, or from about 20 aa to about 25 aa).

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:13:

```
                                    (SEQ ID NO: 13)
FVYSEGQPF.
```

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:13; and has a length of from about 6 amino acids to about 25 amino acids (e.g., from about 6 aa to about 9 aa, from about 9 aa to about 12 aa, from about 12 aa to about 15 aa, from about 15 aa to about 20 aa, or from about 20 aa to about 25 aa).

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:14:

```
                                    (SEQ ID NO: 14)
VKHHSPVSW.
```

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:14; and has a length of from about 6 amino acids to about 25 amino acids (e.g., from about 6 aa to about 9 aa, from about 9 aa to about 12 aa, from about 12 aa to about 15 aa, from about 15 aa to about 20 aa, or from about 20 aa to about 25 aa).

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:15:

RMYRDTFSY. (SEQ ID NO: 15)

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:15; and has a length of from about 6 amino acids to about 25 amino acids (e.g., from about 6 aa to about 9 aa, from about 9 aa to about 12 aa, from about 12 aa to about 15 aa, from about 15 aa to about 20 aa, or from about 20 aa to about 25 aa).

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:16:

GPSRPRLDA. (SEQ ID NO: 16)

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:16; and has a length of from about 6 amino acids to about 25 amino acids (e.g., from about 6 aa to about 9 aa, from about 9 aa to about 12 aa, from about 12 aa to about 15 aa, from about 15 aa to about 20 aa, or from about 20 aa to about 25 aa).

In some embodiments, a subject PEAP comprises an amino acid sequence having substantial amino acid sequence identity to a contiguous stretch of amino acids of an APOBEC3G polypeptide.

In one example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:17:

NLPKYYILL. (SEQ ID NO: 17)

In one example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:17; and has a length of from about 6 amino acids to about 25 amino acids (e.g., from about 6 aa to about 9 aa, from about 9 aa to about 12 aa, from about 12 aa to about 15 aa, from about 15 aa to about 20 aa, or from about 20 aa to about 25 aa).

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:18:

NTVWLCYEV. (SEQ ID NO: 18)

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:18; and has a length of from about 6 amino acids to about 25 amino acids (e.g., from about 6 aa to about 9 aa, from about 9 aa to about 12 aa, from about 12 aa to about 15 aa, from about 15 aa to about 20 aa, or from about 20 aa to about 25 aa).

In another example, a subject PEAP comprises about 6, 7, 8, 9, 10 or 11 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:19:

RHSMDPPTFTF. (SEQ ID NO: 19)

In another example, a subject PEAP comprises about 6, 7, 8, 9, 10 or 11 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:19; and has a length of from about 6 amino acids to about 25 amino acids (e.g., from about 6 aa to about 9 aa, from about 9 aa to about 11 aa, from about 11 aa to about 15 aa, from about 15 aa to about 20 aa, or from about 20 aa to about 25 aa).

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:20:

```
                                          (SEQ ID NO: 20)
           FVYSQRELF.
```

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:20; and has a length of from about 6 amino acids to about 25 amino acids (e.g., from about 6 aa to about 9 aa, from about 9 aa to about 12 aa, from about 12 aa to about 15 aa, from about 15 aa to about 20 aa, or from about 20 aa to about 25 aa).

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:21:

```
                                          (SEQ ID NO: 21)
           KPHFRNTVE.
```

In another example, a subject PEAP comprises about 6, 7, 8 or 9 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:21; and has a length of from about 6 amino acids to about 25 amino acids (e.g., from about 6 aa to about 9 aa, from about 9 aa to about 12 aa, from about 12 aa to about 15 aa, from about 15 aa to about 20 aa, or from about 20 aa to about 25 aa).

In another example, a subject PEAP comprises about 6, 7, 8, 9, 10, 11 or 12 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:22:

```
                                          (SEQ ID NO: 22)
           RPILSRRNTVWL.
```

In another example, a subject PEAP comprises about 6, 7, 8, 9, 10, 11 or 12 contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:22; and has a length of from about 6 amino acids to about 25 amino acids (e.g., from about 6 aa to about 9 aa, from about 9 aa to about 12 aa, from about 12 aa to about 15 aa, from about 15 aa to about 20 aa, or from about 20 aa to about 25 aa).

In some embodiments, a subject PEAP comprises one or more of the following amino acid sequences:

```
                                          (SEQ ID NO: 11)
           AMYPHIFYFHF;

(SEQ ID NO: 12)
           FLDSKLQEI;

(SEQ ID NO: 13)
           FVYSEGQPF;

(SEQ ID NO: 14)
           VKHHSPVSW;

(SEQ ID NO: 15)
           RMYRDTFSY;

(SEQ ID NO: 16)
           GPSRPRLDA;

(SEQ ID NO: 17)
           NLPKYYILL;

(SEQ ID NO: 18)
           NTVWLCYEV;

(SEQ ID NO: 19)
           RHSMDPPTFTF;

(SEQ ID NO: 20)
           FVYSQRELF;

(SEQ ID NO: 21)
           KPHFRNTVE;
           and (SEQ ID NO: 22)
           RPILSRRNTVWL.
```

Tetherin Polypeptides

In some embodiments, a subject PEAP comprises an amino acid sequence having substantial amino acid sequence identity to a contiguous stretch of amino acids of one or more tetherin polypeptides. Tetherin polypeptides have been shown to inhibit the release of retroviral particles (Neil et al. (2008) Nature 451:425-431).

In some embodiments, a subject PEAP comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence of an endogenous tetherin polypeptide. As used herein, the term "endogenous tetherin polypeptide" includes known variants of tetherin polypeptides.

Tetherin polypeptides include polypeptides having the amino acid sequence set forth in GenBank Accession No: NM_004335 (BST2, a.k.a., CD317, a.k.a, HM1.24) (SEQ ID NO:23:

```
MASTSYDYCRVPMEDGDKRCKLLLGIGILVLLIIVILGVPLIIF

TIKANSEACRDGLRAVMECRNVTHLLQQELTEAQKGFQDVEAQAATCNHT

VMALMASLDAEKAQGQKKVEELEGEITTLNHKLQDASAEVERLRRENQVL

SVRIADKKYYPSSQDSSSAAAPQLLIVLLGLSALLQ).
```

As such, in some embodiments, a subject PEAP comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO: 23.

In some embodiments, a subject PEAP comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO: 23; and has a length of 6 amino acids (aa), 7 aa, 8 aa, 9 aa, 10 aa, 11 aa, from 12 aa to 15 aa, from 15 to 20 aa, from 20 to 25 aa, from 25 to 30 aa, from 30 to 40 aa, from 40 to 50 aa, from 50 to 100 aa, from 100 aa to 150 aa, or from 150 aa to 200 aa.

In some embodiments, a subject PEAP does not comprise the full length amino acid sequence set forth in SEQ ID NO:23.

TRIM5 Polypeptides

In some embodiments, a subject PEAP comprises an amino acid sequence having substantial amino acid sequence identity to a contiguous stretch of amino acids of one or more TRIM5 (tripartite motif-containing 5) polypeptides.

In some embodiments, a subject PEAP comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence of an endogenous TRIM5 polypeptide. As used herein, the term "endogenous TRIM5 polypeptide" includes known variants of TRIM5 polypeptides.

TRIM5 polypeptides include polypeptides having the amino acid sequence set forth in GenBank Accession No: AF220025 (TRIM5, a.k.a., RNF88, a.k.a., TRIM5alpha) (SEQ ID NO:24:

MASGILVNVKEEVTCPICLELLTQPLSLDCGHSFCQACLTANHKKSMLDK

GESSCPVCRISYQPENIRPNRHVANIVEKLREVKLSPEGQKVDHCARHGE

KLLLFCQEDGKVICWLCERSQEHRGHHTFLTEEVAREYQVKLQAALEMLR

QKQQEAEELEADIREEKASWKTQIQYDKTNVLADFEQLRDILDWEESNEL

QNLEKEEEDILKSLINSETEMVQQTQSLRELISDLEHRLQGSVMELLQGV

DGVIKRTENVTLKKPETFPKNQRRVFRAPDLKGMLEVFRELTDVRRYWVD

VTVAPNNISCAVISEDKRQVSSPKPQIIYGARGTRYQTFVNFNYCTGILG

SQSITSGKHYWEVDVSKKTAWILGVCAGFQPDAMCNIEKNENYQPKYGYW

VIGLEEGVKCSAFQDSSFHTPSVPFIVPLSVIICPDRVGVFLDYEACTVS

FFNITNHGFLIYKFSHCSFSQPVFPYLNPRKCGVPMTLCSPSS).

As such, in some embodiments, a subject PEAP comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:24.

In some embodiments, a subject PEAP comprises from about 6, 7, 8, 9, 10, 11, 12, 13-15, 15-17, 17-20, from 20 to 25, from 25 to 50, from 50 to 75, from 75 to 100, or from 100 to 150, or more, contiguous amino acids of an amino acid sequence having at least about 50%, at least about 60%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:24; and has a length of 6 amino acids (aa), 7 aa, 8 aa, 9 aa, 10 aa, 11 aa, from 12 aa to 15 aa, from 15 to 20 aa, from 20 to 25 aa, from 25 to 30 aa, from 30 to 40 aa, from 40 to 50 aa, from 50 to 100 aa, from 100 aa to 150 aa, or from 150 aa to 200 aa.

In some embodiments, a subject PEAP does not comprise the full length amino acid sequence disclosed in SEQ ID NO:24.

A subject PEAP can be from 6 amino acids in length up to the length of a naturally-occurring endogenous anti-viral polypeptide described herein, e.g., a PEAP can be 6 amino acids (aa), 7 aa, 8 aa, 9 aa, 10 aa, 11 aa, 12-15 aa, 15-20 aa, 20-25 aa, 25-30 aa, 30-40 aa, 40-50 aa, 50-100 aa, or longer than 100 amino acids, e.g., 100 aa to 150 aa, 150 aa to 200 aa.

A subject PEAP can be in the form of a fusion protein, e.g., a fusion protein comprising one or more of the isolated polypeptides described above covalently linked to a heterologous protein, where the heterologous protein is also referred to as a "fusion partner." In some embodiments, the fusion partner is attached to the N-terminus of an isolated polypeptide disclosed herein, e.g., NH2-fusion partner-isolated polypeptide-COOH. In other embodiments, the fusion partner is attached to the C-terminus of the synthetic polypeptide, e.g., NH2-isolated polypeptide-fusion partner-COOH. In other embodiments, the fusion partner is internal to the synthetic polypeptide, e.g., $NH_2$-PEAP1-FP-PEAP2-COOH, where FP is a fusion partner, and PEAP1 and PEAP2 are N-terminal and C-terminal regions, respectively, of a PEAP.

Suitable fusion partners include, but are not limited to, immunological tags such as epitope tags, including, but not limited to, hemagglutinin, FLAG, myc, and the like; proteins that provide for a detectable signal, including, but not limited to, fluorescent proteins, enzymes (e.g., β-galactosidase, luciferase, horse radish peroxidase, alkaline phosphatase, etc.), and the like; polypeptides that facilitate purification or isolation of the fusion protein, e.g., metal ion binding polypeptides such as 6His tags, glutathione-S-transferase, and the like; polypeptides that provide for subcellular localization; and polypeptides that provide for secretion from a cell. Fusion partners that provide for a detectable signal are also referred to as "reporters." In some embodiments, a fusion partner is an immunomodulatory polypeptide other than a PEAP, e.g., an antigen, a cytokine, etc.

Multimerized PEAPs

In some embodiments, a subject PEAP is multimerized, e.g., two or more PEAPs are linked in tandem. Multimers include dimers, trimers, tetramers, pentamers, etc. Monomeric PEAPs can be linked to one another directly or via a linker. Thus, in some embodiments, a PEAP has the formula $(X_1—(Y)_{0-40}—X_2—(Y)_{0-40})_n$, where $X_1$ and $X_2$ are PEAPs, Y is a linker, and n is an integer from 1 to about 10 (e.g., n=1, 2, 3, 4, 5, 6, 7, 8, 9, or 10). Where a linker is used, Y is one or more amino acids, or other linking groups. $X_1$ and $X_2$ can be the same or different, e.g., can have the same amino acid sequence, or can differ from one another in amino acid sequence. Thus, e.g., an PEAP can have the formula $X_1—(Y)_{0-40}—X_2$. e.g., where the PEAP is a dimer. As another example, a PEAP can have the formula $X_1—(Y)_{0-40}—X_2—(Y)_{0-40}—X_3$, e.g., where the PEAP is a trimer.

In some embodiments, the PEAP multimer is a homopolymer, e.g., the individual PEAP peptides in a subject multimer all have the same amino acid sequence. In other embodiments, the PEAP multimer is a heteropolymer, e.g., two or more different PEAPS are multimerized. As a non-limiting example, a PEAP multimer can comprise a first PEAP and at least a second PEAP, where the first and the second PEAPS are two different PEAPS comprising the amino acid sequence of any one of SEQ ID NOs:11-22, where the two or more different PEAPS each has a length of from 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, or from about 40 amino acids to about 50 amino acids.

Where Y is a spacer peptide, it is generally of a flexible nature, although other chemical linkages are not excluded. Currently, it is contemplated that the most useful linker sequences will generally be peptides of between about 2 and about 40 amino acids in length, e.g., from about 2 amino acids to about 10 amino acids, from about 10 amino acids to about 20 amino acids, or from about 6 amino acids to about 25 amino acids in length. These linkers are generally produced by using synthetic, linker-encoding oligonucleotides to couple the proteins. Peptide linkers with a degree of flexibility will generally be used. The linking peptides may have virtually any amino acid sequence, bearing in mind that the preferred linkers will have a sequence that results in a generally flexible peptide. The use of small amino acids, such as glycine and alanine, are of use in creating a flexible peptide. Exemplary peptide linkers include $(Gly)_{2-40}$, $(Ser)_{2-40}$, and $(Ala)_{2-40}$. The creation of such sequences is routine to those of skill in the art. Many different linkers are commercially available and are considered suitable for use according to the disclosed embodiments. However, any flexible linker generally between about 2 amino acids and about 40 amino acids, e.g., from about 6 amino acids to about 10 amino acids in length may be used. Linkers may have virtually any sequence that results in a generally flexible peptide.

Linkages for homo- or hetero-polymers or for coupling to carriers can be provided in a variety of ways. For example, cysteine residues can be added at both the amino- and carboxyl-termini, where the peptides are covalently bonded via controlled oxidation of the cysteine residues. Also useful are a large number of heterobifunctional agents which generate a disulfide link at one functional group end and a peptide link at the other, including N-succidimidyl-3-(2-pyridyldithio) proprionate (SPDP). This reagent creates a disulfide linkage between itself and a cysteine residue in one protein and an amide linkage through the amino on a lysine or other free amino group in the other. A variety of such disulfide/amide forming agents is known. See, for example, Immun. Rev. 62:185 (1982). Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl)cyclohexane-1-carboxylic acid and the like. The carboxyl groups can be activated by combining them with succinimide or 1-hydroxy-2-nitro-4-sulfonic acid, sodium salt. A particularly preferred coupling agent is succinimidyl 4-(N-maleimidomethyl)cyclohexane-1-carboxylate (SMCC). Of course, it will be understood that linkage should not substantially interfere with either of the linked groups to function for its intended use, e.g., as an immunogen.

Carriers

In some embodiments, a subject PEAP is linked to a carrier. The term "linked," as used herein interchangeably with the term "coupled," refers to proximately associated, e.g., the PEAP and the carrier are in close spatial proximity. In some embodiments, the linkage is a covalent linkage. In other embodiments, the linkage is a non-covalent linkage. In some embodiments, the PEAP is linked directly to the carrier. In other embodiments, the PEAP is linked indirectly, e.g., via a linker molecule.

Examples of suitable carriers include large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; inactivated virus particles; inactivated bacterial toxins such as toxoid from diphtheria, tetanus, cholera, leukotoxin molecules; liposomes; inactivated bacteria; dendritic cells; and the like. Carriers are described in further detail below.

Suitable carriers are well known in the art, and include, e.g., thyroglobulin, albumins such as human serum albumin, tetanus toxoid; Diphtheria toxoid; polyamino acids such as poly(D-lysine:D-glutamic acid); VP6 polypeptides of rotaviruses; influenza virus hemagglutinin, influenza virus nucleoprotein; hepatitis B virus core protein, hepatitis B virus surface antigen; purified protein derivative (PPD) of tuberculin from *Mycobacterium tuberculosis*; inactivated *Pseudomonas aeruginosa* exotoxin A (toxin A); Keyhole Limpet Hemocyanin (KLH); filamentous hemagglutinin (FHA) of *Bordetella pertussis*; T helper cell (Th) epitopes of tetanus toxoid (TT) and *Bacillus* Calmette-Guerin (BCG) cell wall; recombinant 10 kDa, 19 kDa and 30-32 kDa proteins from *M. leprae* or from *M. tuberculosis*, or any combination of these proteins; and the like. See, e.g., U.S. Pat. No. 6,447,778 for a discussion of carriers and methods of conjugating peptides to carriers.

*Pseudomonas aeruginosa* exotoxin A (toxin A) has been used effectively as a carrier in conjugate vaccines. *Pseudomonas aeruginosa* exotoxin A may be purified from the supernatant of fermentor-grown cultures of *Pseudomonas aeruginosa* PA 103. Toxin A has been classified as a superantigen based upon results in animals. Toxin A can be completely and irreversibly detoxified by covalent coupling to adipic acid dihydrazide (ADH), a 4 carbon spacer molecule. This step destroys the ADPR-transferase activity of the toxin molecule, hence rendering it nontoxic. The non-reacted hydrazide group can be used to covalently couple a polypeptide to toxin A. Toxin A may also be coupled to a polypeptide using a carbodiimide reagent.

PPD-peptide conjugates are conveniently prepared with glutaraldehyde as coupling agent. See, e.g., Rubinstein et al. (1995) AIDS 9:243-51.

The methods by which a subject polypeptide is conjugated with a carrier include disulfide linkages through a C terminal peptide cysteine linkage, coupling with glutaraldehyde solution for two hours, coupling with tyrosine, or coupling with water soluble carbodiimide.

In some embodiments, a subject PEAP is lipidated. Lipidation increases a cytotoxic T cell (CTL) response to the peptide that is linked to the lipid. The lipid residue, such as palmitic acid or the like, is attached to the amino terminus of the peptide. The lipid can be attached directly to the peptide, or, indirectly via a linkage, such as a Ser-Ser, Gly, Gly-Gly, Ser linkage or the like. As another example, *E. coli* lipoprotein, such as tripalmitoyl-S-glycerylcysteinyl-seryl-serine ($P_3$ CSS), can be used to prime specific CTL when covalently attached to the peptide. See, Deres et al., *Nature* 342:561-564 (1989). A subject PEAP can be conjugated with uncharged fatty acid residues of different chain lengths and degrees of unsaturation, ranging from acetic to stearic acid as well as to negatively charged succinyl residues via the appropriate carboxylic acid anhydrides. See, e.g., U.S. Pat. No. 6,419,931.

A subject PEAP can be conjugated directly or indirectly, e.g., via a linker molecule, to a carrier. A wide variety of linker molecules are known in the art and can be used in the conjugates. The linkage from the peptide to the carrier may be through a peptide reactive side chain, or the N- or C-terminus of the peptide. A linker may be an organic, inorganic, or semi-organic molecule, and may be a polymer of an organic molecule, an inorganic molecule, or a co-polymer comprising both inorganic and organic molecules.

If present, the linker molecules are generally of sufficient length to permit the PEAP and a linked carrier to allow some flexible movement between the PEAP and the carrier. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Compositions

The present disclosure provides compositions comprising one or more subject PEAPs. Compositions comprising one or more subject PEAPs can include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like. In some embodiments, as described in more detail below, a subject PEAP composition is an immunogenic composition. In other embodiments, as described in more detail below, a subject PEAP composition is a pharmaceutical composition, e.g., a composition comprising a PEAP and a pharmaceutically acceptable excipient.

In some embodiments, a composition comprises a single type (or "species") of PEAP, e.g., in some embodiments, the PEAPs in a subject composition all comprise substantially the same amino acid sequence. In other embodiments, a subject immunogenic composition comprises two or more different PEAPs, e.g., the composition comprises a population of PEAPs, the members of which population can differ in amino acid sequence. A composition can comprise from two to about 20 different PEAPs, e.g., a subject composition can comprise two, three, four, five, six, seven, eight, nine, ten, 11-15, or 15-20 different PEAPs, each having an amino acid that differs from the amino acid sequences of the other PEAPs. For example, in some embodiments, a composition comprises a first PEAP having a first amino acid sequence; and at least a second PEAP having a second amino acid sequence, where the second amino acid sequence differs from the first amino acid sequence. As another example, in some embodiments, a composition comprises a first PEAP having a first amino acid sequence; a second PEAP having a second amino acid sequence, where the second amino acid sequence differs from the first amino acid sequence; and at least a third PEAP having a third amino acid sequence, where the third amino acid sequence differs from both the first and the second amino acid sequences. In other embodiments, a subject composition comprises a multimerized PEAP, as described above.

Production of PEAPs

A subject PEAP can be produced in a number of ways, including, e.g., by chemical synthesis, where the PEAP is a "synthetic" polypeptide; by isolation and purification from a naturally-occurring source; and by recombinant means, where the PEAP is a "recombinant" polypeptide. Recombinant means for producing a subject PEAP are well known in the art, and involve genetically modifying a host cell with a polynucleotide comprising a nucleotide sequence encoding a subject PEAP, culturing the host cell in vitro under conditions and for a suitable time such that the PEAP is produced by the genetically modified cell, and isolating the PEAP produced by the genetically modified cell. Methods of chemically synthesizing a polypeptide are known in the art and can be used to synthesize a subject PEAP. For example, standard 9H-fluoren-9-yl-methoxycarbonyl (FMoc) chemistry can be used. See, e.g., "Fmoc Solid Phase Peptide Synthesis: A Practical Approach" W. C. Chan and P. D. White, eds. (2000) Oxford Univ. Press.

Pharmaceutical Compositions

The present disclosure provides a pharmaceutical composition comprising a subject PEAP, the composition comprising a subject PEAP and a pharmaceutically acceptable excipient.

A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents.

A subject PEAP pharmaceutical composition can be prepared by dissolving, suspending or emulsifying a subject PEAP in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Immunogenic Compositions Comprising a PEAP

The present disclosure contemplates immunogenic compositions comprising a subject PEAP. A subject immunogenic composition can comprise a subject PEAP that comprises one or more T cell epitopes that, when presented on the surface of a retrovirus-infected cell, induce a T cell immune response specific for a retrovirus-infected cell, e.g., a human immunodeficiency virus (HIV)-infected cell. A "T cell immune response" includes one or more of: 1) an increase in the number and/or activity of $CD4^+$ T cells specific for the PEAP epitope; 2) an increase in the number and/or activity of $CD8^+$ T cells specific for the PEAP epitope; and 3) secretion of cytokines or chemokines that induce or are indicative of a T cell immune response. Cytokines that induce or are indicative of a T cell immune response include, but are not limited to, interferon-gamma (IFN-γ), IL-2, IL-17, and tumor necrosis factor-alpha (TNF-α).

In certain embodiments, administration of a subject immunogenic composition results in T cell mediated killing of a retrovirus-infected cell, e.g. an HIV infected cell, via specific T cell recognition of a PEAP or fragment thereof on the surface of a retrovirus-infected cell. In other embodiments, administration of a disclosed immunogenic composition results in T cell mediated killing of a retrovirus-infected cell, e.g. an HIV infected cell, via cross-reactivity of a T cell specific for a PEAP or fragment thereof with a fragment of an endogenous anti-viral polypeptide presented on the surface of a retrovirus-infected cell.

In one embodiment, a subject immunogenic composition does not comprise a polypeptide having an amino acid sequence that is at least about 60% identical to the amino acid sequence set forth in SEQ ID NO: 2 or an immunogenic fragment thereof.

In certain embodiments, a subject immunogenic composition comprises a peptide comprising the amino acid sequence of any one of SEQ ID NOs:11-22, where the peptide has a length of from 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, or from about 40 amino acids to about 50 amino acids.

In certain embodiments, a subject immunogenic composition comprises two or more different PEAPS. For example, in some embodiments, a subject immunogenic composition comprises 2, 3, 4, 5, 6, 7, 8, 9, 10, 11, or 12 different PEAPS, where each PEAP comprises a peptide comprising the amino acid sequence of any one of SEQ ID NOs:11-22, where the peptide has a length of from 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, or from about 40 amino acids to about 50 amino acids.

In some embodiments, a subject immunogenic composition comprises a multimerized PEAP, as described above.

A subject immunogenic composition can be formulated in a number of ways, as described in more detail below. In one example, a subject immunogenic composition comprises single species of PEAP, e.g., the immunogenic composition comprises a population of PEAPs, substantially all of which have the same amino acid sequence. In other examples, a subject immunogenic composition comprises two or more different PEAPs, i.e., the immunogenic composition comprises a population of PEAPs, wherein two or more of the members differ in amino acid sequence. A subject immunogenic composition can comprise from two to about 20 different PEAPs, e.g., a subject immunogenic composition can comprise two, three, four, five, six, seven, eight, nine, ten, 11-15, or 15-20 different PEAPs, each having an amino acid that differs from the amino acid sequences of the other PEAPs. For example, in some embodiments, a subject immunogenic composition comprises a first PEAP having a first amino acid sequence; and at least a second PEAP having a second amino acid sequence, where the second amino acid sequence differs from the first amino acid sequence. As another example, in some embodiments, a subject immunogenic composition comprises a first PEAP having a first amino acid sequence; a second PEAP having a second amino acid sequence, where the second amino acid sequence differs from the first amino acid sequence; and at least a third PEAP having a third amino acid sequence, where the third amino acid sequence differs from both the first and the second amino acid sequences. In other embodiments, a subject immunogenic composition comprises a multimerized PEAP, as described above.

Adjuvants

In some embodiments, a subject immunogenic composition comprises a subject PEAP, and an adjuvant. Examples of suitable adjuvants that can be used in humans include, but are not necessarily limited to, alum, aluminum phosphate, aluminum hydroxide, MF59 (4.3% w/v squalene, 0.5% w/v Tween 80, 0.5% w/v Span 85), CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For veterinary applications including but not limited to animal experimentation, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (COP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic antigen.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in *Vaccine design: the subunit and adjuvant approach*, eds. Powell & Newman, Plenum Press 1995), containing 5% Squalene, 0.5% Tween 80 (polyoxyethylene sorbitan mono-oleate), and 0.5% Span 85 (sorbitan trioleate) (optionally containing muramyl tri-peptide covalently linked to dipalmitoyl phosphatidylethanolamine (MTP-PE)) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), e.g., MPL+CWS (DETOX™); (2) saponin adjuvants, such as QS21 or STIMULON™ (Cambridge Bioscience, Worcester, Mass.) can be used or particles generated therefrom such as ISCOMs (immunostimulating complexes), which ISCOMS may be devoid of additional detergent e.g. WO00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum e.g. WO00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs [Krieg *Vaccine* 2000, 19, 618-622; Krieg *Curr Opin Mol Ther* 2001 3:15-24; Roman et al., *Nat. Med.*, 1997, 3, 849-854; Weiner et al., *PNAS USA*, 1997, 94, 10833-10837; Davis et al, *J. Immunol*, 1998, 160, 870-876; Chu et al., *J. Exp. Med*, 1997, 186, 1623-1631; Lipford et al, *Eur. J. Immunol.*, 1997, 27, 2340-2344; Moldoveanu et al., *Vaccine*, 1988, 16, 1216-1224, Krieg et al., *Nature*, 1995, 374, 546-549; Klinman et al., *PNAS USA*, 1996, 93, 2879-2883; Ballas et al, *J. Immunol*, 1996, 157, 1840-1845; Cowdery et al, *J. Immunol*, 1996, 156, 4570-4575; Halpern et al, *Cell Immunol*, 1996, 167, 72-78; Yamamoto et al, *Jpn. J. Cancer Res.*, 1988, 79, 866-873; Stacey et al, *J. Immunol.*, 1996, 157, 2116-2122; Messina et al, *J. Immunol*, 1991, 147, 1759-1764; Yi et al, *J. Immunol*, 1996, 157, 4918-4925; Yi et al, 0.1 Immunol, 1996, 157, 5394-5402; Yi et al, *J. Immunol*, 1998, 160, 4755-4761; and Yi et al, *J. Immunol*, 1998, 160, 5898-5906; International patent publications WO96/02555, WO98/16247, WO98/18810, WO98/40100, WO98/55495, WO98/37919 and WO98/52581] i.e. containing at least one CG dinucleotide, where the cytosine is unmethylated; (8) a polyoxyethylene ether or a polyoxyethylene ester e.g. WO99/52549; (9) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (10) a saponin and an immunostimulatory oligonucleotide (e.g a CpG oligonucleotide) (WO00/62800); (11) an immunostimulant and a particle of metal salt e.g. WO00/23105; (12) a saponin and an oil-in-water emulsion e.g. WO99/11241; (13) a saponin (e.g. QS21)+3dMPL+1M2 (optionally+a sterol) e.g. WO98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine MTP-PE), etc.

A subject immunogenic composition can include a conventional pharmaceutically acceptable excipient, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antigen in these formulations can vary widely, and will be selected primarily based on fluid volumes, viscosities, body weight and the like in accordance with the particular mode of administration selected and the patient's needs. The resulting compositions may be in the form of a solution, suspension, tablet, pill, capsule, powder, gel, cream, lotion, ointment, aerosol or the like.

The protein concentration of a subject PEAP in the pharmaceutical formulations can vary widely, i.e. from less than about 0.1%, from about 2% to about 20% to 50%, or more, by weight, and will be selected primarily by fluid volumes, viscosities, etc., in accordance with the particular mode of administration selected.

In some embodiments, a subject PEAP is formulated with one or more lipids. For example, liposomes of various sizes can be made. Small liposomes or vesicles formed are unilamellar and have a size in the range of about 20 to 400 nanometers and can be produced by subjecting multi-lamellar vesicles to ultrasound, by extrusion under pressure through membranes having pores of defined size, or by high pressure homogenization. Larger unilamellar liposomes having a size in the range of about 0.1 to 1 μm in diameter can be obtained when the lipid is solubilized in an organic solvent or a detergent and the solubilized agent is removed by evaporation or dialysis, respectively. The fusion of smaller unilamellar liposomes by methods requiring particular lipids or stringent dehydration-hydration conditions can yield unilamellar vessels as large or larger than cells.

Liposomes may comprise one or more cationic lipids, e.g., DDAB, dimethyldioctadecyl ammonium bromide; N-[1-(2,3-Dioloyloxy)propyl]-N,N,N-trimethylammonium methylsulfate; 1,2-diacyl-3-trimethylammonium-propanes, (including but not limited to, dioleoyl (DOTAP), dimyristoyl, dipalmitoyl, disearoyl); 1,2-diacyl-3-dimethylammonium-propanes, (including but not limited to, dioleoyl, dimyristoyl, dipalmitoyl, disearoyl) DOTMA, N-[1-[2,3-bis(oleoyloxy)]propyl]-N,N,N-trimethylammonium chloride; DOGS, dioctadecylamidoglycylspermine; DC-cholesterol, 3β-[N—(N',N'-dimethylaminoethane)carbamoyl]cholesterol; DOSPA, 2,3-dioleoyloxy-N-(2(sperminecarboxamido)-ethyl)-N,N-dimethyl-1-propanaminium trifluoroacetate; 1,2-diacyl-sn-glycero-3-ethylphosphocholines (including but not limited to dioleoyl (DOEPC), dilauroyl, dimyristoyl, dipalmitoyl, distearoyl, palmitoyl-oleoyl); β-alanyl cholesterol; CTAB, cetyl trimethyl ammonium bromide; diC14-amidine, N-t-butyl-N'-tetradecyl-3-tetradecylaminopropionamidine; 14Dea2, O,O'-ditetradecanolyl-N-(trimethylammonioacetyl) diethanolamine chloride; DOSPER, 1,3-dioleoyloxy-2-(6-carboxy-spermyl)-propylamide; N,N,N',N'-tetramethyl-N,N'-bis(2-hydroxylethyl)-2, 3-dioleoyloxy-1,4-butanediammonium iodide; 1-[2-acyloxy)ethyl]2-alkyl(alkenyl)-3-(2-hydroxyethyl) imidazolinium chloride derivatives such as 1-[2-(9(Z)-octadecenoyloxy)ethyl]-2-(8(Z)-heptadecenyl-3-(2-hydroxyethyl)imidazolinium chloride (DOTIM), 1-[2-(hexadecanoyloxy)ethyl]-2-pentadecyl-3-(2-hydroxyethyl) imidazolinium chloride (DPTIM); 1-[2-tetradecanoyloxy) ethyl]-2-tridecyl-3-(2-hydroxyethyl)imidazolium chloride (DMTIM)—as described in Solodin et al. (1995) Biochem. 43:13537-13544; 2,3-dialkyloxypropyl quaternary ammonium compound derivates, containing a hydroxyalkyl moiety on the quaternary amine, such as 1,2-dioleoyl-3-dimethyl-hydroxyethyl ammonium bromide (DORI); 1,2-dioleyloxypropyl-3-dimethyl-hydroxyethyl ammonium bromide (DORIE); 1,2-dioleyloxypropyl-3-dimethyl-hydroxypropyl ammonium bromide (DORIE-HP); 1,2-dioleyloxypropyl-3-dimethyl-hydroxybutyl ammonium bromide (DORIE-HB); 1,2-dioleyloxypropyl-3-dimethyl-hydroxypentyl ammonium bromide (DORIE-HPe); 1,2-dimyristyloxypropyl-3-dimethyl-hydroxylethyl ammonium bromide (DMRIE); 1,2-dipalmityloxypropyl-3-dimethyl-hydroxyethyl ammonium bromide (DPRIE); 1,2-disteryloxypropyl-3-dimethyl-hydroxyethyl ammonium bromide (DORIE)—as described, e.g., in Feigner et al. (1994) *J. Biol. Chem.* 269:2550-2561. Many of the above-mentioned lipids are available commercially from, e.g., Avanti Polar Lipids, Inc.; Sigma Chemical Co.; Molecular Probes, Inc.; Northern Lipids, Inc.; Roche Molecular Biochemicals; and Promega Corp.

Liposomes may comprise cationic lipids alone, or in admixture with other lipids, particularly neutral lipids such as: cholesterol; 1,2-diacyl-sn-glycero-3-phosphoethanolamines, (including but not limited to dioleoyl (DOPE), 1,2-diacyl-sn-glycero-3-phosphocholines; natural egg yolk phosphatidyl choline (PC), and the like; synthetic mono- and diacyl phosphocholines (e.g., monoacyl phosphatidyl choline (MOPC)) and phosphoethanolamines. Asymmetric fatty acids, both synthetic and natural, and mixed formulations, for the above diacyl derivatives may also be included.

Other suitable liposome compositions include dimyristoylphosphatidylcholine (DMPC) and cholesterol. Such liposomes are described in, e.g., U.S. Pat. No. 5,916,588. Additional suitable liposomal compositions, and methods of preparing same, are known in the art, and are described in various publications, including, e.g., U.S. Pat. Nos. 4,241,046 and 6,355,267.

PEAP Polynucleotides

The present disclosure provides a recombinant (e.g., synthetic) nucleic acid comprises a nucleotide sequence encoding a subject PEAP. A recombinant (e.g., synthetic) nucleic acid comprising a nucleotide sequence encoding a subject PEAP is referred to herein as a "subject PEAP-encoding nucleic acid," a "subject PEAP-encoding polynucleotide," or simply a "PEAP nucleic acid" or "PEAP polynucleotide." The present disclosure further provides compositions, including pharmaceutical compositions and immunogenic compositions, comprising a subject PEAP polynucleotide.

In certain embodiments, a subject PEAP polynucleotide comprises a nucleotide sequence encoding subject PEAP, where the PEAP comprises an amino acid sequence having at least about 75%, at least about 80%, at least about 85%, at least about 90%, at least about 95%, at least about 98%, at least about 99%, or 100%, amino acid sequence identity to the amino acid sequence as set forth in any one of SEQ ID NOs:11-22.

In some embodiments, a subject PEAP nucleic acid comprises a nucleotide sequence encoding a single type (or "species") of PEAP, e.g., in some embodiments, the PEAP nucleic acids all comprise nucleotide sequences substantially the same amino acid sequence. In other embodiments, a subject PEAP nucleic acid composition comprises two or more different PEAP nucleic acids, e.g., the composition comprises a population of PEAP nucleic acids encoding a population of PEAP, the members of which population can differ in amino acid sequence. A population of encoded PEAPs can comprise from two to about 20 different PEAPs, e.g., a subject composition can comprise two, three, four, five, six, seven, eight, nine, ten, 11-15, or 15-20 different PEAPs, each having an amino acid that differs from the amino acid sequences of the other PEAPs. For example, in some embodiments, a population of encoded PEAPs comprises a first PEAP having a first amino acid sequence; and at least a second PEAP having a second amino acid sequence, where the second amino acid sequence differs from the first amino acid sequence. As another example, in some embodiments, a population of encoded PEAPs a first PEAP having a first amino acid sequence; second PEAP having a second amino acid sequence, where the second amino acid sequence differs from the first amino acid sequence; and at least a third PEAP having a third amino acid sequence, where the third amino acid sequence differs from both the first and the second amino acid sequences. In other embodiments, the encoded PEAP is a multimerized PEAP, as described above.

Expression Vectors and Delivery Vehicles

In some embodiments, a subject PEAP polynucleotide is an expression vector. The expression vector will provide a transcriptional and translational initiation region, which may be inducible or constitutive, where the coding region is operably linked under the transcriptional control of the transcriptional initiation region, and a transcriptional and translational termination region. Thus, e.g., a subject PEAP polynucleotide can comprise a nucleotide sequence encoding a subject PEAP, where the PEAP-encoding nucleotide sequence is operably linked to a transcriptional control element (e.g., a promoter), where the transcriptional control element can be inducible or constitutive.

Expression vectors generally have convenient restriction sites located near the promoter sequence to provide for the insertion of nucleic acid sequences encoding heterologous proteins (e.g., to provide for insertion of a nucleotide sequence encoding a subject PEAP). A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXTI, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

Non-limiting examples of suitable eukaryotic promoters (promoters functional in a eukaryotic cell) include CMV immediate early, HSV thymidine kinase, early and late SV40, LTRs from retrovirus, and mouse metallothionein-1.

Selection of the appropriate vector and promoter is well within the level of ordinary skill in the art. The expression vector may also contain a ribosome binding site for translation initiation and a transcription terminator. The expression vector may also include appropriate sequences for amplifying expression.

A subject recombinant vector will in some embodiments include one or more selectable markers. In addition, the expression vectors can include one or more selectable marker genes to provide a phenotypic trait for selection of transformed host cells such as dihydrofolate reductase or neomycin resistance for eukaryotic cell culture.

Other gene delivery vehicles and methods may be employed, including polycationic condensed DNA linked or unlinked to killed adenovirus alone, for example Curiel (1992) *Hum. Gene Ther.* 3:147-154; ligand linked DNA, for example see Wu (1989) *J. Biol. Chem.* 264:16985-16987; eukaryotic cell delivery vehicles cells; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip (1994) *Mol. Cell Biol.* 14:2411-2418, and in Woffendin (1994) *Proc. Natl. Acad. Sci.* 91:1581-1585.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Nos. WO 95/13796, WO 94/23697, and WO 91/14445, and EP No. 524 968.

Liposome or lipid nucleic acid delivery vehicles can also be used. Liposome complexes for gene delivery are described in, e.g., U.S. Pat. No. 7,001,614. For example, liposomes comprising DOTAP and at least one cholesterol and/or cholesterol-derivative, present in a molar ratio range of 2.0 mM 10 mM provide an effective delivery system, e.g., where the molar ratio of DOTAP to cholesterol is 1:1 3:1. The cationic lipid N-[(2,3-dioleoyloxy)propyl]-L-lysinamide (LADOP) can be used in a composition for delivering a PEAP polynucleotide, where LADOP-containing liposomes are described in, e.g., U.S. Pat. No. 7,067,697. Liposome formulations comprising amphipathic lipids having a polar headgroup and aliphatic components capable of promoting transfection are suitable for use and are described in, e.g., U.S. Pat. No. 6,433,017.

Further non-viral delivery suitable for use includes mechanical delivery systems such as the approach described in Woffendin et al, (1994) *Proc. Natl. Acad. Sci. USA* 91:11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033.

Compositions

The present disclosure provides compositions comprising a subject PEAP nucleic acid. Compositions comprising a subject PEAP nucleic acid can include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a nuclease inhibitor; and the like. In some embodiments, as described in more detail below, a subject PEAP nucleic acid composition is an immunogenic composition.

Pharmaceutical Compositions

The present disclosure provides a pharmaceutical composition comprising a subject PEAP nucleic acid and a pharmaceutically acceptable excipient. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents.

Immunogenic Compositions

The present disclosure provides an immunogenic composition comprising a subject PEAP polynucleotide. When administered to an individual in need thereof, a polynucleotide comprising a nucleotide sequence encoding a subject PEAP is taken up by a cell, e.g., an antigen-presenting cell, the encoded PEAP is produced in the cell, and the PEAP is processed into polypeptide fragments ("epitope fragments") that are then displayed on the surface of the cell in association with an MHC molecule. The encoded PEAP stimulates or enhances a T cell response to the epitope(s) displayed on the cell surface. Where epitopes having the amino acid sequence of the PEAP epitopes are also present on a retrovirus-infected cell, a T cell response to the retrovirus-infected cell also occurs.

A subject immunogenic composition comprising a subject PEAP nucleic acid includes, in addition to a subject PEAP nucleic acid, one or more additional components, as described above for immunogenic compositions comprising a subject PEAP polypeptide.

Adjuvants

In some embodiments, a subject immunogenic composition comprises a subject PEAP polynucleotide and an adjuvant. Suitable adjuvants include those suitable for use in humans. Examples of known suitable adjuvants that can be used in humans include, but are not necessarily limited to, alum, aluminum phosphate, aluminum hydroxide, MF59 (4.3% w/v squalene, 0.5% w/v polysorbate 80 (Tween 80), 0.5% w/v sorbitan trioleate (Span 85)), a CpG-containing nucleic acid (where the cytosine is unmethylated), QS21

(saponin adjuvant), MPL (Monophosphoryl Lipid A), 3DMPL (3-O-deacylated MPL), extracts from Aquilla, ISCOMS (see, e.g., Sjölander et al. (1998) *J. Leukocyte Biol.* 64:713), LT/CT mutants, poly(D,L-lactide-co-glycolide) (PLG) microparticles, Quil A, interleukins, and the like. For veterinary applications including but not limited to animal experimentation, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in *Vaccine design: the subunit and adjuvant approach*, eds. Powell & Newman, Plenum Press 1995), containing 5% Squalene, 0.5% Tween 80 (polyoxyethylene sorbitan mono-oleate), and 0.5% Span 85 (sorbitan trioleate) (optionally containing muramyl tri-peptide covalently linked to dipalmitoyl phosphatidylethanolamine (MTP-PE)) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), e.g., MPL+CWS (DETOX™); (2) saponin adjuvants, such as QS21 or STIMULON™ (Cambridge Bioscience, Worcester, Mass.) may be used or particles generated therefrom such as ISCOMs (immunostimulating complexes), which ISCOMS may be devoid of additional detergent e.g. WO00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), other TNF superfamily molecules (e.g., CH40L, OX40L, and the like), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs [Krieg *Vaccine* 2000, 19, 618-622; Krieg *Curr Opin Mol Ther* 2001 3:15-24; Roman et al., *Nat. Med.*, 1997, 3, 849-854; Weiner et al., *PNAS USA*, 1997, 94, 10833-10837; Davis et al, *J Immunol*, 1998, 160, 870-876; Chu el al., *J. Exp. Med*, 1997, 186, 1623-1631; Lipford et al, *Eur. J. Immunol.*, 1997, 27, 2340-2344; Moldoveanu et al., *Vaccine*, 1988, 16, 1216-1224, Krieg et al., *Nature*, 1995, 374, 546-549; Klinman et al., *PNAS USA*, 1996, 93, 2879-2883; Ballas et al, *J. Immunol*, 1996, 157, 1840-1845; Cowdery et al, *J. Immunol*, 1996, 156, 4570-4575; Halpern et al, *Cell Immunol*, 1996, 167, 72-78; Yamamoto et al, *Jpn. J. Cancer Res.*, 1988, 79, 866-873; Stacey et al, *J. Immunol.*, 1996, 157,2116-2122; Messina et al, *J. Immunol*, 1991, 147, 1759-1764; Yi et al, *J. Immunol*, 1996, 157,4918-4925; Yi et al, *J. Immunol*, 1996, 157, 5394-5402; Yi et al, *J. Immunol*, 1998, 160, 4755-4761; and Yi et al, *J. Immunol*, 1998, 160, 5898-5906; International patent applications WO96/02555, WO98/16247, WO98/18810, WO98/40100, WO98/55495, WO98/37919 and WO98/52581] i.e. containing at least one CG dinucleotide, where the cytosine is unmethylated; (8) a polyoxyethylene ether or a polyoxyethylene ester e.g. WO99/52549; (9) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (10) a saponin and an immunostimulatory oligonucleotide (e.g. a CpG oligonucleotide) (WO00/62800); (11) an immunostimulant and a particle of metal salt e.g. WO00/23105; (12) a saponin and an oil-in-water emulsion e.g. WO99/11241; (13) a saponin (e.g. QS21)+3dMPL+1M2 (optionally+a sterol) e.g. WO98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc.

A subject immunogenic composition can include a conventional pharmaceutically acceptable excipient, such as pharmaceutical grades of mannitol, lactose, starch, magnesium stearate, sodium saccharin, talcum, cellulose, glucose, sucrose, magnesium, carbonate, and the like. A subject immunogenic composition can include one or more pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of a subject PEAP nucleic acid in these formulations can vary widely, and can be selected based on various factors such as fluid volumes, viscosities, body weight and the like in accordance with the particular mode of administration selected and the patient's needs. The resulting compositions may be in the form of a solution, suspension, tablet, pill, capsule, powder, gel, cream, lotion, ointment, aerosol or the like.

The concentration of a subject PEAP polynucleotide in the pharmaceutical formulations can vary widely, e.g., less than about 0.1%, from about 0.1% to about 2%, from about 2% to 20%, or from about 20% to about 50%, or more, by weight, and will be selected on the basis of various factors such as fluid volumes, viscosities, etc., in accordance with the particular mode of administration selected.

In some embodiments, a subject PEAP polynucleotide is formulated with one or more lipids. For example, liposomes of various sizes can be made. Small liposomes or vesicles formed are unilamellar and have a size in the range of about 20 to 400 nanometers and can be produced by subjecting multi-lamellar vesicles to ultrasound, by extrusion under pressure through membranes having pores of defined size, or by high pressure homogenization. Larger unilamellar liposomes having a size in the range of about 0.1 to 1 μm in diameter can be obtained when the lipid is solubilized in an organic solvent or a detergent and the solubilized agent is removed by evaporation or dialysis, respectively. The fusion of smaller unilamellar liposomes by methods requiring particular lipids or stringent dehydration-hydration conditions can yield unilamellar vessels as large as or larger than cells.

Liposomes can comprise one or more cationic lipids, e.g., DDAB, dimethyldioctadecyl ammonium bromide; N-[1-(2,3-Dioloyloxy)propyl]-N,N,N-trimethylammonium methylsulfate; 1,2-diacyl-3-trimethylammonium-propanes, (including but not limited to, dioleoyl (DOTAP), dimyristoyl, dipalmitoyl, disearoyl); 1,2-diacyl-3-dimethylammonium-propanes, (including but not limited to, dioleoyl, dimyristoyl, dipalmitoyl, disearoyl) DOTMA, N-[1-[2,3-bis(oleoyloxy)]propyl]-N,N,N-trimethylammonium chloride; DOGS, dioctadecylamidoglycylspermine; DC-cholesterol, 3β-[N—(N',N'-dimethylaminoethane)carbamoyl]cholesterol; DOSPA, 2,3-dioleoyloxy-N-(2(sperminecarboxamido)-ethyl)-N,N-dimethyl-1-propanaminium trifluoroacetate; 1,2-diacyl-sn-glycero-3-ethylphosphocholines (including but not limited to dioleoyl (DOEPC), dilauroyl, dimyristoyl, dipalmitoyl, distearoyl, palmitoyl-oleoyl); β-alanyl cholesterol; CTAB, cetyl trimethyl ammonium bromide; diCl4-amidine, N-t-butyl-N'-tetradecyl-3-tetradecylaminopropio-namidine; 14Dea2, O,O'-ditetradecanolyl-N-(trimethylammonioacetyl) diethanolamine chloride; DOSPER, 1,3-dioleoyloxy-2-(6-carboxy-spermyl)-propylamide; N,N,N',N'-tetramethyl-N,N'-bis(2-hydroxylethyl)-2,3-dioleoyloxy-1,4-butanediammonium iodide; 1-[2-acyloxy)ethyl]2-alkyl(alkenyl)-3-(2-hydroxyethyl) imidazolinium chloride derivatives such as 1-[2-(9(Z)-octadecenoyloxy)ethyl]-2-(8(Z)-heptadecenyl-3-(2-hydroxyethyl)imidazolinium chloride (DOTIM), 1-[2-(hexadecanoyloxy)ethyl]-2-pentadecyl-3-(2-hydroxyethyl) imidazolinium chloride (DPTIM); 1-[2-tetradecanoyloxy) ethyl]-2-tridecyl-3-(2-hydroxyethyl)imidazolium chloride (DMTIM)—as described in Solodin et al. (1995) Biochem. 43:13537-13544; 2,3-dialkyloxypropyl quaternary ammonium compound derivates, containing a hydroxyalkyl moiety on the quaternary amine, such as 1,2-dioleoyl-3-dimethyl-hydroxyethyl ammonium bromide (DORI); 1,2-dioleyloxypropyl-3-dimethyl-hydroxyethyl ammonium bromide (DORIE); 1,2-dioleyloxypropyl-3-dimethyl-hydroxypropyl ammonium bromide (DORIE-HP); 1,2-dioleyloxypropyl-3-dimethyl-hydroxybutyl ammonium bromide (DORIE-HB); 1,2-dioleyloxypropyl-3-dimethyl-hydroxypentyl ammonium bromide (DORIE-HPe); 1,2-dimyristyloxypropyl-3-dimethyl-hydroxylethyl ammonium bromide (DMRIE); 1,2-dipalmityloxypropyl-3-dimethyl-hydroxyethyl ammonium bromide (DPRIE); 1,2-disteryloxypropyl-3-dimethyl-hydroxyethyl ammonium bromide (DORIE)—as described, e.g., in Feigner et al. (1994) J. Biol. Chem. 269:2550-2561. Many of the above-mentioned lipids are available commercially from, e.g., Avanti Polar Lipids, Inc.; Sigma Chemical Co.; Molecular Probes, Inc.; Northern Lipids, Inc.; Roche Molecular Biochemicals; and Promega Corp.

Liposomes may comprise cationic lipids alone, or in admixture with other lipids, particularly neutral lipids such as: cholesterol; 1,2-diacyl-sn-glycero-3-phosphoethanolamines, (including but not limited to dioleoyl (DOPE), 1,2-diacyl-sn-glycero-3-phosphocholines; natural egg yolk phosphatidyl choline (PC), and the like; synthetic mono- and diacyl phosphocholines (e.g., monoacyl phosphatidyl choline (MOPC)) and phosphoethanolamines. Asymmetric fatty acids, both synthetic and natural, and mixed formulations, for the above diacyl derivatives may also be included.

Other suitable liposome compositions include dimyristoylphosphatidylcholine (DMPC) and cholesterol. Such liposomes are described in, e.g., U.S. Pat. No. 5,916,588. Additional suitable liposomal compositions, and methods of preparing same, are known in the art, and are described in various publications, including, e.g., U.S. Pat. Nos. 4,241,046 and 6,355,267.

Treatment and/or Prophylaxis Methods

A variety of treatment and/or prophylaxis methods are contemplated by the present disclosure, which methods utilize a subject PEAP, a subject PEAP nucleic acid, or a subject PEAP composition (e.g., a subject PEAP immunogenic composition, e.g., a subject PEAP immunogenic composition comprising a subject PEAP polypeptide, or a subject PEAP immunogenic composition comprising a subject PEAP polynucleotide). The treatment and/or prophylaxis methods include methods of inducing an immune response in an individual to a PEAP or an endogenous polypeptide having substantial amino acid sequence identity to a PEAP, and methods of enhancing a subject's immune response to a PEAP or an endogenous polypeptide having substantial amino acid sequence identity to a PEAP, e.g., for the treatment of a retrovirus infection (e.g., a lentivirus infection). Thus, e.g., the present disclosure provides methods of inducing an immune response in an individual to a retrovirus-infected cell (e.g., an HTLV-1-infected cell or an HIV-infected cell), methods of enhancing an immune response to a retrovirus-infected cell (e.g., an HTLV-1-infected cell or an HIV-infected cell), for the treatment of a retrovirus infection (e.g., a retroviral infection, such as an HTLV-1 infection or an HIV infection).

Methods of Inducing or Enhancing an Immune Response to a Retrovirus-Infected Cell The present disclosure provides methods for inducing, eliciting, or enhancing a T cell immune response to a retrovirus-infected cell, e.g., an HTLV-1-infected cell or an HIV-infected cell, in an individual in need thereof. The methods generally involve administering an effective amount of a subject PEAP, a subject PEAP polynucleotide, or a subject PEAP composition (e.g., a subject immunogenic composition, such as a subject immunogenic composition comprising a subject PEAP, or a subject immunogenic composition comprising a subject PEAP nucleic acid) to the individual.

In some embodiments, an "effective amount" of a subject PEAP, a subject PEAP polynucleotide, or a subject PEAP composition (e.g., a subject immunogenic composition, such as a subject immunogenic composition comprising a subject PEAP, or a subject immunogenic composition comprising a subject PEAP nucleic acid) is an amount that, when administered to an individual in one or more doses, reduces retroviral load in the individual by at least about 5%, at least about 10%, at least about 20%, at least about 25%, at least about 50%, at least about 75%, at least about 85%, or at least about 90%, compared to the viral load in the individual before treatment with the subject PEAP, the subject PEAP polynucleotide, or the subject PEAP composition.

For example, in some embodiments, an "effective amount" of a subject immunogenic composition is an amount that, when administered to an individual in one or more doses, reduces retroviral load in the individual by at least about 5%, at least about 10%, at least about 20%, at least about 25%, at least about 50%, at least about 75%, at least about 85%, or at least about 90%, compared to the viral load in the individual before treatment with the immunogenic composition.

In some embodiments, an "effective amount" of a subject PEAP, a subject PEAP polynucleotide, or a subject PEAP composition (e.g., a subject immunogenic composition, such as a subject immunogenic composition comprising a subject PEAP, or a subject immunogenic composition comprising a subject PEAP nucleic acid) is an amount that, when administered to an individual in one or more doses, results in an increase in the number of T cells specific for an epitope of an endogenous anti-viral polypeptide, which epitope is present on a retrovirus-infected cell. In some embodiments, an "effective amount" of a subject PEAP, a subject PEAP polynucleotide, or a subject PEAP composition (e.g., a subject immunogenic composition, such as a subject immunogenic composition comprising a subject PEAP, or a subject immunogenic composition comprising a subject PEAP nucleic acid) is an amount that, when administered to an individual in one or more doses, results in an increase of at least about 25%, at least about 50%, at least about 100% or 2-fold, at least about 5-fold, at least about 10-fold, or at least about 100-fold, or more, in the number of T cells specific for an epitope of an endogenous anti-viral polypeptide, which epitope is present on a retrovirus-infected cell, compared with the number of T cells specific for the epitope of the endogenous anti-viral polypeptide in the individual before treatment with the subject PEAP, the subject PEAP polynucleotide, or the subject PEAP composition.

For example, in some embodiments, an "effective amount" of a subject immunogenic composition is an amount that, when administered to an individual in one or more doses, results in an increase in the number of T cells specific for an epitope of an endogenous anti-viral polypeptide, which epitope is present on a retrovirus-infected cell. In some embodiments, an "effective amount" of a subject immunogenic composition is an amount that, when administered to an individual in one or more doses, results in an increase of at least about 25%, at least about 50%, at least about 100% or 2-fold, at least about 5-fold, at least about 10-fold, or at least about 100-fold, or more, in the number of T cells specific for an epitope of an endogenous anti-viral polypeptide, which epitope is present on a retrovirus-infected cell, compared with the number of T cells specific for the epitope of the endogenous anti-viral polypeptide in the individual before treatment with the immunogenic composition.

In some embodiments, an "effective amount" of a subject PEAP, a subject PEAP polynucleotide, or a subject PEAP composition (e.g., a subject immunogenic composition, such as a subject immunogenic composition comprising a subject PEAP, or a subject immunogenic composition comprising a subject PEAP nucleic acid) is an amount that, when administered to an individual in one or more doses, results in an increase in the number of $CD8^+$ T cells specific for an epitope of an endogenous anti-viral polypeptide, which epitope is present on a retrovirus-infected cell. In some embodiments, an "effective amount" of a subject PEAP, a subject PEAP polynucleotide, or a subject PEAP composition (e.g., a subject immunogenic composition, such as a subject immunogenic composition comprising a subject PEAP, or a subject immunogenic composition comprising a subject PEAP nucleic acid) is an amount that, when administered to an individual in one or more doses, results in an increase of at least about 25%, at least about 50%, at least about 100% or 2-fold, at least about 5-fold, at least about 10-fold, or at least about 100-fold, or more, in the number of $CD8^+$ T cells specific for an epitope of an endogenous anti-viral polypeptide, which epitope is present on a retrovirus-infected cell, compared with the number of $CD8^+$ T cells specific for the epitope of the endogenous anti-viral polypeptide in the individual before treatment with the subject PEAP, the subject PEAP polynucleotide, or the subject PEAP composition.

For example, in some embodiments, an "effective amount" of a subject immunogenic composition is an amount that, when administered to an individual in one or more doses, results in an increase in the number of $CD8^+$ T cells specific for an epitope of an endogenous anti-viral polypeptide, which epitope is present on a retrovirus-infected cell. In some embodiments, an "effective amount" of a subject immunogenic composition is an amount that, when administered to an individual in one or more doses, results in an increase of at least about 25%, at least about 50%, at least about 100% or 2-fold, at least about 5-fold, at least about 10-fold, or at least about 100-fold, or more, in the number of $CD8^+$ T cells specific for an epitope of an endogenous anti-viral polypeptide, which epitope is present on a retrovirus-infected cell, compared with the number of $CD8^+$ T cells specific for the epitope of the endogenous anti-viral polypeptide in the individual before treatment with the immunogenic composition.

Prophylactic Methods

In some embodiments, a subject PEAP, a subject PEAP polynucleotide, or a subject PEAP composition (e.g., a subject immunogenic composition, such as a subject immunogenic composition comprising a subject PEAP, or a subject immunogenic composition comprising a subject PEAP nucleic acid) is administered to a naïve individual (e.g., an individual not infected with a retrovirus such as HTLV-1 or HIV) or an individual seronegative for a retrovirus such as HTLV-1 or HIV. In such embodiments, an "effective amount" of a subject PEAP, a subject PEAP polynucleotide, or a subject PEAP composition (e.g., a subject immunogenic composition, such as a subject immunogenic composition comprising a subject PEAP, or a subject immunogenic composition comprising a subject PEAP nucleic acid) is an amount that, when administered to an individual in one or more doses, reduces the likelihood that the individual, if later infected with a retrovirus such as HTLV-1 or HIV, would develop disease symptoms from the retrovirus infection. In some embodiments where a subject PEAP, a subject PEAP polynucleotide, or a subject PEAP composition (e.g., a subject immunogenic composition, such as a subject immunogenic composition comprising a subject PEAP, or a subject immunogenic composition comprising a subject PEAP nucleic acid) is administered to a naïve individual (e.g., an individual not infected with a retrovirus) or an individual seronegative for the retrovirus, an "effective amount" of a subject PEAP, a subject PEAP polynucleotide, or a subject PEAP composition (e.g., a subject immunogenic composition, such as a subject immunogenic composition comprising a subject PEAP, or a subject immunogenic composition comprising a subject PEAP nucleic acid) is an amount that, when administered to an individual in one or more doses, increases the likelihood that the individual, if later infected with a retrovirus such as HTLV-1 or HIV, would limit and/or clear the retrovirus infection.

For example, in some embodiments where a subject immunogenic composition is administered to a naïve individual (e.g., an individual not infected with a retrovirus such as HTLV-1 or HIV) or an individual seronegative for a retrovirus such as HTLV-1 or HIV, an "effective amount" of a subject immunogenic composition is an amount that, when administered to an individual in one or more doses, reduces the likelihood that the individual, if later infected with a retrovirus such as HTLV-1 or HIV, would develop disease symptoms from the retrovirus infection. In some embodiments where a subject immunogenic composition is administered to a naïve individual (e.g., an individual not infected with a retrovirus) or an individual seronegative for a retrovirus, an "effective amount" of a subject immunogenic composition is an amount that, when administered to an individual in one or more doses, increases the likelihood that the individual, if later infected with a retrovirus such as HTLV-1 or HIV, would limit and/or clear the retrovirus infection.

Combination Therapies

A subject immunogenic composition can be administered in conjunction with one or more therapeutic agents for the treatment of a retroviral, e.g., a lentiviral infection, or for the treatment of a disorder that may accompany a retroviral, e.g., a lentiviral infection (e.g., a bacterial infection, a fungal infection, and the like). Therapeutic agents include, e.g., beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddl, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), kaletra, trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof.

Methods of Treating Cancer

The present disclosure further provides methods of treating cancer in an individual, where the cancerous state is associated with aberrant expression of an endogenous polypeptide having an amino acid sequence substantially similar to that of a subject PEAP or increased expression of an endogenous polypeptide having an amino acid sequence substantially similar to that of a subject PEAP, e.g., where the cancer comprises a cancer cell or a pre-cancerous cell that exhibits aberrant expression of an endogenous polypeptide having an amino acid sequence substantially similar to that of a subject PEAP (e.g., expresses an endogenous polypeptide having an amino acid sequence substantially similar to that of a subject PEAP at a level that is at least about 15%, at least about 25%, at least about 30%, at least about 40%, at least about 50%, at least about 75%, at least about 2-fold, at least about 5-fold, or at least about 10-fold, or more than 10-fold, higher than the level of the endogenous polypeptide having an amino acid sequence substantially similar to that of a subject PEAP expressed by a non-cancerous (normal) cell of the same cell type). Such cancers include, but are not limited to, myeloma, melanoma, ovarian cancer, breast cancer, and testicular cancer (including teratoma, seminoma, and embryonal carcinoma or mixed tumors composed of one or more of these types). The methods generally involve administering to an individual in need thereof an effective amount of a subject PEAP (e.g., a subject synthetic PEAP), a subject PEAP polynucleotide, or a subject PEAP composition (e.g., a subject PEAP pharmaceutical composition or a subject PEAP immunogenic composition). In some embodiments, the methods generally involve administering to an individual in need thereof an effective amount of a subject PEAP immunogenic composition (e.g., a subject PEAP immunogenic composition comprising one or more subject PEAPs or one or more subject PEAP polynucleotides).

The present disclosure provides methods for treating a cancer (e.g., myeloma, melanoma, ovarian cancer, breast cancer, and testicular cancer (including teratoma, seminoma, and embryonal carcinoma or mixed tumors composed of one or more of these types) in an individual, the methods generally involving administering to an individual in need thereof an effective amount of a subject PEAP (e.g. a subject synthetic PEAP), a subject PEAP polynucleotide, or a subject PEAP composition (e.g., a subject PEAP pharmaceutical composition or a subject PEAP immunogenic composition). In some embodiments, the present disclosure provides methods for treating cancer in an individual, the methods generally involving administering to an individual in need thereof an effective amount of a subject PEAP immunogenic composition, e.g., a subject immunogenic composition comprising a subject PEAP or a subject PEAP polynucleotide. The present disclosure provides use of a subject PEAP, a subject PEAP polynucleotide, or a subject PEAP composition in the preparation of a medicament for the treatment of a cancer in an individual. The present disclosure provides use of a subject PEAP immunogenic composition (e.g., a subject immunogenic composition comprising a subject PEAP or a subject PEAP polynucleotide) in the preparation of a medicament for the treatment of a cancer in an individual. The present disclosure provides a subject PEAP, a subject PEAP polynucleotide, or a subject PEAP composition for treating a cancer in an individual. The present disclosure provides a subject PEAP immunogenic composition (e.g., a subject immunogenic composition comprising a subject PEAP or a subject PEAP polynucleotide) for treating a cancer in an individual.

For example, an effective amount of a subject PEAP, a subject PEAP polynucleotide, or a subject PEAP composition is administered to an individual having a tumor (e.g., a solid tumor), wherein the cells of the tumor express an endogenous polypeptide having an amino acid sequence substantially similar to that of a subject PEAP as a marker of the cancerous state.

For example, an effective amount of a subject immunogenic composition comprising one or more PEAPs is administered to an individual having a tumor (e.g., a solid tumor), wherein the cells of the tumor express an endogenous polypeptide having an amino acid sequence substantially similar to that of a subject PEAP as a marker of the cancerous state.

As another example, an effective amount of a subject PEAP, a subject PEAP polynucleotide, or a subject PEAP composition is administered to a subject having a tumor, wherein the tissue from which the tumor expresses an endogenous polypeptide having an amino acid sequence substantially similar to that of a subject PEAP in the non-cancerous state and such tissue exhibits an increase (e.g., an at least about 15%, at least about 25%, at least about 30%, at least about 40%, at least about 50%, at least about 75%, at least about 2-fold, at least about 5-fold, or at least about 10-fold, or more than 10-fold, increase) in expression of the endogenous polypeptide having an amino acid sequence substantially similar to that of a subject PEAP as a marker of the cancerous state.

As another example, an effective amount of a subject immunogenic composition is administered to a subject having a tumor, wherein the tissue from which the tumor expresses an endogenous polypeptide having an amino acid sequence substantially similar to that of a subject PEAP in the non-cancerous state exhibits an increase (e.g., an at least about 15%, at least about 25%, at least about 30%, at least about 40%, at least about 50%, at least about 75%, at least about 2-fold, at least about 5-fold, or at least about 10-fold, or more than 10-fold, increase) in expression of the endogenous polypeptide having an amino acid sequence substantially similar to that of a subject PEAP as a marker of the cancerous state.

Cancers amenable to treatment with subject immunogenic compositions include ovarian cancer, breast cancer, myeloma, melanoma, prostate cancer, and testicular cancer (including seminoma, teratoma, and embryonal carcinoma).

In some embodiments, in the context of cancer treatment, an "effective amount" of a subject PEAP, a subject PEAP polynucleotide, or a subject PEAP composition is an amount that, when administered to an individual in one or more doses, reduces one or more of tumor size, cancer cell number, and cancer cell metastasis by at least about 10%, at least about 20%, at least about 30%, at least about 40%, at least about 50%, at least about 60%, at least about 70%, at least about 80%, or at least about 90%, up to total eradication of the cancer.

In some embodiments, in the context of cancer treatment, an "effective amount" of a subject immunogenic composition is an amount that, when administered to an individual in one or more doses, reduces one or more of tumor size, cancer cell number, and cancer cell metastasis by at least about 10%, at least about 20%, at least about 30%, at least about 40%, at least about 50%, at least about 60%, at least about 70%, at least about 80%, or at least about 90%, up to total eradication of the cancer.

In some embodiments, an "effective amount" of a subject PEAP, a subject PEAP polynucleotide, or a subject PEAP composition is an amount that, when administered to an individual in one or more doses, results in an increase in the number of T cells specific for an epitope present on a cancer cell. In some embodiments, an "effective amount" of a subject PEAP, a subject PEAP polynucleotide, or a subject PEAP composition is an amount that, when administered to an individual in one or more doses, results in an increase of at least about 25%, at least about 50%, at least about 100% or 2-fold, at least about 5-fold, at least about 10-fold, or at least about 100-fold, or more, in the number of T cells specific for an epitope present on a cancer cell, compared with the number of T cells specific for a cancer cell epitope in the individual before treatment with the subject PEAP, subject PEAP polynucleotide, or the subject PEAP composition.

In some embodiments, an "effective amount" of a subject immunogenic composition is an amount that, when administered to an individual in one or more doses, results in an increase in the number of T cells specific for an epitope present on a cancer cell. In some embodiments, an "effective amount" of a subject immunogenic composition is an amount that, when administered to an individual in one or more doses, results in an increase of at least about 25%, at least about 50%, at least about 100% or 2-fold, at least about 5-fold, at least about 10-fold, or at least about 100-fold, or more, in the number of T cells specific for an epitope present on a cancer cell, compared with the number of T cells specific for a cancer cell epitope in the individual before treatment with the immunogenic composition.

In some embodiments, an "effective amount" of a subject PEAP, a subject PEAP polynucleotide, or a subject PEAP composition is an amount that, when administered to an individual in one or more doses, results in an increase in the number of $CD8^+$ T cells specific for an epitope present on a cancer cell. In some embodiments, an "effective amount" of a subject PEAP, a subject PEAP polynucleotide, or a subject PEAP composition is an amount that, when administered to an individual in one or more doses, results in an increase of at least about 25%, at least about 50%, at least about 100% or 2-fold, at least about 5-fold, at least about 10-fold, or at least about 100-fold, or more, in the number of $CD8^+$ T cells specific for a an epitope present on a cancer cell, compared with the number of $CD8^+$ T cells specific for a cancer cell epitope in the individual before treatment with the subject PEAP, the subject PEAP polynucleotide, or the subject PEAP composition.

In some embodiments, an "effective amount" of a subject immunogenic composition is an amount that, when administered to an individual in one or more doses, results in an increase in the number of $CD8^+$ T cells specific for an epitope present on a cancer cell. In some embodiments, an "effective amount" of a subject immunogenic composition is an amount that, when administered to an individual in one or more doses, results in an increase of at least about 25%, at least about 50%, at least about 100% or 2-fold, at least about 5-fold, at least about 10-fold, or at least about 100-fold, or more, in the number of $CD8^+$ T cells specific for a an epitope present on a cancer cell, compared with the number of $CD8^+$ T cells specific for a cancer cell epitope in the individual before treatment with the immunogenic composition.

In some embodiments, a subject PEAP, a subject PEAP polynucleotide, or a subject PEAP composition (e.g., a subject PEAP immunogenic composition) is administered to an individual in need thereof as an adjuvant therapy to a standard cancer therapy. Standard cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore, compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere□ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use in connection with the methods of the invention include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ (8) colony-stimulating factors; and (9) inhibitors of angiogenesis.

In some embodiments, in the context of cancer treatment, a subject PEAP, a subject PEAP polynucleotide, or a subject PEAP composition as described above does not comprise an amino acid sequence (or a nucleotide sequence encoding the amino acid sequence, in the case of a polynucleotide) of an endogenous tetherin (a.k.a., BST2, a.k.a., CD317, a.k.a, HM1.24) polypeptide. In some embodiments, in the context of cancer treatment, a subject PEAP, a subject PEAP polynucleotide, or a subject PEAP composition does not comprise more than 5 contiguous amino acids (or a nucleotide sequence encoding more than 5 contiguous amino acids, in the case of a polynucleotide) of SEQ ID NO:23.

Formulations

A subject PEAP, as described above, can be formulated in any of a variety of ways for administration to an individual in need thereof. The present disclosure provides pharmaceutical formulations comprising a PEAP. Immunogenic compositions comprising a PEAP or a nucleic acid encoding a PEAP are described above. Additional formulations are described below.

A formulation comprising a PEAP can include one or more excipients (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfate, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

Tablets comprising an active agent may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, e.g., for use in inducing or enhancing an immune response to a *lentivirus*, a PEAP is formulated for vaginal delivery. A subject formulation for intravaginal administration is formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

Dosages

The appropriate dosage of a subject PEAP that, when administered in one or multiple doses, has the desired effect (e.g., increases a T cell immune response to a *lentivirus*-infected cell), will vary, depending on various factors, but will generally be in the range of from about 1 µg to about 100 mg, e.g., from about 1 µg to about 5 µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg, from about 1 mg to about 10 mg, from about 10 mg to about 50 mg, or from about 50 mg to about 100 mg, administered in one dose or divided into multiple doses.

In some embodiments, the amount of PEAP per dose is determined on a per body weight basis. For example, in some embodiments, a PEAP is administered in an amount of from about 0.5 mg/kg to about 100 mg/kg, e.g., from about 0.5 mg/kg to about 1 mg/kg, from about 1 mg/kg to about 2 mg/kg, from about 2 mg/kg to about 3 mg/kg, from about 3 mg/kg to about 5 mg/kg, from about 5 mg/kg to about 7 mg/kg, from about 7 mg/kg to about 10 mg/kg, from about 10 mg/kg to about 15 mg/kg, from about 15 mg/kg to about 20 mg/kg, from about 20 mg/kg to about 25 mg/kg, from about 25 mg/kg to about 30 mg/kg, from about 30 mg/kg to about 40 mg/kg, from about 40 mg/kg to about 50 mg/kg per dose, from about 50 mg/kg to about 60 mg/kg, from about 60 mg/kg to about 70 mg/kg, from about 70 mg/kg to about 80 mg/kg, from about 80 mg/kg to about 90 mg/kg, or from about 90 mg/kg to about 100 mg/kg, or more than about 100 mg/kg.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, multiple doses of a subject PEAP are administered. The frequency of administration of a PEAP can vary depending on any of a variety of factors, e.g., severity of the symptoms, etc. For example, in some embodiments, a PEAP is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a PEAP, e.g., the period of time over which a PEAP is administered, can vary, depending on any of a variety of factors, e.g., patient response, etc. For example, a PEAP can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Routes of Administration

Conventional and pharmaceutically acceptable routes of administration include intranasal, intramuscular, intratracheal, intratumoral, transdermal, subcutaneous, intradermal, topical application, intravenous, vaginal, nasal, and other parenteral routes of administration. Suitable routes of administration also include oral and rectal routes. Routes of administration may be combined, if desired, or adjusted depending upon the agent and/or the desired effect. The composition can be administered in a single dose or in multiple doses.

A subject PEAP composition can be administered to a host using any available conventional methods and routes suitable for delivery of conventional drugs, including systemic or localized routes. In general, routes of administration contemplated by the disclosure include, but are not necessarily limited to, enteral, parenteral, or inhalational routes.

Parenteral routes of administration other than inhalation administration include, but are not necessarily limited to, topical, vaginal, transdermal, subcutaneous, intramuscular, intraorbital, intracapsular, intraspinal, intrasternal, intratumoral, peritumoral, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

A subject PEAP composition can also be delivered to the subject by enteral administration. Enteral routes of administration include, but are not necessarily limited to, oral and rectal (e.g., using a suppository) delivery.

A subject immunogenic composition can be delivered to mucosal tissue, e.g., to vaginal tissue, to rectal tissue, etc.

Methods of Generating PEAP-Specific $CD8^+$ T Cells

The present disclosure provides methods of generating a population of PEAP-specific CD8+ T cells in vitro. The methods generally involve contacting a CD8+ T cell, or a precursor thereof, with a subject PEAP in association with an antigen-presenting platform, where the contacting is performed in vitro. The methods are useful for generating a population of PEAP-specific CD8+ T cells, which are in turn useful in methods of treating disorders such as retrovirus infection, e.g., lentivirus infection (e.g., HIV infection).

In some embodiments, CD8+ T cells are obtained from an individual, and are contacted in vitro with a PEAP in association with an antigen-presenting platform. In some embodiments, a mixed population of cells that comprises CD8+ T cells is obtained from an individual; and CD8+ T cells are isolated from the mixed population, generating an unstimulated CD8+ T cell population. The unstimulated CD8+ T cell population is then contacted in vitro to a PEAP in association with an antigen-presenting platform. The contacting step activates at least a portion of the unstimulated CD8+ T cell population having T cell receptors capable of binding a PEAP to become specific for a PEAP.

The source of the mixed cell population that comprises a CD8+ T cell can be, e.g., whole blood. The mixed cell population can be manipulated in one or more ways or steps, e.g., to remove red blood cells; to select for CD8+ T cells; and/or to select against CD4+ T cells or other non-CD8+ cell populations. The number of unstimulated CD8+ cells can range from about $10^2$ to about $10^9$ cells, e.g., from about $10^2$ cells to about $10^3$ cells, from about $10^3$ cells to about $10^4$ cells, from about $10^4$ cells to about $10^5$ cells, from about $10^5$ cells to about $5\times10^5$ cells, from about $5\times10^5$ cells to about $10^6$ cells, from about $10^6$ cells to about $5\times10^6$ cells, from about $5\times10^6$ cells to about $10^7$ cells, from about $10^7$ cells to about $5\times10^7$ cells, from about $5\times10^7$ cells to about $10^8$ cells, from about $10^8$ cells to about $5\times10^8$ cells, or from about $5\times10^8$ cells to about $10^9$ cells.

The antigen-presenting platform can be an antigen-presenting cell (APC), e.g., an APC pulsed with a PEAP, where the APC can be live or can be inactivated. In some embodiments, the antigen-presenting platform is a bead (e.g., a plastic bead, a magnetic bead, etc.), or other particle, to which a PEAP is bound. Antigen-presenting platforms other than naturally-occurring APCs are known in the art and include, but are not limited to, beads; inactivated surface-engineered viruses (see, e.g., Mosca et al. (2007) Retrovirol. 4:32); artificial APCs, e.g., liposomes (see, e.g, U.S. Patent Publication No. 2006/0034865); and the like.

The antigen-presenting platform will include, in addition to a PEAP, one or more surface molecules sufficient for stimulating expansion of a PEAP-specific CD8+ T cell population, e.g., MHC class I molecules (e.g., HLA Class I molecules), etc. The antigen-presenting platform can also include one or more co-stimulatory molecules, where suitable co-stimulatory molecules include, but are not limited to, an anti-CD28 antibody, an anti-CD49d antibody, and the like).

The unstimulated CD8+ T cells are contacted in vitro with a PEAP in association with an antigen-presenting platform; and the number of PEAP-specific CD8+ T cells is increased. The method results in a 10-fold to a $10^6$-fold increase in the number of PEAP-specific CD8+ T cells. The number of PEAP-specific CD8+ cells obtained by the disclosed method can range from about $10^3$ to about $10^9$ cells, e.g., from about $10^3$ cells to about $10^4$ cells, from about $10^4$ cells to about $10^5$ cells, from about $10^5$ cells to about $5\times10^5$ cells, from about $5\times10^5$ cells to about $10^6$ cells, from about $10^6$ cells to about $5\times10^6$ cells, from about $5\times10^6$ cells to about $10^4$ cells, from about $10^7$ cells to about $5\times10^7$ cells, from about $5\times10^7$ cells to about $10^8$ cells, from about $10^8$ cells to about $5\times10^8$ cells, or from about $5\times10^8$ cells to about $10^9$ cells.

The present disclosure provides treatment methods using the PEAP-specific CD8+ T cells. In some embodiments, the methods are methods of treating an HIV infection. The methods generally involve administering to an individual in need thereof an effective amount of PEAP-specific CD8+ T cells. In some embodiments, the PEAP-specific CD8+ T cells are autologous, e.g., the PEAP-specific CD8+ T cells are administered to the same individual from which the mixed cell population was obtained (i.e., the donor individual and the recipient individual are the same). In other embodiments, the PEAP-specific CD8+ T cells are allogeneic, e.g., the PEAP-specific CD8+ T cells are administered to an individual (a recipient individual) not genetically identical to the individual from which the mixed cell population was obtained (the donor individual).

In some embodiments, the PEAP-specific CD8+ T cells are administered to a recipient individual in an amount of from about $10^3$ to about $10^9$ cells, e.g., from about $10^3$ cells to about $10^4$ cells, from about $10^4$ cells to about $10^5$ cells, from about $10^5$ cells to about $5\times10^5$ cells, from about $5\times10^5$ cells to about $10^6$ cells, from about $10^6$ cells to about $5\times10^6$ cells, from about $5\times10^6$ cells to about $10^7$ cells, from about $10^7$ cells to about $5\times10^7$ cells, from about $5\times10^7$ cells to about $10^8$ cells, from about $10^8$ cells to about $5\times10^8$ cells, or from about $5\times10^8$ cells to about $10^9$ cells, in one or more doses.

Methods of Generating PEAP-Specific CD4+ T Cells

The present disclosure also provides methods of generating a population of PEAP-specific CD4+ T cells in vitro. The methods generally involve contacting a CD4+ T cell, or a precursor thereof, with a subject PEAP in association with an antigen-presenting platform, where the contacting is performed in vitro. The methods are useful for generating a population of PEAP-specific CD4+ T cells, which are in turn useful in methods of treating disorders such as retrovirus infection, e.g., lentivirus infection (e.g., HIV infection).

In some embodiments, CD4+ T cells are obtained from an individual, and are contacted in vitro with a PEAP in association with an antigen-presenting platform. In some embodiments, a mixed population of cells that comprises CD4+ T cells is obtained from an individual; and CD4+ T cells are isolated from the mixed population, generating an unstimulated CD4+ T cell population. The unstimulated CD4+ T cell population is then contacted in vitro to a PEAP in association with an antigen-presenting platform. The contacting step activates at least a portion of the unstimulated CD4+ T cell population having T cell receptors capable of binding a PEAP to become specific for a PEAP.

The source of the mixed cell population that comprises a CD4+ T cell can be, e.g., whole blood. The mixed cell population can be manipulated in one or more ways or steps, e.g., to remove red blood cells; to select for CD4+ T cells; and/or to select against CD8+ T cells or other non-CD4+ cell populations. The number of unstimulated CD4+ cells can range from about $10^2$ to about $10^9$ cells, e.g., from about $10^2$ cells to about $10^3$ cells, from about $10^3$ cells to about $10^4$ cells, from about $10^4$ cells to about $10^5$ cells, from about $10^5$ cells to about $5\times10^5$ cells, from about $5\times10^5$ cells to about $10^6$ cells, from about $10^6$ cells to about $5\times10^6$ cells, from about $5\times10^6$ cells to about $10^7$ cells, from about $10^7$ cells to about $5\times10^7$ cells, from about $55\times10^7$ cells to about $10^8$ cells, from about $10^8$ cells to about $5\times10^8$ cells, or from about $5\times10^8$ cells to about $10^9$ cells.

The antigen-presenting platform can be an antigen-presenting cell (APC), e.g., an APC pulsed with a PEAP, where the APC can be live or can be inactivated. In some embodiments, the antigen-presenting platform is a bead (e.g., a plastic bead, a magnetic bead, etc.), or other particle, to which a PEAP is bound. Antigen-presenting platforms other than naturally-occurring APCs are known in the art and include, but are not limited to, beads; inactivated surface-engineered viruses (see, e.g., Mosca et al. (2007) *Retrovirol.* 4:32); artificial APCs, e.g., liposomes (see, e.g, U.S. Patent Publication No. 2006/0034865); and the like.

The antigen-presenting platform will include, in addition to a PEAP, one or more surface molecules sufficient for stimulating expansion of a PEAP-specific CD4$^+$ T cell population, e.g., MHC class II molecules (e.g., HLA Class II molecules), etc. The antigen-presenting platform can also include one or more co-stimulatory molecules, where suitable co-stimulatory molecules include, but are not limited to, an anti-CD28 antibody, an anti-CD49d antibody, and the like).

The unstimulated CD4$^+$ T cells are contacted in vitro with a PEAP in association with an antigen-presenting platform; and the number of PEAP-specific CD4$^+$ T cells is increased. The method results in a 10-fold to a $10^6$-fold increase in the number of PEAP-specific CD4$^+$ T cells. The number of PEAP-specific CD4$^+$ cells obtained by the disclosed method can range from about $10^3$ to about $10^9$ cells, e.g., from about $10^3$ cells to about $10^4$ cells, from about $10^4$ cells to about $10^5$ cells, from about $10^5$ cells to about $5\times10^5$ cells, from about $5\times10^5$ cells to about $10^6$ cells, from about $10^6$ cells to about $5\times10^6$ cells, from about $5\times10^6$ cells to about $10^7$ cells, from about $10^7$ cells to about $5\times10^7$ cells, from about $5\times10^7$ cells to about $10^8$ cells, from about $10^8$ cells to about $5\times10^8$ cells, or from about $5\times10^8$ cells to about $10^9$ cells.

The present disclosure provides treatment methods using the PEAP-specific CD4$^+$ T cells. In some embodiments, the methods are methods of treating an HIV infection. The methods generally involve administering to an individual in need thereof an effective amount of PEAP-specific CD4$^+$ T cells. In some embodiments, the PEAP-specific CD4$^+$ T cells are autologous, e.g., the PEAP-specific CD4$^+$ T cells are administered to the same individual from which the mixed cell population was obtained (i.e., the donor individual and the recipient individual are the same). In other embodiments, the PEAP-specific CD4$^+$ T cells are allogeneic, e.g., the PEAP-specific CD4$^+$ T cells are administered to an individual (a recipient individual) not genetically identical to the individual from which the mixed cell population was obtained (the donor individual).

In some embodiments, the PEAP-specific CD4$^+$ T cells are administered to a recipient individual in an amount of from about $10^3$ to about $10^9$ cells, e.g., from about $10^3$ cells to about $10^4$ cells, from about $10^4$ cells to about $10^5$ cells, from about $10^5$ cells to about $5\times10^5$ cells, from about $5\times10^5$ cells to about $10^6$ cells, from about $10^6$ cells to about $5\times10^6$ cells, from about $5\times10^6$ cells to about $10^7$ cells, from about $10^7$ cells to about $55\times10^8$ cells, from about $5\times10^7$ cells to about $10^8$ cells, from about $10^8$ cells to about $5\times10^8$ cells, or from about $5\times10^8$ cells to about $10^9$ cells, in one or more doses.

Diagnostic Methods

The present disclosure provides various diagnostic methods, which methods utilize a subject PEAP polypeptide or a subject PEAP composition. Subject diagnostic methods include methods for monitoring a patient's response to treatment; methods for staging a disease; and methods for detecting a disease.

Diagnostic methods can involves detecting the number of PEAP-specific CD8$^+$ T cells in a biological sample obtained from an individual. The number of PEAP-specific CD8$^+$ T cells can be determined using, e.g., a $^{51}$Cr release assay, where target cells pulsed with a PEAP and labeled with $^{51}$Cr are contacted with a test sample that may contain PEAP-specific CD8$^+$ T cells. The number of PEAP-specific CD8$^+$ T cells is determined by measuring release of $^{51}$Cr from the target cells.

In other embodiments, a disclosed diagnostic method involves detecting a PEAP or an endogenous polypeptide having an amino acid sequence substantially similar to that of a subject PEAP in the serum or plasma (or other biological fluid) of an individual. Detection of a PEAP or an endogenous polypeptide having an amino acid sequence substantially similar to that of a subject PEAP in a biological fluid obtained from an individual can be carried out using, e.g., immunological assays employing antibody specific for a PEAP. Suitable immunological assays include, but are not limited to, enzyme-linked immunosorbent assays (ELISA), radioimmunoassays (RIA), protein blot ("Western blot") assays, immunoprecipitation assays, and the like.

PEAP-Specific Antibodies

As noted above, in some embodiments, a subject diagnostic assay will employ an antibody specific for a PEAP (an "anti-PEAP antibody"). Suitable anti-PEAP antibodies include whole antibody of any isotype; epitope-binding fragments of an anti-PEAP antibody; polyclonal antibodies; monoclonal antibodies; artificial antibodies; single-chain antibodies; and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies include mouse, rat, hamster, guinea pig, rabbit, etc. The antibody may be purified from the hybridoma cell supernatants or ascites fluid by conventional techniques, e.g. affinity chromatography using protein bound to an insoluble support, protein A sepharose, etc.

The antibody may be produced as a single chain, instead of the normal multimeric structure. Single chain antibodies are described in Jost et al. (1994) J. B. C. 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Suitable anti-PEAP antibodies also include "artificial" antibodies, e.g., antibodies and antibody fragments produced and selected in vitro. In some embodiments, such antibodies are displayed on the surface of a bacteriophage or other viral particle. In many embodiments, such artificial antibodies are present as fusion proteins with a viral or bacteriophage structural protein, including, but not limited to, M13 gene III protein. Methods of producing such artificial antibodies are well known in the art. See, e.g., U.S. Pat. Nos. 5,516,637; 5,223,409; 5,658,727; 5,667,988; 5,498, 538; 5,403,484; 5,571,698; and 5,625,033.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

An anti-PEAP antibody will in some embodiments be detectably labeled, e.g., with a radioisotope, an enzyme which generates a detectable product, a fluorescent protein, a chromogenic protein, and the like. An anti-PEAP antibody may be further conjugated to other moieties, such as members of specific binding pairs, e.g., biotin (member of biotin-avidin specific binding pair), and the like. An anti-PEAP antibody may also be bound to a solid support, including, but not limited to, polystyrene plates or beads, magnetic beads, test strips, membranes, and the like.

An antibody specific for a PEAP can be labeled, directly or indirectly. Direct labels include radioisotopes (e.g., $^{125}$I; $^{35}$S, and the like); enzymes whose products are detectable (e.g., luciferase, β-galactosidase, horse radish peroxidase, alkaline phosphatase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins (e.g., a green fluorescent protein, a yellow fluorescent protein, etc.); and the like. Indirect labels include second antibodies specific for PEAP-specific antibodies, wherein the second antibody is labeled as described above; and members of specific binding pairs, e.g., biotin-avidin, and the like.

In some embodiments, an anti-PEAP antibody comprises, covalently linked to the antibody, a protein that provides for a detectable signal. Suitable proteins include, but are not limited to, fluorescent proteins and enzymes (e.g., β-galactosidase, luciferase, horse radish peroxidase, alkaline phosphatase, etc.). Suitable fluorescent proteins include, but are not limited to, a green fluorescent protein (GFP), including, but not limited to, a GFP derived from *Aequoria victoria* or a derivative thereof, a number of which are commercially available; a GFP from a species such as *Renilla reniformis*, *Renilla mulleri*, or *Ptilosarcus guernyi*, as described in, e.g., WO 99/49019 and Peelle et al. (2001) *J. Protein Chem.* 20:507-519; any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; and the like.

In certain embodiments, a subject diagnostic assay employs an antibody specific for a PEAP, wherein the antibody specific for the PEAP specifically excludes antibodies, or binding fragments thereof, having binding affinity for a polypeptide comprising the amino acid sequence set forth in SEQ ID NO:2.

Monitoring Patient Response to Treatment for a Retrovirus Infection

In some embodiments, a subject PEAP composition is useful for monitoring a patient's response to treatment for a retrovirus infection, e.g., an HIV infection. Thus, the present disclosure further provides methods for monitoring a patient's response to treatment for a *lentivirus* infection, e.g., an HIV infection. The methods generally involve contacting a white blood cell (WBC) from a patient in vitro with a disclosed PEAP; and detecting a cytokine secreted by the WBC in response to contact with the PEAP. A reduction in cytokine production by the WBC in response to contact with a PEAP is an indication that the treatment is effective in treating a *lentivirus* infection (e.g., in achieving a reduction in viral load, in achieving an increase in CD4$^+$ T lymphocyte levels (in the case of an HIV infection), and the like). Suitable WBCs include, but are not limited to, peripheral blood mononuclear cells (PBMC), isolated T lymphocytes, isolated CD4$^+$ T lymphocytes, isolated CD8$^+$ T lymphocytes, natural killer (NK) cells, natural killer T lymphocytes (NKT, e.g., NK1.1$^+$ T lymphocytes), and the like.

PEAPs suitable for use in the disclosed monitoring method can be 6 amino acids, 7 amino acids, 8 amino acids, 9 amino acids, 10 amino acids, 11 amino acids, 12 amino acids, 12-15 amino acids, 15-18 amino acids, 18-20 amino acids, or 20-25 amino acids long, or longer. Suitable PEAPs include any of the PEAPs discussed above. In some embodiments, the PEAP comprises an amino acid sequence as set forth in any one of SEQ ID NOs: 1-10.

Cytokines that are secreted from PBMCs and that are detected in a disclosed patient monitoring method include, but are not limited to, IFN-γ, TNF-α, and IL-2.

Methods for detecting secreted cytokines that are suitable for use in a disclosed patient monitoring method include, but are not limited to, immunological assays, e.g., enzyme-linked immunosorbent assay (ELISA), radioimmunoassay (RIA), an enzyme-linked immunospot (ELISPOT) assay; cellular assays; and the like.

In some embodiments, a reduction of at least about 10%, at least about 20%, at least about 30%, at least about 40%, at least about 50%, at least about 60%, at least about 70%, at least about 80%, or at least about 90% or more, in cytokine production by WBCs in response to contact with a PEAP indicates that the treatment for the *lentivirus* infection is efficacious.

Patient samples comprising white blood cells (WBCs) can be obtained before and after treatment; or at various times during the course of treatment, and the level of cytokine production compared between a sample taken at a first time point and a sample taken at a second (later) time point.

In some embodiments, PBMC obtained from a patient are contacted with one or more PEAPs in vitro; and an ELISPOT assay is used to detect cytokine production. The ELISPOT assay has been described in the art. See, e.g., Lalvani et al. (1997) *J. Exp. Med.* 186:859; and U.S. Pat. No. 5,853,697. In these embodiments, the level of cytokines produced by the PBMC is expressed as the number of spot-forming units (SFU) per $10^6$ PBMC. A reduction in the number of SFU indicates that a treatment for a *lentivirus* infection is effective.

Staging a Disease

The present disclosure provides methods of staging a disease in an individual, where the level of a PEAP or an endogenous polypeptide having an amino acid sequence substantially similar to that of a subject PEAP is associated with the stage or severity of the disease. The methods generally involve detecting the level of a PEAP or an endogenous polypeptide having an amino acid sequence substantially similar to that of a subject PEAP in a biological sample obtained from the individual. The level of the PEAP or the endogenous polypeptide having an amino acid sequence substantially similar to that of a subject PEAP in the biological sample is correlated with the severity of the disease or disorder, and used to stage the disease.

A disclosed method of staging a disease involves detecting the number of CD8$^+$ T cells, in a biological sample obtained from an individual, that are specific for a subject PEAP. In some embodiments, the number of PEAP-specific CD8$^+$ T cells is an indication of the stage of the disease.

Subjects Suitable for Treatment and/or Prophylaxis
Treatment and/or Prophylaxis of Retroviral Infection The present disclosure contemplates methods which are suitable for treating individuals who have a retroviral infection, e.g., a lentiviral infection; uninfected individuals who are at risk of contracting a retroviral infection; individuals who were treated for a retroviral infection, but failed to respond to the treatment; and individuals who were treated for a retroviral infection, but who relapsed.

Individuals suitable for treatment with a subject method of inducing an immune response to a retrovirus-infected cell, e.g., an HIV-infected cell, include naïve individuals, e.g., individuals who are not infected with HIV.

For example, the methods of the present disclosure are suitable for treating individuals who have a human immunodeficiency virus (HIV) infection (e.g., individuals who have been diagnosed as having an HIV infection); individuals who are naïve with respect to HIV infection, but who at risk of contracting an HIV infection; and individuals who were treated for an HIV infection, but who either failed to respond to the treatment, or who initially responded to treatment but subsequently relapsed. For example, a suitable subject includes an individual who has been treated with highly active antiretroviral therapy (HAART).

Subjects suitable for treatment with a subject method include, but are not limited to, uninfected individuals with healthy, intact immune systems, but who are at greater risk for becoming HIV infected ("at-risk" individuals). At-risk individuals include, but are not limited to, individuals who have a greater likelihood than the general population of becoming HIV infected. Individuals at risk for becoming HIV infected include, but are not limited to, individuals at risk for HIV infection due to sexual activity with HIV-infected individuals; intravenous drug users; individuals who may have been exposed to HIV-infected blood, blood products, or other HIV-contaminated body fluids; and babies who are being nursed by HIV-infected mothers. Individuals suitable for treatment include individuals infected with, or at risk of becoming infected with, HIV-1 and/or HIV-2 and/or HIV-3, or any variant thereof.

The above-described methods can be used to treat a human T cell leukemia virus 1 (HTLV-1) infection in an individual. Thus, a disclosed method is also suitable for treating individuals who have been infected with HTLV-1; individuals who have not yet been infected with HTLV-1, but who are at risk of becoming infected with HTLV-1; and individuals who have not yet been infected with HTLV, but who may in the future become infected with HTLV-1.

Treatment of Cancer

As discussed above, the present disclosure contemplates methods which are suitable for treating individuals who have cancer. Individuals suitable for treatment with a subject method of treating cancer include individuals having cancer wherein the cancerous state is associated with aberrant expression of an endogenous polypeptide having an amino acid sequence substantially similar to that of a subject PEAP or increased expression of an endogenous polypeptide having an amino acid sequence substantially similar to that of a subject PEAP, e.g., where the cancer comprises a cancer cell or a pre-cancerous cell that exhibits aberrant expression of an endogenous polypeptide having an amino acid sequence substantially similar to that of a subject PEAP (e.g., expresses an endogenous polypeptide having an amino acid sequence substantially similar to that of a subject PEAP at a level that is at least about 15%, at least about 25%, at least about 30%, at least about 40%, at least about 50%, at least about 75%, at least about 2-fold, at least about 5-fold, or at least about 10-fold, or more than 10-fold, higher than the level of the endogenous polypeptide having an amino acid sequence substantially similar to that of a subject PEAP expressed by a non-cancerous (normal) cell of the same cell type). Such cancers include, but are not limited to, myeloma, melanoma, ovarian cancer, breast cancer, and testicular cancer (including teratoma, seminoma, and embryonal carcinoma or mixed tumors composed of one or more of these types). As such, individuals suitable for treatment with the subject methods include, but are not limited to, individuals with myeloma, melanoma, ovarian cancer, breast cancer, and testicular cancer (including teratoma, seminoma, and embryonal carcinoma or mixed tumors composed of one or more of these types).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Identification of APOBEC Peptide Sequences which Elicit a T Cell Response in HIV Infected Subjects In order to determine whether HIV infected subjects exhibit a T cell response to APOBEC self-peptides presented on the surface of cells of HIV infected subjects, peptide epitopes from the APOBEC 3F and 3G proteins were identified and tested via ELISPOT assay as described below.

Materials/Methods

Immunogenicity prediction software (NetCTL1.2 (Larsen et al. (2005) *European Journal of Immunology* 35(8): 2295-303) was used to identify peptide epitopes from the APOBEC 3F and 3G proteins presented by HLA-A2, -B7 and -B58 superfamilies.

Top-scoring peptides (shown in Table I below) were tested, in a "pool" or individually, in an interferon-gamma (IFN-γ) ELISPOT analysis of T cell responses performed on cryopreserved PBMC.

T cell reactivity to APOBEC peptides was tested in:
1) Low risk healthy volunteers N=33 ("Healthy HIV adults" in FIG. 3);
2) Exposed through maternal route, but uninfected children N=7 ("children exposed uninfected" in FIG. 3);
3) Long term non progressors (LTNP) N=7 ("LTNP" in FIG. 3);
4) HIV-1 infected adults in primary HIV-1 infection N=13;

5) Chronically HIV-1 infected adults (low to undetectable levels of HIV-1 in the absence of any therapy ("controllers", with less than 5000 copies/ml HIV-1 plasma vial load without HAART therapy) N=19 ("chronic infection—natural controllers" in FIG. 3);

6) individuals who had higher levels of viremia ("non-controllers") N=21 ("chronic infection—viremics" in FIG. 3);

7) HAART-treated individuals with undetectable plasma HIV-1 RNA levels ("HAART suppressed") N=20 ("chronic infection—Haart suppressed" in FIGS. 3); and 8) HIV-1 vertically infected children N=73 ("children: chronic infection" in FIG. 3).

A total of 193 HIV-1 negative and positive subjects were tested in this cross sectional study.

TABLE 1

| Peptide Identifier | Amino Acid Sequence |
| --- | --- |
| A3G-A2-177 | NLPKYYILL (SEQ ID NO: 17) |
| A3G-A2-31 | NTVWLCYEV (SEQ ID NO: 18) |
| A3F-A2-194* | AMYPHIFYFHF (SEQ ID NO: 11) |
| A3F-A2-363 | FLDSKLQEI (SEQ ID NO: 12) |
| A3F-B58-159 | FVYSEGQPF (SEQ ID NO: 13) |
| A3F-B58-225 | VKHHSPVSW (SEQ ID NO: 14) |
| A3F-B58-11# | RMYRDTFSY (SEQ ID NO: 15) |
| A3G-B58-196° | RHSMDPPTFTF (SEQ ID NO: 19) |
| A3G-B58-164 | FVYSQRELF (SEQ ID NO: 20) |
| A3G-B7-2# | KPHFRNTVE (SEQ ID NO: 21) |
| A3G-B7-27° | RPILSRRNTVWL (SEQ ID NO: 22) |
| A3F-B7-43 | GPSRPRLDA (SEQ ID NO: 16) |

\* = shared epitope in different HLA supertypes
\# = shared epitope between APOBEC 3G and 3F
° = shared epitope within same protein, same HLA supertype Peptides were tested in an IFN-γ ELISPOT using cryopreserved PBMC; a positive response was considered as >50 SFU over background. Peptides were tested at a concentration of 10 μg/ml (either individually or in pools) with 100,000 PBMC per well. Spot totals for duplicate wells were averaged, and all spot numbers were normalized to numbers of IFN-γ spot-forming units (SFU) per 1×10$^6$ PBMC. Spot values from medium control wells were subtracted to determine responses to each polypeptide, with a minimum response value of 50 SFU/10$^6$ PBMC.

Results

A table showing patient characteristics and APOBEC polypeptide pool responses is set forth in FIG. 3. 2/33 HIV-1 negative low risk volunteers and 0/7 exposed uninfected children had responses to the pool of APOBEC peptides (FIG. 3). 5/7 of the LTNP had responses to the APOBEC peptide pool with a mean of 486 SFU/10$^6$ PBMC (FIG. 3). In primary HIV-1 infected subjects, 5/13 had responses, with a lower mean of 84 SFU/10$^6$ PBMC. The cohort of chronically infected subjects had the lowest responses of all HIV-1 infected people. The non controllers had the lowest mean T cell response to the APOBEC pool (34 SFU/10$^6$ PBMC), although there was no statistically difference compared to the HAART suppressed group (54 SFU/10$^6$ PBMC), or the controllers (45 SFU/10$^6$ PBMC). There were 13/77 responders in the group of HIV-1 infected children (88 SFU/10$^6$ PBMC).

Figure 4:
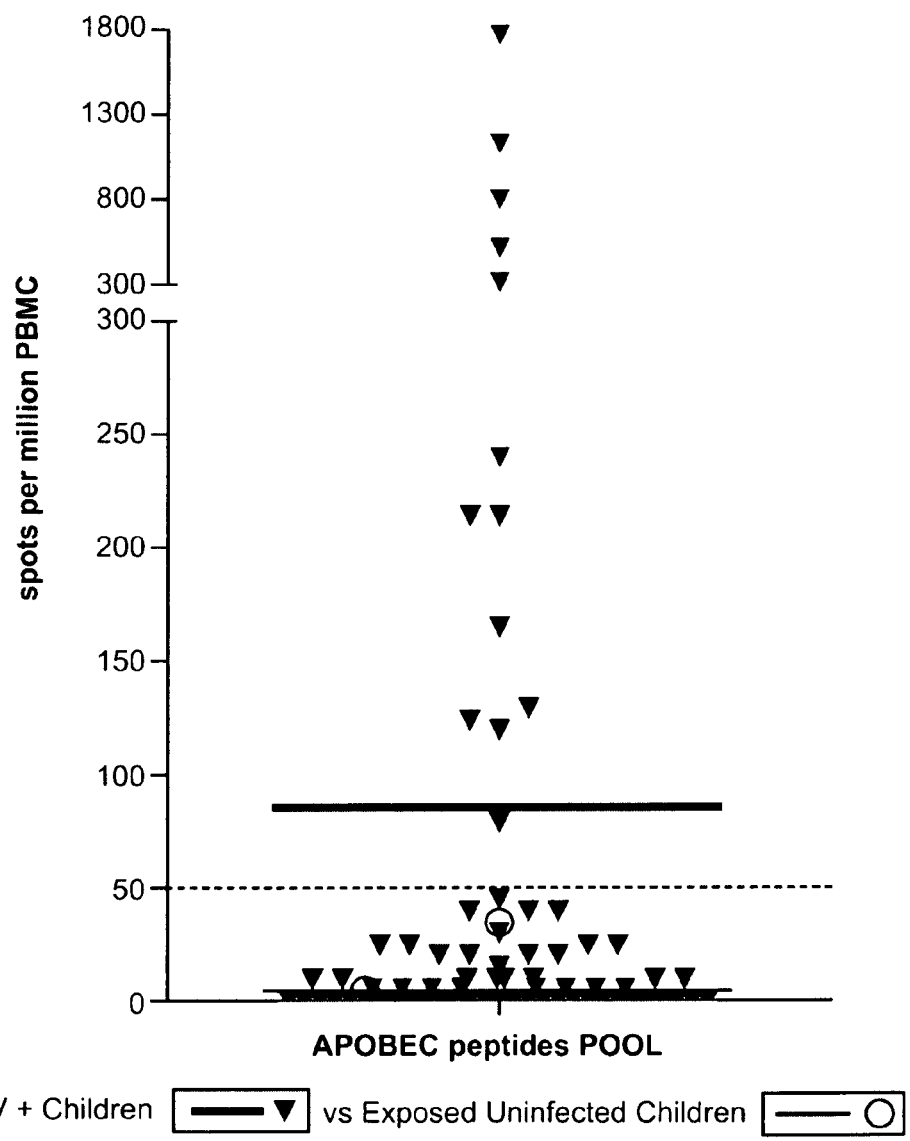
FIG. 4 provides a graph showing T cell responses to an APOBEC polypeptide pool in HIV-1 positive children (black triangles) and exposed uninfected children (white circles) measured by interferon-γ ELISPOT. The horizontal lines represent the mean SFU/$10^6$ PBMC for HIV-1 positive children and HIV-1 negative children respectively.

Specific ELISPOT results for HIV-1 positive children (black triangles) and exposed uninfected children (white circles) are provided in FIG. 4. The horizontal lines represent the mean SFU/10$^6$ PBMC for HIV-1 positive children and HIV-1 negative children respectively. The results of these experiments indicate that peptides derived from APOBEC 3F and 3G are immunogenic in the context of HIV-1 infection.

Figure 5:
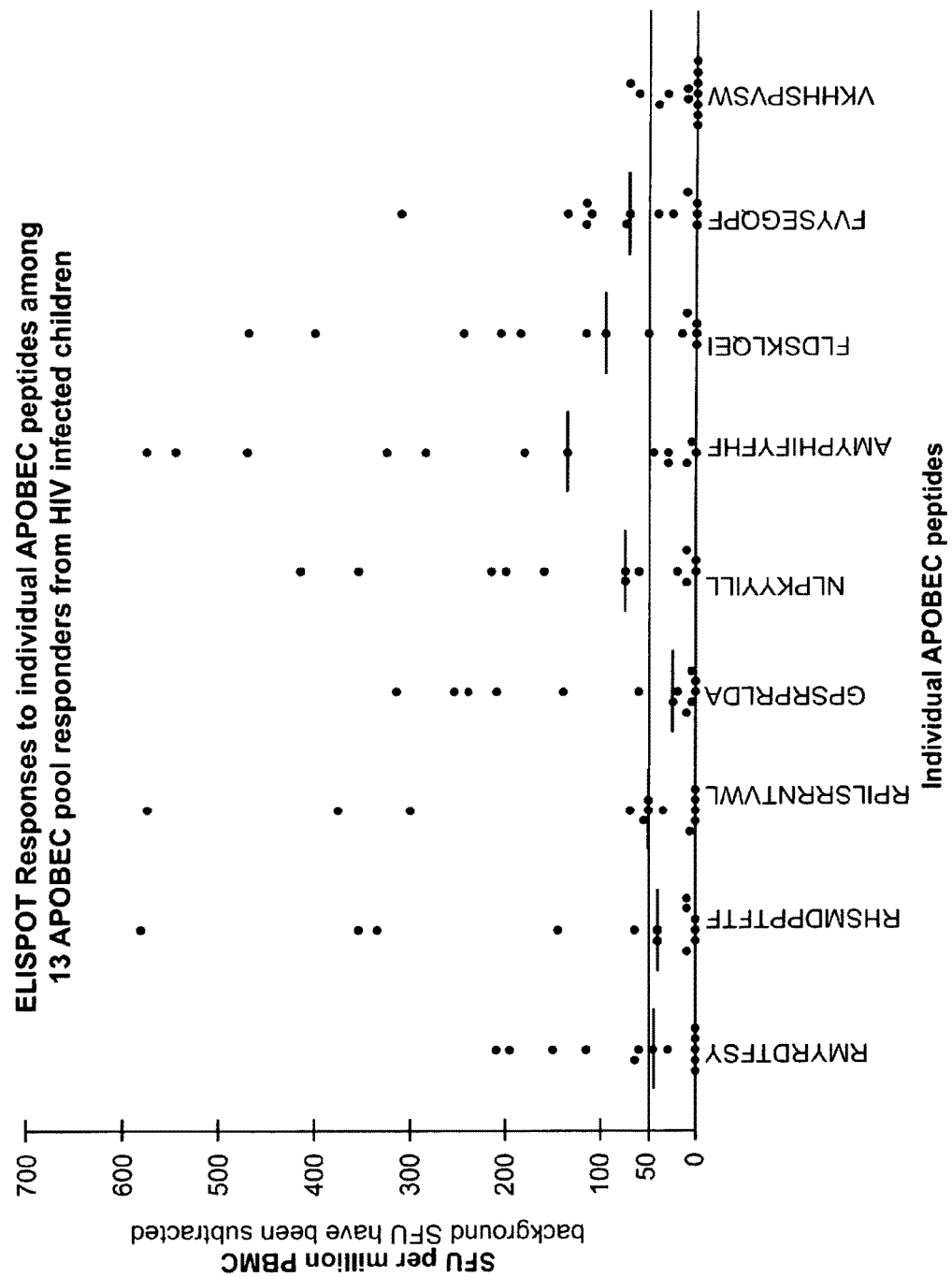
FIG. 5 presents ELISPOT responses of peripheral blood mononuclear cells (PBMC) from HIV-infected children to individual APOBEC peptides: RMYRDTFSY (SEQ ID NO:15); RHSMDPPTFTF (SEQ ID NO:19); RPILSRRNT-VWL (SEQ ID NO:22); GPSRPRLDA (SEQ ID NO:16); NLPKYYILL (SEQ ID NO:17; AMYPHIFYFHF (SEQ ID NO:11; FLDSKLQEI (SEQ ID NO:12); FVYSEGQPF (SEQ ID NO:13); and VKHHSPVSW (SEQ ID NO:14).

ELISPOT results for HIV-infected children to individual APOBEC peptides from among the 13 APOBEC pool responders are shown in FIG. 5.

Example 2

T Cell Responses Against APOBEC Proteins are CD8 Mediated

Materials/Methods

APOBEC polypeptides were identified as indicated in Example 1 above. PBMCs from HIV-1-infected individuals were stimulated with or without the pool of twelve APOBEC peptides for six hours with anti-CD28, anti-CD49d, and brefeldin A. The cells were stained with fluorophore-conjugated antibodies to CD3, CD4, CD8, and interferon-γ to determine phenotype and function and an amine dye to discriminate between live and dead cells. Data were acquired with a LSR-II system. At least 100,000 events were collected and analyzed with FlowJo software.

Results

Figure 6:
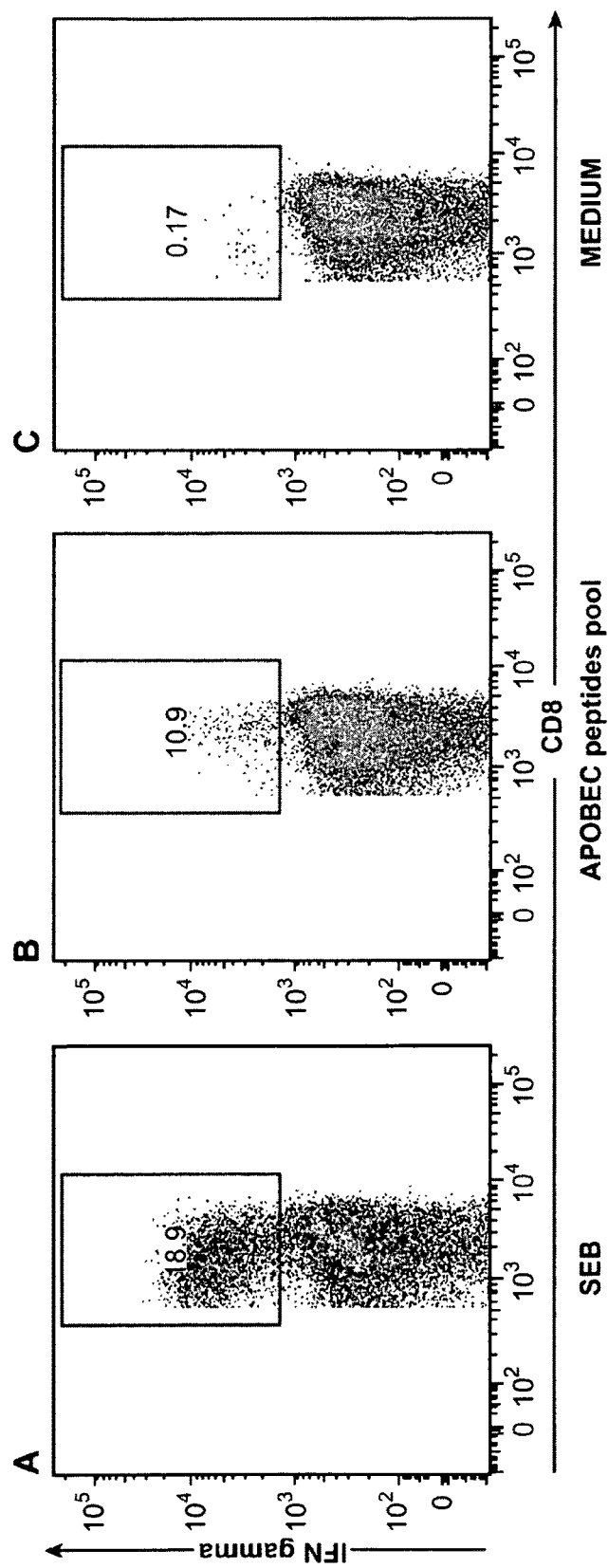
FIG. 6 provides fluorescence activated cell sorting data for T cell responses in an HIV-1 positive child against the APOBEC polypeptide pool.

The results demonstrate that T cell responses against APOBEC polypeptides are CD8 mediated. In one specific example, FIG. 6 shows T cell responses for an HIV-1 positive child against the APOBEC peptides pool.

Additional results for both pooled and individual APOBC polypeptides are provided in FIGS. 7-14. Some of the data are represented graphically in FIG. 15.

Figure 15:
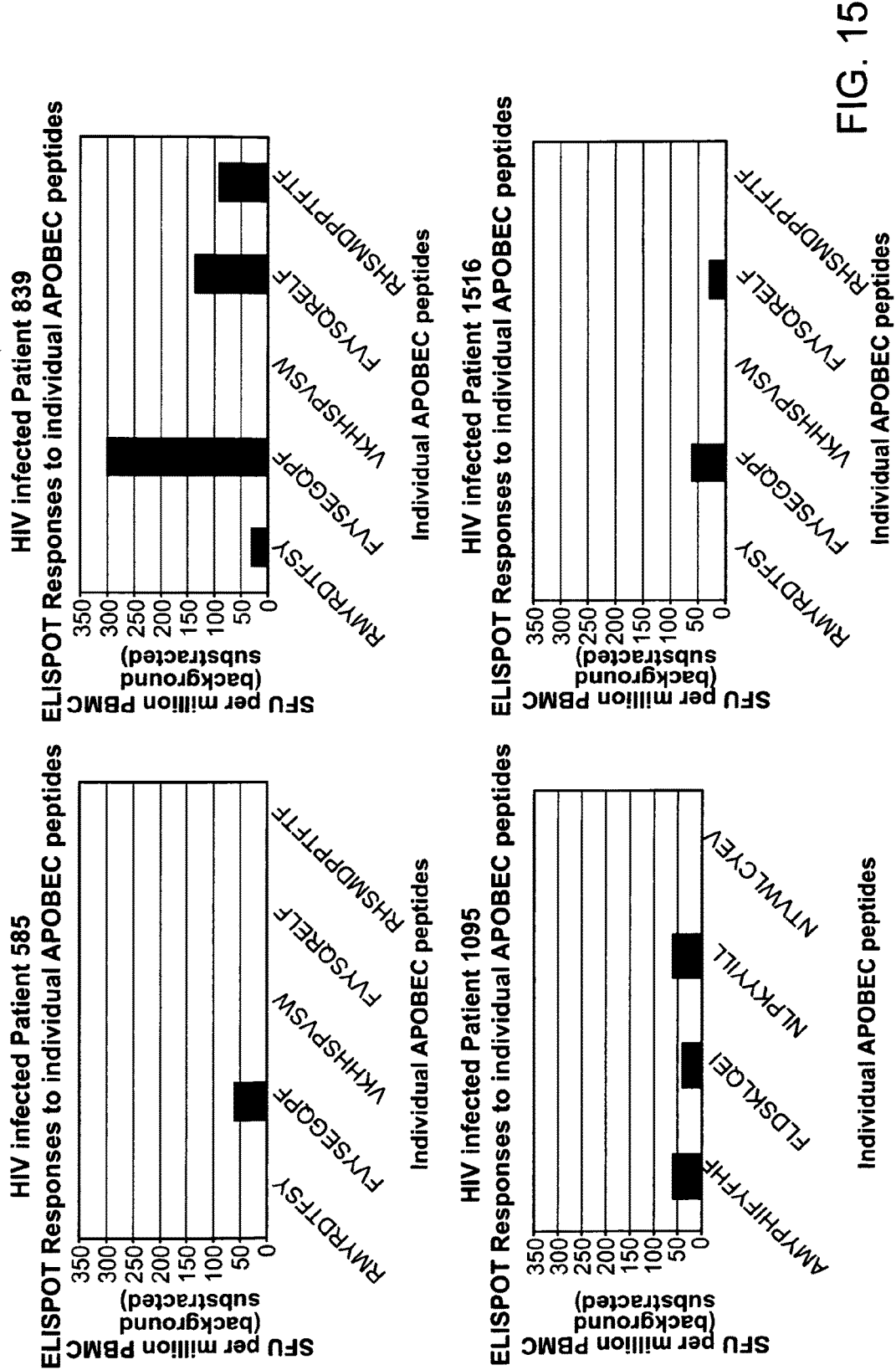
FIG. 15 presents ELISPOT responses of peripheral blood mononuclear cells (PBMC) from HIV-infected adults to individual APOBEC peptides. The peptides used in the assay were: AMYPHIFYFHF (SEQ ID NO:11); FLDSKLQEI (SEQ ID NO:12); FVYSEGQPF (SEQ ID NO:13); VKHHSPVSW (SEQ ID NO:14); RMYRDTFSY (SEQ ID NO:15); GPSRPRLDA (SEQ ID NO:16); NLPKYYILL (SEQ ID NO:17); NTVWLCYEV (SEQ ID NO:18); RHSMDPPTFTF (SEQ ID NO:19); FVYSQRELF (SEQ ID NO:20); and RPILSRRNTVWL (SEQ ID NO:22).

FIG. 15 presents ELISPOT responses of peripheral PMBC from HIV-infected adults to individual APOBEC peptides. Seven HIV-1 infected adults were tested individually against individual APOBEC peptides. Each graph represents responses of an individual adult. Peptide sequences are shown below the bars. Each bar corresponds to the interferon gamma ELISPOT T cell response of the individual to an individual peptide. The absence of a bar indicates absence of a significant response above the "medium" control.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of inducing a T lymphocyte response in an individual to a host cell infected with a human immunodeficiency virus (HIV), the method comprising administering to the individual an immunogenic composition comprising a polypeptide consisting of from 9 amino acids to about 150 amino acids, wherein said polypeptide comprises the amino acid sequence of one of SEQ ID NOs:11-14, and 16.

2. The method of claim 1, wherein the composition is formulated for parenteral administration or for administration to a mucosal tissue.

3. The method of claim 1, wherein the composition comprises an adjuvant comprising aluminum hydroxide, MF59, or monophosphoryl lipid A.

4. The method of claim 1, wherein the T lymphocyte response comprises a CD8+ T cell response, a CD4+ T cell response, or a mucosal T lymphocyte response.

5. The method of claim 1, wherein the HIV is HIV-1.

6. The method of claim 1, wherein the polypeptide is multimerized.

7. The method of claim 1, wherein the polypeptide comprises the amino acid sequence of SEQ ID NO:11.

8. The method of claim 1, wherein the polypeptide comprises the amino acid sequence of SEQ ID NO:12.

9. The method of claim 1, wherein the polypeptide comprises the amino acid sequence of SEQ ID NO:13.

10. The method of claim 1, wherein the polypeptide comprises the amino acid sequence of SEQ ID NO:14.

11. The method of claim 1, wherein the polypeptide comprises the amino acid sequence of SEQ ID NO:16.

12. The method of claim 1, wherein the individual has been diagnosed as having an HIV infection.

13. The method of claim 1, wherein the polypeptide has a length of from about 15 amino acids to about 50 amino acids.

* * * * *

SEQUENCE LISTING

<160> NUMBER OF SEQ ID NOS: 24

<210> SEQ ID NO 1
<211> LENGTH: 236
<212> TYPE: PRT
<213> ORGANISM: Homo sapiens

<400> SEQUENCE: 1

Met Thr Ser Glu Lys Gly Pro Ser Thr Gly Asp Pro Thr Leu Arg Arg
 1               5                  10                  15

Arg Ile Glu Pro Trp Glu Phe Asp Val Phe Tyr Asp Pro Arg Glu Leu
                20                  25                  30

Arg Lys Glu Ala Cys Leu Leu Tyr Glu Ile Lys Trp Gly Met Ser Arg
            35                  40                  45

Lys Ile Trp Arg Ser Ser Gly Lys Asn Thr Thr Asn His Val Glu Val
        50                  55                  60

Asn Phe Ile Lys Lys Phe Thr Ser Glu Arg Asp Phe His Pro Ser Met
65                  70                  75                  80

Ser Cys Ser Ile Thr Trp Phe Leu Ser Trp Ser Pro Cys Trp Glu Cys
                85                  90                  95

Ser Gln Ala Ile Arg Glu Phe Leu Ser Arg His Pro Gly Val Thr Leu
            100                 105                 110

Val Ile Tyr Val Ala Arg Leu Phe Trp His Met Asp Gln Gln Asn Arg
        115                 120                 125

Gln Gly Leu Arg Asp Leu Val Asn Ser Gly Val Thr Ile Gln Ile Met
    130                 135                 140

Arg Ala Ser Glu Tyr Tyr His Cys Trp Arg Asn Phe Val Asn Tyr Pro
145                 150                 155                 160

Pro Gly Asp Glu Ala His Trp Pro Gln Tyr Pro Pro Leu Trp Met Met
                165                 170                 175

Leu Tyr Ala Leu Glu Leu His Cys Ile Ile Leu Ser Leu Pro Pro Cys
            180                 185                 190

Leu Lys Ile Ser Arg Arg Trp Gln Asn His Leu Thr Phe Phe Arg Leu
        195                 200                 205

His Leu Gln Asn Cys His Tyr Gln Thr Ile Pro Pro His Ile Leu Leu
    210                 215                 220

Ala Thr Gly Leu Ile His Pro Ser Val Ala Trp Arg
225                 230                 235

<210> SEQ ID NO 2
<211> LENGTH: 198
<212> TYPE: PRT
<213> ORGANISM: Homo sapiens

<400> SEQUENCE: 2

Met Asp Ser Leu Leu Met Asn Arg Arg Lys Phe Leu Tyr Gln Phe Lys
 1               5                  10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp

```
                85                  90                  95
Phe Leu Arg Gly Asn Pro Asn Leu Ser Leu Arg Ile Phe Thr Ala Arg
            100                 105                 110
Leu Tyr Phe Cys Glu Asp Arg Lys Ala Glu Pro Glu Gly Leu Arg Arg
        115                 120                 125
Leu His Arg Ala Gly Val Gln Ile Ala Ile Met Thr Phe Lys Asp Tyr
    130                 135                 140
Phe Tyr Cys Trp Asn Thr Phe Val Glu Asn His Glu Arg Thr Phe Lys
145                 150                 155                 160
Ala Trp Glu Gly Leu His Glu Asn Ser Val Arg Leu Ser Arg Gln Leu
                165                 170                 175
Arg Arg Ile Leu Leu Pro Leu Tyr Glu Val Asp Asp Leu Arg Asp Ala
            180                 185                 190
Phe Arg Thr Leu Gly Leu
            195

<210> SEQ ID NO 3
<211> LENGTH: 199
<212> TYPE: PRT
<213> ORGANISM: Homo sapiens

<400> SEQUENCE: 3

Met Glu Ala Ser Pro Ala Ser Gly Pro Arg His Leu Met Asp Pro His
1               5                   10                  15
Ile Phe Thr Ser Asn Phe Asn Asn Gly Ile Gly Arg His Lys Thr Tyr
                20                  25                  30
Leu Cys Tyr Glu Val Glu Arg Leu Asp Asn Gly Thr Ser Val Lys Met
            35                  40                  45
Asp Gln His Arg Gly Phe Leu His Asn Gln Ala Lys Asn Leu Leu Cys
        50                  55                  60
Gly Phe Tyr Gly Arg His Ala Glu Leu Arg Phe Leu Asp Leu Val Pro
65                  70                  75                  80
Ser Leu Gln Leu Asp Pro Ala Gln Ile Tyr Arg Val Thr Trp Phe Ile
                85                  90                  95
Ser Trp Ser Pro Cys Phe Ser Trp Gly Cys Ala Gly Glu Val Arg Ala
            100                 105                 110
Phe Leu Gln Glu Asn Thr His Val Arg Leu Arg Ile Phe Ala Ala Arg
        115                 120                 125
Ile Tyr Asp Tyr Asp Pro Leu Tyr Lys Glu Ala Leu Gln Met Leu Arg
    130                 135                 140
Asp Ala Gly Ala Gln Val Ser Ile Met Thr Tyr Asp Glu Phe Lys His
145                 150                 155                 160
Cys Trp Asp Thr Phe Val Asp His Gln Gly Cys Pro Phe Gln Pro Trp
                165                 170                 175
Asp Gly Leu Asp Glu His Ser Gln Ala Leu Ser Gly Arg Leu Arg Ala
            180                 185                 190
Ile Leu Gln Asn Gln Gly Asn
        195

<210> SEQ ID NO 4
<211> LENGTH: 382
<212> TYPE: PRT
<213> ORGANISM: Homo sapiens

<400> SEQUENCE: 4

Met Asn Pro Gln Ile Arg Asn Pro Met Glu Arg Met Tyr Arg Asp Thr
```

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |

Phe Tyr Asp Asn Phe Glu Asn Glu Pro Ile Leu Tyr Gly Arg Ser Tyr
                20                  25                  30

Thr Trp Leu Cys Tyr Glu Val Lys Ile Lys Arg Gly Arg Ser Asn Leu
                35                  40                  45

Leu Trp Asp Thr Gly Val Phe Arg Gly Gln Val Tyr Phe Lys Pro Gln
                50                  55                  60

Tyr His Ala Glu Met Cys Phe Leu Ser Trp Phe Cys Gly Asn Gln Leu
 65                 70                  75                  80

Pro Ala Tyr Lys Cys Phe Gln Ile Thr Trp Phe Val Ser Trp Thr Pro
                85                  90                  95

Cys Pro Asp Cys Val Ala Lys Leu Ala Glu Phe Leu Ser Glu His Pro
                100                 105                 110

Asn Val Thr Leu Thr Ile Ser Ala Ala Arg Leu Tyr Tyr Tyr Trp Glu
                115                 120                 125

Arg Asp Tyr Arg Arg Ala Leu Cys Arg Leu Ser Gln Ala Gly Ala Arg
                130                 135                 140

Val Thr Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
                165                 170                 175

Asn Tyr Ala Phe Leu His Arg Thr Leu Lys Glu Ile Leu Arg Tyr Leu
                180                 185                 190

Met Asp Pro Asp Thr Phe Thr Phe Asn Phe Asn Asn Asp Pro Leu Val
                195                 200                 205

Leu Arg Arg Arg Gln Thr Tyr Leu Cys Tyr Glu Val Glu Arg Leu Asp
                210                 215                 220

Asn Gly Thr Trp Val Leu Met Asp Gln His Met Gly Phe Leu Cys Asn
225                 230                 235                 240

Glu Ala Lys Asn Leu Leu Cys Gly Phe Tyr Gly Arg His Ala Glu Leu
                245                 250                 255

Arg Phe Leu Asp Leu Val Pro Ser Leu Gln Leu Asp Pro Ala Gln Ile
                260                 265                 270

Tyr Arg Val Thr Trp Phe Ile Ser Trp Ser Pro Cys Phe Ser Trp Gly
                275                 280                 285

Cys Ala Gly Glu Val Arg Ala Phe Leu Gln Glu Asn Thr His Val Arg
                290                 295                 300

Leu Arg Ile Phe Ala Ala Arg Ile Tyr Asp Tyr Asp Pro Leu Tyr Lys
305                 310                 315                 320

Glu Ala Leu Gln Met Leu Arg Asp Ala Gly Ala Gln Val Ser Ile Met
                325                 330                 335

Thr Tyr Asp Glu Phe Glu Tyr Cys Trp Asp Thr Phe Val Tyr Arg Gln
                340                 345                 350

Gly Cys Pro Phe Gln Pro Trp Asp Gly Leu Glu Glu His Ser Gln Ala
                355                 360                 365

Leu Ser Gly Arg Leu Arg Ala Ile Leu Gln Asn Gln Gly Asn
                370                 375                 380

<210> SEQ ID NO 5
<211> LENGTH: 294
<212> TYPE: PRT
<213> ORGANISM: Homo sapiens

<400> SEQUENCE: 5

```
Met Asn Pro Gln Ile Arg Asn Pro Met Lys Ala Met Tyr Pro Gly Thr
1               5                  10                 15

Phe Tyr Phe Gln Phe Lys Asn Leu Trp Glu Ala Asn Asp Arg Asn Glu
            20                 25                 30

Thr Trp Leu Cys Phe Thr Val Glu Gly Ile Lys Arg Arg Ser Val Val
            35                 40                 45

Ser Trp Lys Thr Gly Val Phe Arg Asn Gln Val Asp Ser Glu Thr His
50                  55                 60

Cys His Ala Glu Arg Cys Phe Leu Ser Trp Phe Cys Asp Asp Ile Leu
65                  70                 75                 80

Ser Pro Asn Thr Lys Tyr Gln Val Thr Trp Tyr Thr Ser Trp Ser Pro
            85                 90                 95

Cys Pro Asp Cys Ala Gly Glu Val Ala Glu Phe Leu Ala Arg His Ser
            100                105                110

Asn Val Asn Leu Thr Ile Phe Thr Ala Arg Leu Tyr Tyr Phe Gln Tyr
            115                120                125

Pro Cys Tyr Gln Glu Gly Leu Arg Ser Leu Ser Gln Glu Gly Val Ala
            130                135                140

Val Glu Ile Met Asp Tyr Glu Asp Phe Lys Tyr Cys Trp Glu Asn Phe
145                 150                155                160

Val Tyr Asn Asp Asn Glu Pro Phe Lys Pro Trp Glu Gly Ile Lys Asn
            165                170                175

Gln Leu Ser Thr Ser Glu Lys Lys Ala Thr Gly Glu Ser Pro Val Arg
            180                185                190

Gly Leu Pro Gly Pro His Gly Leu Ser Pro Leu Ala Ser Cys Ser Cys
            195                200                205

Cys Thr Gly Leu Pro Ser Thr Leu Asp Pro Leu Cys Phe Cys Leu Val
210                 215                220

Ile Leu Ser Pro Ser Trp Pro Gln Gly His Ser Thr Val Leu Pro Cys
225                 230                235                240

Leu Thr Ala Ser Ser Ser Leu Phe Gln Thr Leu Pro Ala Glu Ala Pro
            245                250                255

Phe Cys Leu His Gly Tyr Pro Ser Thr Pro Thr Asp Pro Val Pro Pro
            260                265                270

Ala Cys Val Pro Leu Thr Trp Leu Phe Pro Ser Pro Gln His Asn Gln
            275                280                285

Ile Leu Leu Asn Ser Cys
            290

<210> SEQ ID NO 6
<211> LENGTH: 386
<212> TYPE: PRT
<213> ORGANISM: Homo sapiens

<400> SEQUENCE: 6

Met Asn Pro Gln Ile Arg Asn Pro Met Glu Arg Met Tyr Arg Asp Thr
1               5                  10                 15

Phe Tyr Asp Asn Phe Glu Asn Glu Pro Ile Leu Tyr Gly Arg Ser Tyr
            20                 25                 30

Thr Trp Leu Cys Tyr Glu Val Lys Ile Lys Arg Gly Arg Ser Asn Leu
            35                 40                 45

Leu Trp Asp Thr Gly Val Phe Arg Gly Pro Val Leu Pro Lys Arg Gln
50                  55                 60

Ser Asn His Arg Gln Glu Val Tyr Phe Arg Phe Glu Asn His Ala Glu
65                  70                 75                 80
```

Met Cys Phe Leu Ser Trp Phe Cys Gly Asn Arg Leu Pro Ala Asn Arg
                85                  90                  95

Arg Phe Gln Ile Thr Trp Phe Val Ser Trp Asn Pro Cys Leu Pro Cys
            100                 105                 110

Val Val Lys Val Thr Lys Phe Leu Ala Glu His Pro Asn Val Thr Leu
        115                 120                 125

Thr Ile Ser Ala Ala Arg Leu Tyr Tyr Tyr Arg Asp Arg Asp Trp Arg
    130                 135                 140

Trp Val Leu Leu Arg Leu His Lys Ala Gly Ala Arg Val Lys Ile Met
145                 150                 155                 160

Asp Tyr Glu Asp Phe Ala Tyr Cys Trp Glu Asn Phe Val Cys Asn Glu
                165                 170                 175

Gly Gln Pro Phe Met Pro Trp Tyr Lys Phe Asp Asp Asn Tyr Ala Ser
            180                 185                 190

Leu His Arg Thr Leu Lys Glu Ile Leu Arg Asn Pro Met Glu Ala Met
        195                 200                 205

Tyr Pro His Ile Phe Tyr Phe His Phe Lys Asn Leu Leu Lys Ala Cys
    210                 215                 220

Gly Arg Asn Glu Ser Trp Leu Cys Phe Thr Met Glu Val Thr Lys His
225                 230                 235                 240

His Ser Ala Val Phe Arg Lys Arg Gly Val Phe Arg Asn Gln Val Asp
                245                 250                 255

Pro Glu Thr His Cys His Ala Glu Arg Cys Phe Leu Ser Trp Phe Cys
            260                 265                 270

Asp Asp Ile Leu Ser Pro Asn Thr Asn Tyr Glu Val Thr Trp Tyr Thr
        275                 280                 285

Ser Trp Ser Pro Cys Pro Glu Cys Ala Gly Glu Val Ala Glu Phe Leu
    290                 295                 300

Ala Arg His Ser Asn Val Asn Leu Thr Ile Phe Thr Ala Arg Leu Cys
305                 310                 315                 320

Tyr Phe Trp Asp Thr Asp Tyr Gln Glu Gly Leu Cys Ser Leu Ser Gln
                325                 330                 335

Glu Gly Ala Ser Val Lys Ile Met Gly Tyr Lys Asp Phe Val Ser Cys
            340                 345                 350

Trp Lys Asn Phe Val Tyr Ser Asp Asp Glu Pro Phe Lys Pro Trp Lys
        355                 360                 365

Gly Leu Gln Thr Asn Phe Arg Leu Leu Lys Arg Arg Leu Arg Glu Ile
    370                 375                 380

Leu Gln
385

<210> SEQ ID NO 7
<211> LENGTH: 373
<212> TYPE: PRT
<213> ORGANISM: Homo sapiens

<400> SEQUENCE: 7

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Arg
        35                  40                  45

Leu Asp Ala Lys Ile Phe Arg Gly Gln Val Tyr Ser Gln Pro Glu His

```
                 50                  55                  60
His Ala Glu Met Cys Phe Leu Ser Trp Phe Cys Gly Asn Gln Leu Pro
 65                  70                  75                  80

Ala Tyr Lys Cys Phe Gln Ile Thr Trp Phe Val Ser Trp Thr Pro Cys
                 85                  90                  95

Pro Asp Cys Val Ala Lys Leu Ala Glu Phe Leu Ser Glu His Pro Asn
                100                 105                 110

Val Thr Leu Thr Ile Ser Ala Ala Arg Leu Tyr Tyr Tyr Trp Glu Arg
                115                 120                 125

Asp Tyr Arg Arg Ala Leu Cys Arg Leu Ser Gln Ala Gly Ala Arg Val
                130                 135                 140

Lys Ile Met Asp Asp Glu Glu Phe Ala Tyr Cys Trp Glu Asn Phe Val
145                 150                 155                 160

Tyr Ser Glu Gly Gln Pro Phe Met Pro Trp Tyr Lys Phe Asp Asp Asn
                165                 170                 175

Tyr Ala Phe Leu His Arg Thr Leu Lys Glu Ile Leu Arg Asn Pro Met
                180                 185                 190

Glu Ala Met Tyr Pro His Ile Phe Tyr Phe His Phe Lys Asn Leu Arg
                195                 200                 205

Lys Ala Tyr Gly Arg Asn Glu Ser Trp Leu Cys Phe Thr Met Glu Val
210                 215                 220

Val Lys His His Ser Pro Ile Ser Trp Lys Arg Gly Val Phe Arg Asn
225                 230                 235                 240

Gln Val Asp Pro Glu Thr His Cys His Ala Glu Arg Cys Phe Leu Ser
                245                 250                 255

Trp Phe Cys Asp Asp Ile Leu Ser Pro Asn Thr Asn Tyr Glu Val Thr
                260                 265                 270

Trp Tyr Thr Ser Trp Ser Pro Cys Pro Glu Cys Ala Gly Glu Val Ala
                275                 280                 285

Glu Phe Leu Ala Arg His Ser Asn Val Asn Leu Thr Ile Phe Thr Ala
                290                 295                 300

Arg Leu Tyr Tyr Phe Trp Asp Thr Asp Tyr Gln Glu Gly Leu Arg Ser
305                 310                 315                 320

Leu Ser Gln Glu Gly Ala Ser Val Glu Ile Met Gly Tyr Lys Asp Phe
                325                 330                 335

Lys Tyr Cys Trp Glu Asn Phe Val Tyr Asn Asp Asp Gly Pro Phe Lys
                340                 345                 350

Pro Trp Lys Gly Leu Lys Tyr Asn Phe Leu Phe Leu Asp Ser Lys Leu
                355                 360                 365

Gln Glu Ile Leu Glu
                370

<210> SEQ ID NO 8
<211> LENGTH: 384
<212> TYPE: PRT
<213> ORGANISM: Homo sapiens

<400> SEQUENCE: 8

Met Lys Pro His Phe Arg Asn Thr Val Glu Arg Met Tyr Arg Asp Thr
 1                5                  10                  15

Phe Ser Tyr Asn Phe Tyr Asn Arg Pro Ile Leu Ser Arg Arg Asn Thr
                 20                  25                  30

Val Trp Leu Cys Tyr Glu Val Lys Thr Lys Gly Pro Ser Arg Pro Pro
                 35                  40                  45
```

Leu Asp Ala Lys Ile Phe Arg Gly Gln Val Tyr Ser Glu Leu Lys Tyr
 50                  55                  60

His Pro Glu Met Arg Phe Phe His Trp Phe Ser Lys Trp Arg Lys Leu
 65                  70                  75                  80

His Arg Asp Gln Glu Tyr Glu Val Thr Trp Tyr Ile Ser Trp Ser Pro
                 85                  90                  95

Cys Thr Lys Cys Thr Arg Asp Met Ala Thr Phe Leu Ala Glu Asp Pro
            100                 105                 110

Lys Val Thr Leu Thr Ile Phe Val Ala Arg Leu Tyr Tyr Phe Trp Asp
        115                 120                 125

Pro Asp Tyr Gln Glu Ala Leu Arg Ser Leu Cys Gln Lys Arg Asp Gly
130                 135                 140

Pro Arg Ala Thr Met Lys Ile Met Asn Tyr Asp Glu Phe Gln His Cys
145                 150                 155                 160

Trp Ser Lys Phe Val Tyr Ser Gln Arg Glu Leu Phe Glu Pro Trp Asn
                165                 170                 175

Asn Leu Pro Lys Tyr Tyr Ile Leu Leu His Ile Met Leu Gly Glu Ile
            180                 185                 190

Leu Arg His Ser Met Asp Pro Pro Thr Phe Thr Phe Asn Phe Asn Asn
        195                 200                 205

Glu Pro Trp Val Arg Gly Arg His Glu Thr Tyr Leu Cys Tyr Glu Val
210                 215                 220

Glu Arg Met His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                245                 250                 255

His Ala Glu Leu Cys Phe Leu Asp Val Ile Pro Phe Trp Lys Leu Asp
            260                 265                 270

Leu Asp Gln Asp Tyr Arg Val Thr Cys Phe Thr Ser Trp Ser Pro Cys
        275                 280                 285

Phe Ser Cys Ala Gln Glu Met Ala Lys Phe Ile Ser Lys Asn Lys His
290                 295                 300

Val Ser Leu Cys Ile Phe Thr Ala Arg Ile Tyr Asp Asp Gln Gly Arg
305                 310                 315                 320

Cys Gln Glu Gly Leu Arg Thr Leu Ala Glu Ala Gly Ala Lys Ile Ser
                325                 330                 335

Ile Met Thr Tyr Ser Glu Phe Lys His Cys Trp Asp Thr Phe Val Asp
            340                 345                 350

His Gln Gly Cys Pro Phe Gln Pro Trp Asp Gly Leu Asp Glu His Ser
        355                 360                 365

Gln Asp Leu Ser Gly Arg Leu Arg Ala Ile Leu Gln Asn Gln Glu Asn
370                 375                 380

<210> SEQ ID NO 9
<211> LENGTH: 182
<212> TYPE: PRT
<213> ORGANISM: Homo sapiens

<400> SEQUENCE: 9

Met Ala Leu Leu Thr Ala Glu Thr Phe Arg Leu Gln Phe Asn Asn Lys
 1               5                  10                  15

Arg Arg Leu Arg Arg Pro Tyr Tyr Pro Arg Lys Ala Leu Leu Cys Tyr
                20                  25                  30

Gln Leu Thr Pro Gln Asn Gly Ser Thr Pro Thr Arg Gly Tyr Phe Glu
        35                  40                  45

```
Asn Lys Lys Lys Cys His Ala Glu Ile Cys Phe Ile Asn Glu Ile Lys
 50                  55                  60

Ser Met Gly Leu Asp Glu Thr Gln Cys Tyr Gln Val Thr Cys Tyr Leu
 65                  70                  75                  80

Thr Trp Ser Pro Cys Ser Ser Cys Ala Trp Glu Leu Val Asp Phe Ile
                 85                  90                  95

Lys Ala His Asp His Leu Asn Leu Gly Ile Phe Ala Ser Arg Leu Tyr
            100                 105                 110

Tyr His Trp Cys Lys Pro Gln Gln Lys Gly Leu Arg Leu Leu Cys Gly
        115                 120                 125

Ser Gln Val Pro Val Glu Val Met Gly Phe Pro Glu Phe Ala Asp Cys
130                 135                 140

Trp Glu Asn Phe Val Asp His Glu Lys Pro Leu Ser Phe Asn Pro Tyr
145                 150                 155                 160

Lys Met Leu Glu Glu Leu Asp Lys Asn Ser Arg Ala Ile Lys Arg Arg
                165                 170                 175

Leu Glu Arg Ile Lys Ser
            180

<210> SEQ ID NO 10
<211> LENGTH: 367
<212> TYPE: PRT
<213> ORGANISM: Homo sapiens

<400> SEQUENCE: 10

Met Glu Pro Ile Tyr Glu Glu Tyr Leu Ala Asn His Gly Thr Ile Val
 1               5                  10                  15

Lys Pro Tyr Tyr Trp Leu Ser Phe Ser Leu Asp Cys Ser Asn Cys Pro
                20                  25                  30

Tyr His Ile Arg Thr Gly Glu Glu Ala Arg Val Ser Leu Thr Glu Phe
            35                  40                  45

Cys Gln Ile Phe Gly Phe Pro Tyr Gly Thr Thr Phe Pro Gln Thr Lys
 50                  55                  60

His Leu Thr Phe Tyr Glu Leu Lys Thr Ser Ser Gly Ser Leu Val Gln
 65                  70                  75                  80

Lys Gly His Ala Ser Ser Cys Thr Gly Asn Tyr Ile His Pro Glu Ser
                 85                  90                  95

Met Leu Phe Glu Met Asn Gly Tyr Leu Asp Ser Ala Ile Tyr Asn Asn
            100                 105                 110

Asp Ser Ile Arg His Ile Ile Leu Tyr Ser Asn Asn Ser Pro Cys Asn
        115                 120                 125

Glu Ala Asn His Cys Cys Ile Ser Lys Met Tyr Asn Phe Leu Ile Thr
130                 135                 140

Tyr Pro Gly Ile Thr Leu Ser Ile Tyr Phe Ser Gln Leu Tyr His Thr
145                 150                 155                 160

Glu Met Asp Phe Pro Ala Ser Ala Trp Asn Arg Glu Ala Leu Arg Ser
                165                 170                 175

Leu Ala Ser Leu Trp Pro Arg Val Val Leu Ser Pro Ile Ser Gly Gly
            180                 185                 190

Ile Trp His Ser Val Leu His Ser Phe Ile Ser Gly Val Ser Gly Ser
        195                 200                 205

His Val Phe Gln Pro Ile Leu Thr Gly Arg Ala Leu Ala Asp Arg His
210                 215                 220

Asn Ala Tyr Glu Ile Asn Ala Ile Thr Gly Val Lys Pro Tyr Phe Thr
```

```
            225                 230                 235                 240
Asp Val Leu Leu Gln Thr Lys Arg Asn Pro Asn Thr Lys Ala Gln Glu
                    245                 250                 255

Ala Leu Glu Ser Tyr Pro Leu Asn Asn Ala Phe Pro Gly Gln Phe Phe
                260                 265                 270

Gln Met Pro Ser Gly Gln Leu Gln Pro Asn Leu Pro Asp Leu Arg
            275                 280                 285

Ala Pro Val Val Phe Val Leu Val Pro Leu Arg Asp Leu Pro Pro Met
        290                 295                 300

His Met Gly Gln Asn Pro Asn Lys Pro Arg Asn Ile Val Arg His Leu
305                 310                 315                 320

Asn Met Pro Gln Met Ser Phe Gln Glu Thr Lys Asp Leu Gly Arg Leu
                325                 330                 335

Pro Thr Gly Arg Ser Val Glu Ile Val Glu Ile Thr Glu Gln Phe Ala
                340                 345                 350

Ser Ser Lys Glu Ala Asp Glu Lys Lys Lys Lys Gly Lys Lys
            355                 360                 365
```

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide

<400> SEQUENCE: 11

```
Ala Met Tyr Pro His Ile Phe Tyr Phe His Phe
1               5                   10
```

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

```
Phe Leu Asp Ser Lys Leu Gln Glu Ile
1               5
```

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

```
Phe Val Tyr Ser Glu Gly Gln Pro Phe
1               5
```

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

```
Val Lys His His Ser Pro Val Ser Trp
1               5
```

```
<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Arg Met Tyr Arg Asp Thr Phe Ser Tyr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Gly Pro Ser Arg Pro Arg Leu Asp Ala
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17

Asn Leu Pro Lys Tyr Tyr Ile Leu Leu
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide

<400> SEQUENCE: 18

Asn Thr Val Trp Leu Cys Tyr Glu Val
1               5

<210> SEQ ID NO 19
<211> LENGTH: 11
<212> TYPE: PRT
<213> ORGANISM: Artificial Sequence
<220> FEATURE:
<223> OTHER INFORMATION: Synthetic peptide

<400> SEQUENCE: 19

Arg His Ser Met Asp Pro Pro Thr Phe Thr Phe
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

Phe Val Tyr Ser Gln Arg Glu Leu Phe
1               5

<210> SEQ ID NO 21
```

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Lys Pro His Phe Arg Asn Thr Val Glu
1               5

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide

<400> SEQUENCE: 22

Arg Pro Ile Leu Ser Arg Arg Asn Thr Val Trp Leu
1               5                   10

<210> SEQ ID NO 23
<211> LENGTH: 180
<212> TYPE: PRT
<213> ORGANISM: Homo sapiens

<400> SEQUENCE: 23

Met Ala Ser Thr Ser Tyr Asp Tyr Cys Arg Val Pro Met Glu Asp Gly
1               5                   10                  15

Asp Lys Arg Cys Lys Leu Leu Leu Gly Ile Gly Ile Leu Val Leu Leu
                20                  25                  30

Ile Ile Val Ile Leu Gly Val Pro Leu Ile Ile Phe Thr Ile Lys Ala
            35                  40                  45

Asn Ser Glu Ala Cys Arg Asp Gly Leu Arg Ala Val Met Glu Cys Arg
        50                  55                  60

Asn Val Thr His Leu Leu Gln Gln Glu Leu Thr Glu Ala Gln Lys Gly
65                  70                  75                  80

Phe Gln Asp Val Glu Ala Gln Ala Ala Thr Cys Asn His Thr Val Met
                85                  90                  95

Ala Leu Met Ala Ser Leu Asp Ala Glu Lys Ala Gln Gly Gln Lys Lys
                100                 105                 110

Val Glu Glu Leu Glu Gly Glu Ile Thr Thr Leu Asn His Lys Leu Gln
            115                 120                 125

Asp Ala Ser Ala Glu Val Glu Arg Leu Arg Arg Glu Asn Gln Val Leu
        130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Leu Gly Leu Ser
                165                 170                 175

Ala Leu Leu Gln
            180

<210> SEQ ID NO 24
<211> LENGTH: 493
<212> TYPE: PRT
<213> ORGANISM: Homo sapiens

<400> SEQUENCE: 24

Met Ala Ser Gly Ile Leu Val Asn Val Lys Glu Glu Val Thr Cys Pro
1               5                   10                  15

```
Ile Cys Leu Glu Leu Leu Thr Gln Pro Leu Ser Leu Asp Cys Gly His
             20                  25                  30

Ser Phe Cys Gln Ala Cys Leu Thr Ala Asn His Lys Lys Ser Met Leu
             35                  40                  45

Asp Lys Gly Glu Ser Ser Cys Pro Val Cys Arg Ile Ser Tyr Gln Pro
 50                  55                  60

Glu Asn Ile Arg Pro Asn Arg His Val Ala Asn Ile Val Glu Lys Leu
 65                  70                  75                  80

Arg Glu Val Lys Leu Ser Pro Glu Gly Gln Lys Val Asp His Cys Ala
             85                  90                  95

Arg His Gly Glu Lys Leu Leu Leu Phe Cys Gln Glu Asp Gly Lys Val
            100                 105                 110

Ile Cys Trp Leu Cys Glu Arg Ser Gln Glu His Arg Gly His His Thr
            115                 120                 125

Phe Leu Thr Glu Glu Val Ala Arg Glu Tyr Gln Val Lys Leu Gln Ala
            130                 135                 140

Ala Leu Glu Met Leu Arg Gln Lys Gln Glu Ala Glu Glu Leu Glu
145                 150                 155                 160

Ala Asp Ile Arg Glu Glu Lys Ala Ser Trp Lys Thr Gln Ile Gln Tyr
            165                 170                 175

Asp Lys Thr Asn Val Leu Ala Asp Phe Glu Gln Leu Arg Asp Ile Leu
            180                 185                 190

Asp Trp Glu Glu Ser Asn Glu Leu Gln Asn Leu Glu Lys Glu Glu Glu
            195                 200                 205

Asp Ile Leu Lys Ser Leu Thr Asn Ser Glu Thr Glu Met Val Gln Gln
210                 215                 220

Thr Gln Ser Leu Arg Glu Leu Ile Ser Asp Leu Glu His Arg Leu Gln
225                 230                 235                 240

Gly Ser Val Met Glu Leu Leu Gln Gly Val Asp Gly Val Ile Lys Arg
            245                 250                 255

Thr Glu Asn Val Thr Leu Lys Lys Pro Glu Thr Phe Pro Lys Asn Gln
            260                 265                 270

Arg Arg Val Phe Arg Ala Pro Asp Leu Lys Gly Met Leu Glu Val Phe
            275                 280                 285

Arg Glu Leu Thr Asp Val Arg Arg Tyr Trp Val Asp Val Thr Val Ala
            290                 295                 300

Pro Asn Asn Ile Ser Cys Ala Val Ile Ser Glu Asp Lys Arg Gln Val
305                 310                 315                 320

Ser Ser Pro Lys Pro Gln Ile Ile Tyr Gly Ala Arg Gly Thr Arg Tyr
            325                 330                 335

Gln Thr Phe Val Asn Phe Asn Tyr Cys Thr Gly Ile Leu Gly Ser Gln
            340                 345                 350

Ser Ile Thr Ser Gly Lys His Tyr Trp Glu Val Asp Val Ser Lys Lys
            355                 360                 365

Thr Ala Trp Ile Leu Gly Val Cys Ala Gly Phe Gln Pro Asp Ala Met
            370                 375                 380

Cys Asn Ile Glu Lys Asn Glu Asn Tyr Gln Pro Lys Tyr Gly Tyr Trp
385                 390                 395                 400

Val Ile Gly Leu Glu Glu Gly Val Lys Cys Ser Ala Phe Gln Asp Ser
            405                 410                 415

Ser Phe His Thr Pro Ser Val Pro Phe Ile Val Pro Leu Ser Val Ile
            420                 425                 430

Ile Cys Pro Asp Arg Val Gly Val Phe Leu Asp Tyr Glu Ala Cys Thr
```

-continued

```
             435                 440                 445
Val Ser Phe Phe Asn Ile Thr Asn His Gly Phe Leu Ile Tyr Lys Phe
     450                 455                 460

Ser His Cys Ser Phe Ser Gln Pro Val Phe Pro Tyr Leu Asn Pro Arg
465                 470                 475                 480

Lys Cys Gly Val Pro Met Thr Leu Cys Ser Pro Ser Ser
                 485                 490
```